(12) United States Patent
Arnold et al.

(10) Patent No.: US 9,708,633 B2
(45) Date of Patent: *Jul. 18, 2017

(54) STABLE, FUNCTIONAL CHIMERIC CELLOBIOHYDROLASE CLASS I ENZYMES

(71) Applicant: The California Institute of Technology, Pasadena, CA (US)

(72) Inventors: Frances H. Arnold, La Canada, CA (US); Pete Heinzelman, Norman, OK (US)

(73) Assignee: California Institute of Technology, Pasadena, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/068,521

(22) Filed: Mar. 11, 2016

(65) Prior Publication Data

US 2017/0037441 A1 Feb. 9, 2017

Related U.S. Application Data

(60) Continuation of application No. 14/625,543, filed on Feb. 18, 2015, now Pat. No. 9,284,587, which is a division of application No. 13/151,190, filed on Jun. 1, 2011, now Pat. No. 8,962,295.

(60) Provisional application No. 61/350,412, filed on Jun. 1, 2010.

(51) Int. Cl.
| | |
|---|---|
| *C12N 9/42* | (2006.01) |
| *C07K 19/00* | (2006.01) |
| *C12P 19/14* | (2006.01) |
| *C12P 19/02* | (2006.01) |

(52) U.S. Cl.
CPC ............ *C12P 19/14* (2013.01); *C12N 9/2437* (2013.01); *C12P 19/02* (2013.01); *C12Y 302/01004* (2013.01); *C12Y 302/01074* (2013.01); *C12Y 302/01091* (2013.01); *C07K 2319/35* (2013.01)

(58) Field of Classification Search
CPC ... C07K 2319/35; C12N 9/2437; C12P 19/02; C12P 19/14; C12Y 302/01004; C12Y 302/01074; C12Y 302/01091
See application file for complete search history.

(56) References Cited

U.S. PATENT DOCUMENTS

| | | |
|---|---|---|
| 6,558,937 B1 | 5/2003 | Gielkens et al. |
| 2006/0246566 A1 | 11/2006 | Vehmaanpera et al. |
| 2008/0268517 A1 | 10/2008 | Arnold |
| 2009/0280105 A1 | 11/2009 | Gusakov et al. |

FOREIGN PATENT DOCUMENTS

| | | |
|---|---|---|
| EP | 2357227 A1 | 8/2011 |
| WO | 2005017106 A2 | 2/2005 |
| WO | 2009138877 A2 | 11/2009 |
| WO | 2010091441 A2 | 8/2010 |

OTHER PUBLICATIONS

Zhao, Tian, First Office Action, Chinese Application No. 201180022906.8, The State Intellectual Property Office of the People's Republic of China, Issue Date: Nov. 27, 2013.
Zhao, Tian, Second Office Action, Chinese Application No. 201180022906.8, The State Intellectual Property Office of the People's Republic of China, Issue Date: Aug. 18, 2014.
Kaur, J. et al., "Directed Evolution: An Approach to Engineer Enzymes", Criticial Reviews in Biotechnology, 2006, vol. 26, pp. 165-199.
Park, Jung Min, International Search Report and Written Opinion, PCT/US2011/038812, Korean Intellectual Property Office, Feb. 17, 2012.
Heinzelman, P. et al., "A family of thermostable fungal cellulases created by structure-guided recombination", Proceedings of the National Academy of Sciences, vol. 106, No. 14, Apr. 17, 2009, pp. 5610-5615.
Heinzelman, P. et al., "Efficient screening of fungal cellobiohydrolase class I enzymes for thermostabilizing sequence blocks by SCHEMA structure-guided recombination", Protein Engineering, Design & Selection, Sep. 16, 2010 pp. 871-880.
Huber, Angelika, Supplementary European Search Report, European Patent No. EP 11 79 0360, Nov. 6, 2013.
Voutilainen, Sanni P. et al., "Improving the thermostability and activity of Melanocarpus albomyces cellobiohydrolase Cel7B", Applied Microbiology and Biotechnology, Springer, Berlin, DE, vol. 83, No. 2, Jan. 16, 2009, pp. 261-272.

*Primary Examiner* — Delia Ramirez

(74) *Attorney, Agent, or Firm* — Gavrilovich, Dodd & Lindsey LLP

(57) ABSTRACT

The present disclosure relates to CBH I chimera fusion polypeptides, nucleic acids encoding the polypeptides, and host cells for producing the polypeptides.

8 Claims, 7 Drawing Sheets

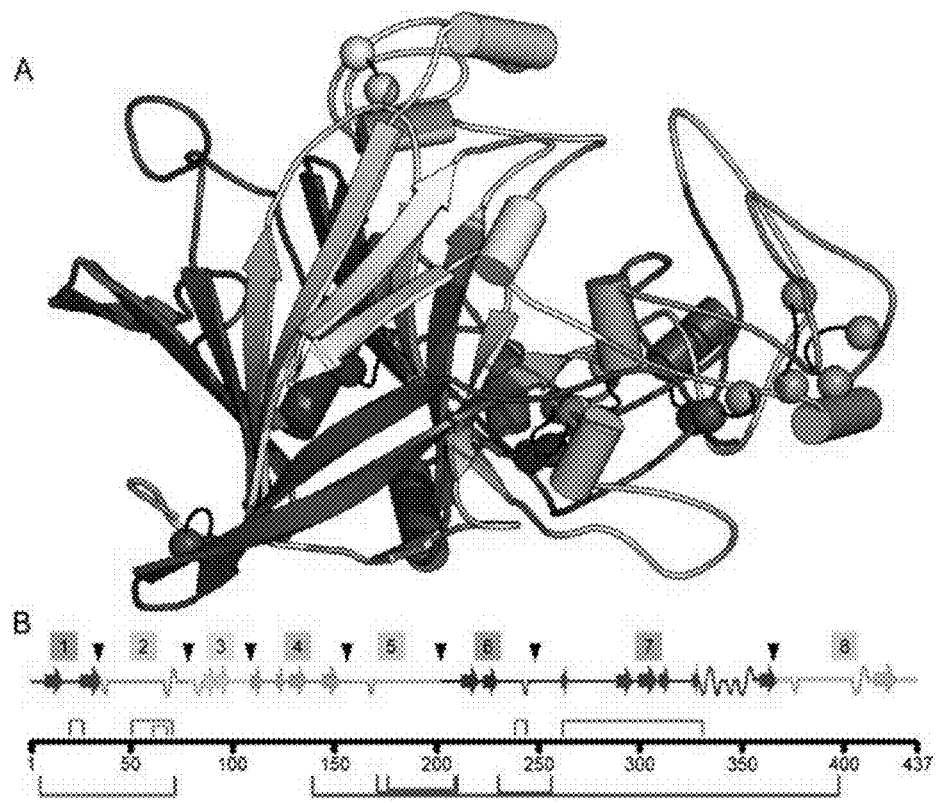
FIGURE 1A-B
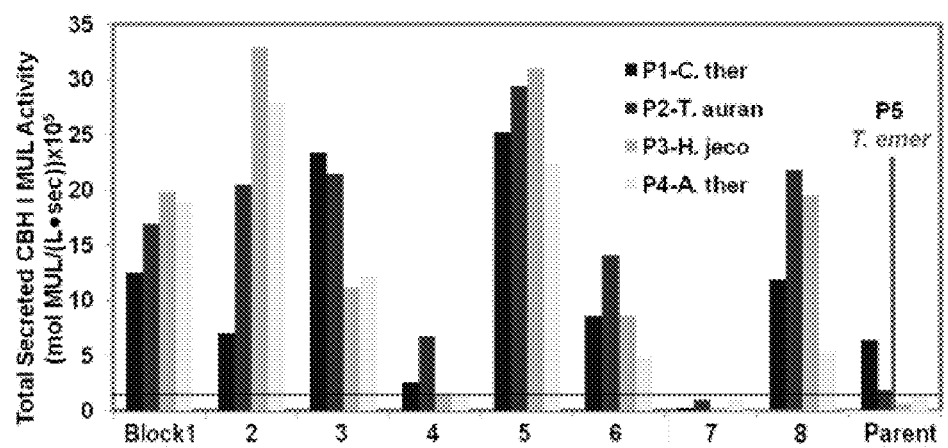
FIGURE 2

FIGURE 7

STABLE, FUNCTIONAL CHIMERIC CELLOBIOHYDROLASE CLASS I ENZYMES

CROSS REFERENCE TO RELATED APPLICATIONS

This application is a continuation of U.S. patent application Ser. No. 14/625,543, filed Feb. 18, 2015 (now U.S. Pat. No. 9,284,587), which application is a divisional of U.S. patent application Ser. No. 13/151,190, filed Jun. 1, 2011 (now U.S. Pat. No. 8,962,295), which claims priority under 35 U.S.C. §119 to U.S. Provisional Application Ser. No. 61/350,412, filed Jun. 1, 2010, the disclosures of which are incorporated herein by reference.

STATEMENT REGARDING FEDERALLY SPONSORED RESEARCH

This invention was made with government support under grant no. W911NF-09-D-0001 awarded by the Army Research Office. The government has certain rights in the invention.

TECHNICAL FIELD

The present disclosure relates to biomolecular engineering and design, and engineered proteins and nucleic acids.

BACKGROUND

The performance of cellulase mixtures in biomass conversion processes depends on many enzyme properties including stability, product inhibition, synergy among different cellulase components, productive binding versus nonproductive adsorption and pH dependence, in addition to the cellulose substrate physical state and composition. Given the multivariate nature of cellulose hydrolysis, it is desirable to have diverse cellulases to choose from in order to optimize enzyme formulations for different applications and feedstocks.

SUMMARY

The disclosure provides a substantially purified chimeric polypeptide comprising at least two domains from at least two different parental cellobiohydrolase I (CBH I) polypeptides, wherein the domains comprise from N- to C-terminus: (segment 1)-(segment 2)-(segment 3)-(segment 4)-(segment 5)-(segment 6)-(segment 7)-(segment 8); wherein: segment 1 comprises a sequence that is at least 50-100% identical to amino acid residue from about 1 or from about 18 or 19 to about $x_1$ of SEQ ID NO:2 ("1"), SEQ ID NO:4 ("2"), SEQ ID NO:6 ("3"), SEQ ID NO:8 ("4"), or SEQ ID NO:10 ("5"); segment 2 comprises a sequence that is at least 50-100% identical to amino acid residue $x_1$ to about $x_2$ of SEQ ID NO:2 ("1"), SEQ ID NO:4 ("2"), SEQ ID NO:6 ("3"), SEQ ID NO:8 ("4"), or SEQ ID NO:10 ("5"); segment 3 comprises a sequence that is at least 50-100% identical to amino acid residue $x_2$ to about $x_3$ of SEQ ID NO:2 ("1"), SEQ ID NO:4 ("2"), SEQ ID NO:6 ("3"), SEQ ID NO:8 ("4"), or SEQ ID NO:10 ("5"); segment 4 comprises a sequence that is at least 50-100% identical to amino acid residue $x_3$ to about $x_4$ of SEQ ID NO:2 ("1"), SEQ ID NO:4 ("2"), SEQ ID NO:6 ("3"), SEQ ID NO:8 ("4"), or SEQ ID NO:10 ("5"); segment 5 comprises a sequence that is at least 50-100% identical to about amino acid residue $x_4$ to about $x_5$ of SEQ ID NO:2 ("1"), SEQ ID NO:4 ("2"), SEQ ID NO:6 ("3"), SEQ ID NO:8 ("4"), or SEQ ID NO:10 ("5"); segment 6 comprises a sequence that is at least 50-100% identical to amino acid residue $x_5$ to about $x_6$ of SEQ ID NO:2 ("1"), SEQ ID NO:4 ("2"), SEQ ID NO:6 ("3"), SEQ ID NO:8 ("4"), or SEQ ID NO:10 ("5"); segment 7 comprises a sequence that is at least 50-100% identical to amino acid residue $x_6$ to about $x_7$ of SEQ ID NO:2 ("1"), SEQ ID NO:4 ("2"), SEQ ID NO:6 ("3"), SEQ ID NO:8 ("4"), or SEQ ID NO:10 ("5"); and segment 8 comprises a sequence that is at least 50-100% identical to amino acid residue $x_7$ to about $x_8$ of SEQ ID NO:2 ("1"), SEQ ID NO:4 ("2"), SEQ ID NO:6 ("3"), SEQ ID NO:8 ("4"), or SEQ ID NO:10 ("5"); and wherein $x_1$ is residue 47, 48, 49, 50, 51, or 52 of SEQ ID NO:2, 4, 6, or 8, or residue 48, 49, 50, 51, 52 or 53 of SEQ ID NO:10; $x_2$ is residue 92, 93, 94 95, 96 or 97 of SEQ ID NO:2 or 10, or residue 91, 92, 93, 94, 95, or 96 of SEQ ID NO:4, 6, or 8; $x_3$ is residue 127, 128, 129, 130, 131 or 132 of SEQ ID NO:2, or residue 125, 126, 127, 128, 129 or 130 of SEQ ID NO:4 or 6, or residue 126, 127, 128, 129, 130 or 131 of SEQ ID NO:8, or residue 123, 124, 125, 126, 127 or 128 or SEQ ID NO:10; $x_4$ is residue 175, 176, 177, 178, 180 or 181 of SEQ ID NO:2, or residue 173, 174, 175, 176, 177 or 178 of SEQ ID NO:4 or SEQ ID NO:6, or residue 174, 175, 176, 177, 178 or 179 of SEQ ID NO:8, or 171, 172, 173, 174, 175, or 176 of SEQ ID NO:10; $x_5$ is 221, 222, 223, 224, 225, or 226 of SEQ ID NO:2, or residue 219, 220, 221, 222, 223 or 224 of SEQ ID NO:4 or SEQ ID NO:6, or residue 220, 221, 222, 223, 224 or 225 of SEQ ID NO:8, or 217, 218, 219, 220, 221 or 222 of SEQ ID NO:10; $x_6$ is residue 268, 269, 270, 271, 272 or 273 of SEQ ID NO:2, or residue 266, 267, 268, 269, 270 or 271 of SEQ ID NO:4 or SEQ ID NO:6, or residue 267, 268, 269, 270, 271 or 272 of SEQ ID NO:8, or 264, 265, 266, 267, 268 or 269 of SEQ ID NO:10; $x_7$ is residue 384, 385, 386, 387, 388 or 389 of SEQ ID NO:2, or residue 385, 386, 387, 388, 389 or 390 of SEQ ID NO:4, or residue 378, 379, 380, 381, 382 or 383 or SEQ ID NO:6, or residue 383, 384, 385, 386, 387 or 388 of SEQ ID NO:8 or 10; and $x_8$ is an amino acid residue corresponding to residue 454, of SEQ ID NO:2, residue 457 of SEQ ID NO:4, residue 458 of SEQ ID NO:6, residue 453 of SEQ ID NO:8, residue 455 of SEQ ID NO:10 or the C-terminus of the polypeptide having the sequence of SEQ ID NO:2, SEQ ID NO:4, SEQ ID NO:6, SEQ ID NO:8 or SEQ ID NO:10, and wherein the chimeric polypeptide has cellobiohydrolase activity and improved thermostability, pH stability and/or expression compared to a CBH I polypeptide comprising SEQ ID NO:2, 4, 6, 8 or 10. In another embodiment, of the foregoing, segment 1 comprises amino acid residue from about 1 or from about 18 or 19 to about $x_1$ of SEQ ID NO:2 ("1"), SEQ ID NO:4 ("2"), SEQ ID NO:6 ("3"), SEQ ID NO:8 ("4"), or SEQ ID NO:10 ("5") and having 1-10 conservative amino acid substitutions; segment 2 is from about amino acid residue $x_1$ to about $x_2$ of SEQ ID NO:2 ("1"), SEQ ID NO:4 ("2"), SEQ ID NO:6 ("3"), SEQ ID NO:8 ("4"), or SEQ ID NO:10 ("5") and having about 1-10 conservative amino acid substitutions; segment 3 is from about amino acid residue $x_2$ to about $x_3$ of SEQ ID NO:2 ("1"), SEQ ID NO:4 ("2"), SEQ ID NO:6 ("3"), SEQ ID NO:8 ("4"), or SEQ ID NO:10 ("5") and having about 1-10 conservative amino acid substitutions; segment 4 is from about amino acid residue $x_3$ to about $x_4$ of SEQ ID NO:2 ("1"), SEQ ID NO:4 ("2"), SEQ ID NO:6 ("3"), SEQ ID NO:8 ("4"), or SEQ ID NO:10 ("5") and having about 1-10 conservative amino acid substitutions; segment 5 is from about amino acid residue $x_4$ to about $x_5$ of SEQ ID NO:2 ("1"), SEQ ID NO:4 ("2"), SEQ ID NO:6 ("3"), SEQ ID NO:8 ("4"), or SEQ ID NO:10 ("5") and having about 1-10 conservative amino acid substitutions; segment 6 is from about amino acid residue $x_5$ to about $x_6$ of SEQ ID NO:2 ("1"), SEQ ID NO:4 ("2"), SEQ ID NO:6 ("3"), SEQ ID NO:8 ("4"), or SEQ ID NO:10 ("5") and having about 1-10 conservative amino acid substitutions; segment 7 is from about amino acid residue $x_6$ to about $x_7$ of SEQ ID NO:2 ("1"), SEQ ID NO:4 ("2"), SEQ ID NO:6 ("3"), SEQ ID NO:8 ("4"), or SEQ ID NO:10 ("5") and having about 1-10 conservative amino acid substitutions; and segment 8 is from about amino acid residue $x_7$ to about $x_8$ of SEQ ID NO:2 ("1"), SEQ ID NO:4 ("2"), SEQ ID NO:6 ("3"), SEQ ID NO:8 ("4"), or SEQ ID NO:10 ("5") and having about 1-10 conservative amino acid substitutions. In yet a further embodiment of any of the foregoing the polypeptide is at least 60-100% identical to a sequence selected from the group consisting of SEQ ID NO:19, 20, 21, 22, 23, 24, 25, 26, 27, 28, 29, 30, 31, 32, 33 and 34. In yet a further embodiment of any of the foregoing the polypeptide comprises a leader sequence in operable linkage to the N-terminal amino acid. In yet a further embodiment of any of the foregoing the polypeptide further comprises a C-terminal CBM domain comprising a sequence selected from the group consisting of SEQ ID NO:16, 17 and 18. In yet a further embodiment of any of the foregoing the at least two different parental cellobiohydrolase I (CBH I) polypeptides comprise sequences selected from the group consisting of SEQ ID NO:2, 4, 6, 8 and 10. In yet a further embodiment of any of the foregoing polypeptide has a segment structure selected from the group consisting of 55153552, 12153252, 25152252, 12152252, 55152252, 55515555, 55555551, 55515551, 55525555, 55555552, 55525552, 55555155, 55555515, 55555115, 55555255, 55555525, 55555225, 34152252 (SEQ ID NO:19), 55153552 (SEQ ID NO:20), 32153252 (SEQ ID NO:21), 55155552 (SEQ ID NO:22), 22153252 (SEQ ID NO:23), 52152552, (SEQ ID NO:24), 12153252 (SEQ ID NO:25), 45153252 (SEQ ID NO:26), 12153552 (SEQ ID NO:27), 25152252 (SEQ ID NO:28), 13152552 (SEQ ID NO:29), 12152252 (SEQ ID NO:30), 55153252 (SEQ ID NO:31), 55552252 (SEQ ID NO:32), 55152552 (SEQ ID NO:33) and 55152252 (SEQ ID NO:34).

The disclosure also provides a polynucleotide encoding a polypeptide as described in any of the foregoing embodiments, a vector containing the polynucleotide, and a host cell (e.g., a plant or fungal cell) comprising the polynucleotide or vector.

The disclosure also provide an enzymatic preparation comprising a polypeptide as described above and elsewhere herein. In yet another embodiment, the enzymatic preparation further comprises a thermostabilized cellobiohydrolase class II enzymatic chimera.

The disclosure also provides a method of treating a biomass comprising cellulose, the method comprising contacting the biomass with an enzymatic preparation of the disclosure.

The disclosure also provides a method for generating a polypeptide of claim 1 having improved activity or stability compared to a parent or class of parent polypeptides, comprising: identifying a plurality (P) of evolutionary, structurally or evolutionary and structurally related polypeptides; selecting a set of crossover locations comprising N peptide segments in at least a first polypeptide and at least a second polypeptide of the plurality of related polypeptides; selecting a parent from the plurality of evolutionary, structurally or evolutionary and structurally related polypeptides having stable functional expression; generating a plurality of chimeras comprising N−1 peptide segments from the parent and one heterologous peptide segment from one other polypeptide from the plurality of evolutionary, structurally or evolutionary and structurally related polypeptides; identifying improved chimeras having increased activity or stability and identifying the heterologous peptide segment as activity/stability-associated peptide segments in the improved monomeras; generating a sample set (xP") of recombined, recombinant proteins comprising an activity/stability-associated peptide segments from each of the at least first polypeptide and second polypeptide, wherein x<1; measuring stability of the sample set of expressed-folded recombined, recombinant proteins; generating a plurality of chimera polypeptides comprising one or more activity/stability-associated peptide segments.

BRIEF DESCRIPTION OF THE FIGURES

FIG. 1A-B shows a three dimensional structure and recombination block diagram of a CBH I polypeptide. (A) CBH I catalytic domain three-dimensional structure. Disulfide-bonded Cys residues are denoted by spheres connected by black lines. (B) CBH I recombination block divisions and secondary structure diagram. Interblock disulfide bonds are denoted by maroon lines, intrablock disulfides by light blue lines, block divisions by black arrows. Residue numbering for T. emersonii CBH I.

FIG. 2 shows total secreted CBH I MUL-hydrolyzing activity for parent CBH Is and 32 monomeras. Monomeras contain single block substitutions from parents 1-4 into parent 5 (from T. emersonii). Total secreted CBH I MUL-hydrolyzing activity for T. emersonii CBH I denoted by pink bar. Yeast secretion culture supernatants were incubated with 300 μM soluble, fluorescent MUL substrate for 30 minutes at 45° C. Mean of single activity measurements for three independent T. emersonii secretion cultures is $2.3 \times 10^{-4}$ mol MUL/(L·s), standard deviation is $3.0 \times 10$-5 mol MUL/(L·s). All other values represent single cultures and measurements. Black line at bottom of figure denotes threshold activity value of $1.6 \times 10^{-5}$ mol MUL/(L·s) for $T_{50}$ measurement.

FIG. 7 shows ClustalW multiple sequence alignment of CBH I parent catalytic domains (SEQ ID N0:2, 4, 6, 8, 10, respectively), block boundaries denoted by black lines.

DETAILED DESCRIPTION

Figures 3, 4:
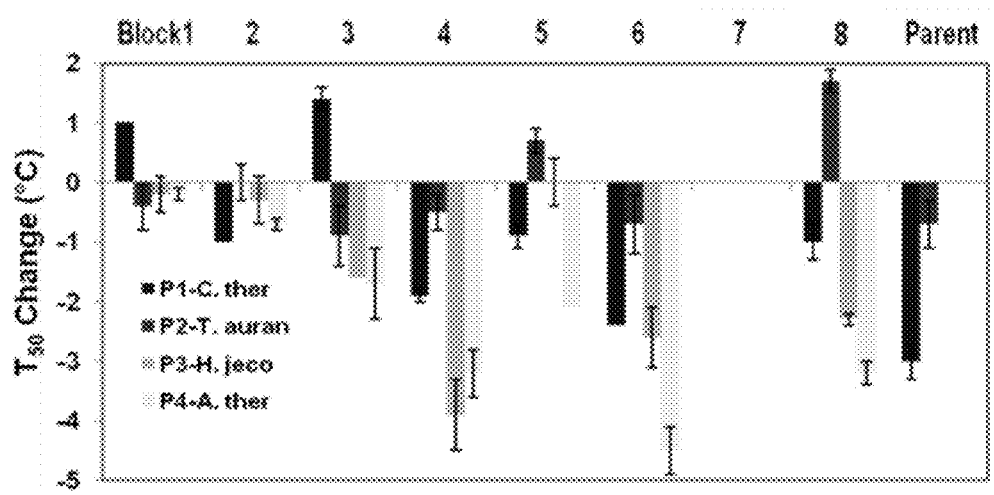
FIG. 3 shows changes in $T_{50}$ values (° C.) relative to T. emersonii ($T_{50}$=62.9+/−0.3° C.) parent for 28 CBH I monomeras. Monomeras contain single block substitutions from parents 1-4 into parent 5 (from T. emersonii). Error bars for monomeras represent extreme values of two duplicate measurements. Error bars for parents represent standard deviations for between 3 and 8 replicates. $T_{50}$ values for respective C. thermophilum and T. aurantiacus parent CBH Is are 59.9+/−0.3° C. and 62.2+/−0.4° C. H. jecorina and A. thermophilum parent CBH Is were not secreted.
FIG. 4 shows $T_{50}$ values, total yeast secreted activity (mol MUL/(L·s)×$10^5$) and block sequences for parent CBH Is. $T_{50}$ error bars for monomeras represent extreme values of two duplicate measurements, error bars for parents represent standard deviations for between 3 and 8 replicates. Total secreted activity values [mol MUL/(L·s)] are a single measurement for a single culture, with the exception of parent 5, T. emersonii, which has mean and standard deviation total yeast secreted activity of (2.3+/−0.3)×$10^{-4}$ mol MUL/(L·s) for single measurements of three independent cultures. Secretion levels for parent 3 (H. jecorina) and parent 4, (A. thermophilum), are below the threshold for $T_{50}$ measurement.

As used herein and in the appended claims, the singular forms "a," "and," and "the" include plural referents unless the context clearly dictates otherwise. Thus, for example, reference to "a domain" includes a plurality of such domains and reference to "the protein" includes reference to one or more proteins, and so forth.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Although methods and materials similar or equivalent to those described herein can be used in the practice of the disclosed methods and compositions, the exemplary methods, devices and materials are described herein.

Unless defined otherwise, all technical and scientific terms used herein have the same meaning as commonly understood to one of ordinary skill in the art to which this disclosure belongs. Thus, as used throughout the instant application, the following terms shall have the following meanings.

Given the demonstrated utility of SCHEMA and the monomera block screening approach for creating new thermostable enzymes, it is instructive to compare and contrast this strategy with other methods for improving enzyme thermostability. Consensus mutagenesis is possibly the most broadly used enzyme thermostabilization strategy that does not employ high throughput screening. Consensus mutagenesis is based on aligning a large, e.g., dozens or hundreds, number of related enzyme sequences and identifying residues that appear with high frequency at a given position as being potentially stabilizing. Changing the residue identity from a low frequency to a higher frequency amino acid at a given position is then predicted to improve the thermostability of the enzyme into which such a substitution is made.

Despite the successful use of consensus mutagenesis to predict single residue substitutions that improve enzyme thermostability, the need for a large number of phylogenetically diverse sequences to ensure prediction accuracy is a considerable limitation. Successful applications of consensus mutagenesis have incorporated dozens, if not hundreds, of enzyme homolog sequences. While the CAZy database (see, the worldwide web at cazy.org) contains more than forty CBH I or CBH I-related gene sequences that could be used in applying consensus mutagenesis to CBH I stabilization, there are many enzyme classes for which such a large set of known sequences is not available. Furthermore, even when many sequences are available, the ability to make accurate predictions of stabilizing residues is limited by the fact that the enzymes have evolved from common ancestors. Evolution from a small starting pool biases residue frequencies in the full homolog set toward amino acids appearing in the parental sequences, which confounds any stabilizing role that amino acid might have. Given that SCHEMA recombination requires only the sequences of the parent enzymes and a crystal structure for either a parent enzyme or homolog, the monomera block screening approach we have described can be a useful alternative to consensus mutagenesis for improving stability.

This demonstration of enzyme stabilization by SCHEMA recombination has been made in the context of industrially relevant fungal CBH Is, which are the principal components of cellulase mixtures used in large-scale biomass conversion processes. These enzymes are notoriously difficult to express in a heterologous host and few protein engineering efforts have led to improved enzymes, despite their industrial importance. The most thermostable CBH I described to date is a variant of $T.$ $emersonii$, secreted from a recombinant $S.$ cerevisiae host that contains three additional, rationally-designed disulfide bonds, G4C-A72C, N54C-P191C and T243C-A375C. The single G4C-A72C engineered disulfide *T. emersonii* catalytic domain used as a SCHEMA recombination parent is provided herein. The respective $T_m$ values of the single- and triple-disulfide-bond variants are reported to be 80° C. and 84° C., as measured by circular dichroism (CD), and their half-lives at 70° C. are reported to be 270 and 320 min in the absence of substrate. These numbers for the G4C-A72C mutant do not align with the observed $T_{50}$ value of 62.9+/−0.3° C. for the *T. emersonii* CBH I parent in yeast secretion culture supernatant and also imply thermostability much greater than what we observe in solid substrate hydrolysis assays, where the *T. emersonii* parent is inactive at temperatures above 65° C.

The high cost of the fungal cellulase mixtures that are commonly employed in biomass-to-biofuel conversion processes is one of the major limitations to achieving economically viable production of transportation fuel from inedible plant matter. The operating costs of cellulase treatments can be reduced by improving the thermostability of these enzyme mixtures. Cellulase operating lifetime increases with thermostability, allowing thermostable cellulases to hydrolyze more cellulose per unit enzyme than their less stable counterparts throughout the course of biomass degradation. Thermostable cellulases can also operate at higher temperatures and derive a benefit from higher specific activities. This increased hydrolysis reduces the enzyme loading needed to convert cellulosic biomass into fermentable sugars. In addition to stability, properties such as specific activity, pH dependence, product inhibition and productive versus nonproductive adsorption on solid substrate surfaces all contribute to the overall performance of a cellulase mixture.

Class I cellobiohydrolases (CBH Is or family 7 glycosyl hydrolases) are the principal components of industrial cellulase mixtures and account for approximately 60 wt % of the cellulases secreted by the prevalent commercial cellulase production host, the filamentous fungus *Hypocrea jecorina* (*T. reesei*). As such, CBH I's have been the subject of multiple enzyme engineering efforts aimed primarily at improving CBH I thermostability. Both high throughput screening (HTS) of CBH I random mutant libraries and rational disulfide bond engineering have been employed to create stable CBH I variants. The applicability of HTS is limited to CBH I's that are expressed by a suitable heterologous host at levels sufficient to enable library characterization. The applicability of disulfide bond engineering is limited to CBH I's for which a crystal structure exists. Neither of these approaches generate the CBH I gene sequence diversity that could lead to improvements in the suite of enzyme properties enumerated above. The disclosure describes a method for engineering cellulases (and other proteins) that reliably improves thermostability while simultaneously retaining function and providing a high level of sequence diversity and also provides such compositions and engineered polypeptides.

The majority of biomass conversion processes use mixtures of fungal cellulases (primarily cellulobiohydrolase class II (CBH II), cellobiohydrolase class I (CBH I), endo-glucanases and β-glucosidase) to achieve high levels of cellulose hydrolysis. Generating a diverse group of thermostable CBH I enzyme chimeras is the first step in building an inventory of stable, highly active cellulases from which enzyme mixtures can be formulated and optimized for specific applications and feedstocks. These chimeric CBH I's of the disclosure can be used in combination with other cellobiohydrolases (e.g., wild-type and chimeric CBH II's, see, e.g., PCT/US2010/027248 and PCT/US2010/30133, the disclosures of which are incorporated herein by reference).

SCHEMA has been used previously to create families of hundreds of active CBH II, β-lactamase and cytochrome P450 enzyme chimeras. SCHEMA uses protein structure data to define boundaries of contiguous amino acid "blocks" which minimize <E>, the library average number of amino acid side chain contacts that are broken when the blocks are swapped among different parents. It has been shown that the probability that a β-lactamase chimera was folded and active was inversely related to the value of E for that sequence. The RASPP (Recombination as Shortest Path Problem) algorithm was used to identify the block boundaries that minimized <E> relative to the library average number of mutations, <m>. More than 20% of the ~500 unique chimeras characterized from a β-lactamase collection comprised of 8 blocks from 3 parents ($3^8$=6,561 possible sequences) were catalytically active. A similar approach produced a 3-parent, 8-block cytochrome P450 chimera family containing more than 2,300 novel, catalytically active enzymes. Chimeras from these two collections were characterized by high numbers of mutations, 66 and 72 amino acids on average from the closest parent, respectively. SCHEMA/RASPP thus enabled design of chimera families having significant sequence diversity and an appreciable fraction of functional members.

It has also been shown that the thermostabilities of SCHEMA chimeras can be predicted based on sequence-stability data from a small sample of the sequences. Linear regression modeling of thermal inactivation data for 184 cytochrome P450 chimeras showed that SCHEMA blocks made additive contributions to thermostability. More than 300 chimeras were predicted to be thermostable by this model, and all 44 that were tested were more stable than the most stable parent. It was estimated that as few as 35 thermostability measurements could be used to predict the most thermostable chimeras. Furthermore, the thermostable P450 chimeras displayed unique activity and specificity profiles, demonstrating that chimeragenesis can lead to additional useful enzyme properties. The disclosure demonstrates that SCHEMA recombination of CBH II enzymes can generate chimeric cellulases that are active on phosphoric acid swollen cellulose (PASC) at high temperatures, over extended periods of time, and broad ranges of pH.

The total number of chimeras that can be made by swapping sequence blocks is $p^b$, where p is the number of parents and b is the number of blocks into which each parent is divided. Including more parent enzymes in the construction of a SCHEMA recombination family generates many more potential unique chimeras and enables inclusion of more potentially-beneficial mutations. Whereas 6,561 chimeras can be made by recombination of 3 parents and 8 blocks, adding two more parent sequences increases the family size to more than 390,000. The number of mutations explored by recombination depends on the parent sequence identities. For the CBH Is, relative to the *T. emersonii* background parent (parent 5 (P5)), parent 1 (*C. thermophilum*) contains 151 mutations, parent 2 (*T. aurantiacus*) adds 43 unique mutations, parent 3 (*H. jecorina*) brings 100 more unique mutations, and parent 4 (*A. thermophilum*) increases the mutation count by 52, bringing the total number of mutations that can be searched by recombination to 336.

The drawback to working with a larger chimera family is that more chimeras must be characterized in order to build a predictive stability model. It can be costly if a significant proportion of the sample chimeras do not express in functional form. The disclosure demonstrates that desirable sequences can be identified efficiently with a monomera screening approach, in which individual blocks substitutions are made in the background of a stable, well-expressed parent. Relative to a chimera sample set chosen to test interactions among blocks, i.e. the importance of the background sequence, this strategy reduces the number of nonproductive sequences that are constructed.

Stability measurements made for the background parent and 28 secreted members of a 32-member CBH I monomera set allowed stability contributions to be estimated for 36 of the 40 blocks comprising the 5-parent, 8-block CBH I chimera family. Assuming no nonlinear stability effects among blocks and that block 7, parent 5 (B7P5) is the most stabilizing block at position 7 in all chimera backgrounds, these measurements allow prediction of the most stable of $5^8=390,625$ CBH I chimera sequences. This represents an increase in screening efficiency relative to the prior CBH II recombination work but rests on the assumption that the blocks contribute additively to overall stability and does not test the linear model.

The disclosure demonstrates the robustness of SCHEMA recombination for creating active chimeras from parent enzymes that feature a large number of disulfide bonds. SCHEMA seeks to define block boundaries so that interactions among blocks are similar to those that occur in the parent enzymes. Block boundaries, however, are defined without regard for disulfide bonds. As such, the presence of 10 disulfide bonds, 5 of which link Cys residues lying in different blocks, poses a new test of SCHEMA's ability to generate chimera family designs that lead to a large fraction of active members. As shown by 28 of 32 monomeras and 16 of 16 predicted stable chimeras being secreted as active cellulases, SCHEMA recombination can generate a large fraction of active chimeras even when the protein is cross-linked by a large number of disulfide bonds. These results suggest that SCHEMA recombination conserves the appropriate position and orientation of Cys residues for disulfide formation.

Linear block stability contributions that allow quantitative prediction of chimera thermostability stand alongside the high sequence diversity and large fraction of active members as useful features of SCHEMA chimera families. Block 7 is the largest block, with 116 residues that comprise 27% of the CBH I catalytic domain. The reduced ability to make substitutions at this position markedly reduces the total number of mutations encompassed by the monomera sample set screen. In particular, 119 of the 336 total unique mutations in the 32 monomera sample set are contained within block 7. High E values do not necessarily predict the resistance of block 7 to recombination. To test this further subblocks of block 7 were generated and recombined. A subblock that increases the stability of not only the corresponding monomera but also all five of the stable chimeras into which it is substituted was identified and shows that subdividing a recombination block can generate further stability improvements.

This five-parent SCHEMA recombination has generated a set of thermostable CBH I chimeras that are a key addition to the previously described thermostable CBH II chimeras[7,8] in the assembly of an inventory of thermostable fungal cellulases from which application-specific mixtures can be formulated. Additionally, this work shows that the monomera screening strategy makes tractable the prediction of desirable chimera sequences within large families, thus increasing the utility of SCHEMA for exploring large swaths of enzyme sequence space. Furthermore, the observed improvements in chimera properties and the high fraction of active recombined enzymes shows that SCHEMA recombination can be applied to enzymes that contain extensive posttranslational modifications. As such, these results are relevant not only to enzyme engineering in the context of industrial biomass conversion processes but also for engineering other proteins for which high sequence diversity is desirable and/or whose properties are not easily improved by mutagenesis and high throughput screening.

Using the methods described herein a number of chimeric polypeptides having cellobiohydrolases activity were generated having improved characteristics compared to the wild-type parental CBH I proteins.

A diverse CBH I chimera sample set corresponding to an 8-block, 5-parent family containing more than 390,000 unique sequences was used. In order to predict the most stable members of this chimera family while still sampling only a limited set of chimeric genes (~30-40), experience was used to simplify the sample set design and maximize the number of sample genes expected to be secreted in functional form. In particular, it was hypothesized that SCHEMA blocks would make additive or at least cumulative contributions to chimera stability. It was further assumed that using a highly expressed parent as the background into which single blocks from homologous parents are substituted would increase the probability that the sample sequence will be secreted and functional. Thus a set of CBH I "monomeras", chimeras was constructed which contain a single block substitution, in the background of a well-expressed parent enzyme. This was an efficient approach for rapidly screening homologous enzymes for stabilizing blocks of sequence. The task of predicting the most stable chimeras is reduced to making stability measurements for the parent enzyme and 32 monomeras made in that background. Diverse thermostable chimeras can then be assembled from stabilizing and neutral blocks.

"Amino acid" is a molecule having the structure wherein a central carbon atom is linked to a hydrogen atom, a carboxylic acid group (the carbon atom of which is referred to herein as a "carboxyl carbon atom"), an amino group (the nitrogen atom of which is referred to herein as an "amino nitrogen atom"), and a side chain group, R. When incorporated into a peptide, polypeptide, or protein, an amino acid loses one or more atoms of its amino acid carboxylic groups in the dehydration reaction that links one amino acid to another. As a result, when incorporated into a protein, an amino acid is referred to as an "amino acid residue."

"Protein" or "polypeptide" refers to any polymer of two or more individual amino acids (whether or not naturally occurring) linked via a peptide bond. The term "protein" is understood to include the terms "polypeptide" and "peptide" (which, at times may be used interchangeably herein) within its meaning. In addition, proteins comprising multiple polypeptide subunits (e.g., DNA polymerase III, RNA polymerase II) or other components (for example, an RNA molecule, as occurs in telomerase) will also be understood to be included within the meaning of "protein" as used herein. Similarly, fragments of proteins and polypeptides are also within the scope of the disclosure and may be referred to herein as "proteins." In one embodiment of the disclosure, a stabilized protein comprises a chimera of two or more parental peptide segments.

A particular amino acid sequence of a given protein (i.e., the polypeptide's "primary structure," when written from the amino-terminus to carboxy-terminus) is determined by the nucleotide sequence of the coding portion of a mRNA, which is in turn specified by genetic information, typically genomic DNA (including organelle DNA, e.g., mitochondrial or chloroplast DNA). Thus, determining the sequence of a gene assists in predicting the primary sequence of a corresponding polypeptide and more particular the role or activity of the polypeptide or proteins encoded by that gene or polynucleotide sequence.

"Fused," "operably linked," and "operably associated" are used interchangeably herein to broadly refer to a chemical or physical coupling of two otherwise distinct domains or peptide segments, wherein each domain or peptide segment when operably linked can provide a functional polypeptide having a desired activity. Domains or peptide segments can be directly linked or connected through peptide linkers such that they are functional or can be fused through other intermediates or chemical bonds. For example, two domains can be part of the same coding sequence, wherein the polynucleotides are in frame such that the polynucleotide when transcribed encodes a single mRNA that when translated comprises both domains as a single polypeptide. Alternatively, both domains can be separately expressed as individual polypeptides and fused to one another using chemical methods. Typically, the coding domains will be linked "in-frame" either directly of separated by a peptide linker and encoded by a single polynucleotide. Various coding sequences for peptide linkers and peptide are known in the art.

"Polynucleotide" or "nucleic acid sequence" refers to a polymeric form of nucleotides. In some instances a polynucleotide refers to a sequence that is not immediately contiguous with either of the coding sequences with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA) independent of other sequences. The nucleotides of the disclosure can be ribonucleotides, deoxyribonucleotides, or modified forms of either nucleotide. A polynucleotides as used herein refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. The term polynucleotide encompasses genomic DNA or RNA (depending upon the organism, i.e., RNA genome of viruses), as well as mRNA encoded by the genomic DNA, and cDNA.

"Nucleic acid segment," "oligonucleotide segment" or "polynucleotide segment" refers to a portion of a larger polynucleotide molecule. The polynucleotide segment need not correspond to an encoded functional domain of a protein; however, in some instances the segment will encode a functional domain of a protein. A polynucleotide segment can be about 6 nucleotides or more in length (e.g., 6-20, 20-50, 50-100, 100-200, 200-300, 300-400 or more nucleotides in length). A stability-associated peptide segment can be encoded by a stability-associated polynucleotide segment, wherein the peptide segment promotes stability, function, or folding compared to a polypeptide lacking the peptide segment.

"Chimera" refers to a combination of at least two segments or domains of at least two different parent proteins or polypeptides. As appreciated by one of skill in the art, the segments need not actually come from each of the parents, as it is the particular sequence that is relevant, and not the physical nucleic acids or peptides themselves. For example, a chimeric fungal class I cellobiohydrolases (CBH I cellulases) will have at least two segments from two different parent CBH I polypeptides. The two segments are connected so as to result in a new polypeptide having cellobiohydrolase activity. In other words, a protein will not be a chimera if it has the identical sequence of either one of the full length parents. A chimeric polypeptide can comprise more than two segments from two different parent proteins. For example, there may be 2, 3, 4, 5-10, 10-20, or more parents for each final chimera or library of chimeras. The segment of each parent polypeptide can be very short or very long, the segments can range in length of contiguous amino acids from 1 to about 90%, 95%, 98%, or 99% of the entire length of the protein. In one embodiment, the minimum length is 10 amino acids, but may be 15, 20, 25, 30, 35, 40, 45, 50, 55, 60, 65, 70, 75, 80, 85, 90, 95, 100 or more amino acids in length. In one embodiment, a single crossover point is defined for two parents. The crossover location defines where one parent's amino acid segment will stop and where the next parent's amino acid segment will start. Thus, a simple chimera would only have one crossover location where the segment before that crossover location would belong to a first parent and the segment after that crossover location would belong to a second parent. In one embodiment, the chimera has more than one crossover location. For example, 2, 3, 4, 5, 6, 7, 8, 9, 10, 11-30, or more crossover locations. How these crossover locations are named and defined are both discussed below. In an embodiment where there are two crossover locations and two parents, there will be a first contiguous segment from a first parent, followed by a second contiguous segment from a second parent, followed by a third contiguous segment from the first parent or yet a different parent. Contiguous is meant to denote that there is nothing of significance interrupting the segments. These contiguous segments are connected to form a contiguous amino acid sequence. For example, a CBH I chimera from *C. thermophilium* (hereinafter "1") and *T. aurantiacus* (hereinafter "2"), with two crossovers at 49 and 94, could have the first 49 amino acids from 1, followed by the next 55 from 2, followed by the remainder of the amino acids from 1, all connected in one contiguous amino acid chain. Alternatively, the CBH I chimera could have the first 49 amino acids from 2, the next 55 from 1 and the remainder followed by 2. As appreciated by one of skill in the art, variants of chimeras exist as well as the exact sequences. Thus, not 100% of each segment need be present in the final chimera if it is a variant chimera. The amount that may be altered, either through additional residues or removal or alteration of residues will be defined as the term variant is defined. Of course, as understood by one of skill in the art, the above discussion applies not only to amino acids but also nucleic acids which encode for the amino acids.

"Conservative amino acid substitution" refers to the interchangeability of residues having similar side chains, and thus typically involves substitution of the amino acid in the polypeptide with amino acids within the same or similar defined class of amino acids. By way of example and not limitation, an amino acid with an aliphatic side chain may be substituted with another aliphatic amino acid, e.g., alanine, valine, leucine, isoleucine, and methionine; an amino acid with hydroxyl side chain is substituted with another amino acid with a hydroxyl side chain, e.g., serine and threonine; an amino acids having aromatic side chains is substituted with another amino acid having an aromatic side chain, e.g., phenylalanine, tyrosine, tryptophan, and histidine; an amino acid with a basic side chain is substituted with another amino acid with a basis side chain, e.g., lysine, arginine, and histidine; an amino acid with an acidic side chain is substituted with another amino acid with an acidic side chain, e.g., aspartic acid or glutamic acid; and a hydrophobic or hydrophilic amino acid is replaced with another hydrophobic or hydrophilic amino acid, respectively.

"Non-conservative substitution" refers to substitution of an amino acid in the polypeptide with an amino acid with significantly differing side chain properties. Non-conservative substitutions may use amino acids between, rather than within, the defined groups and affects (a) the structure of the peptide backbone in the area of the substitution (e.g., proline for glycine) (b) the charge or hydrophobicity, or (c) the bulk of the side chain. By way of example and not limitation, an exemplary non-conservative substitution can be an acidic amino acid substituted with a basic or aliphatic amino acid; an aromatic amino acid substituted with a small amino acid; and a hydrophilic amino acid substituted with a hydrophobic amino acid.

"Isolated polypeptide" refers to a polypeptide which is separated from other contaminants that naturally accompany it, e.g., protein, lipids, and polynucleotides. The term embraces polypeptides which have been removed or purified from their naturally-occurring environment or expression system (e.g., host cell or in vitro synthesis).

"Substantially pure polypeptide" refers to a composition in which the polypeptide species is the predominant species present (i.e., on a molar or weight basis it is more abundant than any other individual macromolecular species in the composition), and is generally a substantially purified composition when the object species comprises at least about 50 percent of the macromolecular species present by mole or % weight. Generally, a substantially pure polypeptide composition will comprise about 60% or more, about 70% or more, about 80% or more, about 90% or more, about 95% or more, and about 98% or more of all macromolecular species by mole or % weight present in the composition. In some embodiments, the object species is purified to essential homogeneity (i.e., contaminant species cannot be detected in the composition by conventional detection methods) wherein the composition consists essentially of a single macromolecular species. Solvent species, small molecules (<500 Daltons), and elemental ion species are not considered macromolecular species.

"Reference sequence" refers to a defined sequence used as a basis for a sequence comparison. A reference sequence may be a subset of a larger sequence, for example, a segment of a full-length gene or polypeptide sequence. Generally, a reference sequence can be at least 20 nucleotide or amino acid residues in length, at least 25 nucleotide or residues in length, at least 50 nucleotides or residues in length, or the full length of the nucleic acid or polypeptide. Since two polynucleotides or polypeptides may each (1) comprise a sequence (i.e., a portion of the complete sequence) that is similar between the two sequences, and (2) may further comprise a sequence that is divergent between the two sequences, sequence comparisons between two (or more) polynucleotides or polypeptides are typically performed by comparing sequences of the two polynucleotides or polypeptides over a "comparison window" to identify and compare local regions of sequence similarity.

"Sequence identity" means that two amino acid sequences are substantially identical (e.g., on an amino acid-by-amino acid basis) over a window of comparison. The term "sequence similarity" refers to similar amino acids that share the same biophysical characteristics. The term "percentage of sequence identity" or "percentage of sequence similarity" is calculated by comparing two optimally aligned sequences over the window of comparison, determining the number of positions at which the identical residues (or similar residues) occur in both polypeptide sequences to yield the number of matched positions, dividing the number of matched positions by the total number of positions in the window of comparison (i.e., the window size), and multiplying the result by 100 to yield the percentage of sequence identity (or percentage of sequence similarity). With regard to polynucleotide sequences, the terms sequence identity and sequence similarity have comparable meaning as described for protein sequences, with the term "percentage of sequence identity" indicating that two polynucleotide sequences are identical (on a nucleotide-by-nucleotide basis) over a window of comparison. As such, a percentage of polynucleotide sequence identity (or percentage of polynucleotide sequence similarity, e.g., for silent substitutions or other substitutions, based upon the analysis algorithm) also can be calculated. Maximum correspondence can be determined by using one of the sequence algorithms described herein (or other algorithms available to those of ordinary skill in the art) or by visual inspection.

As applied to polypeptides, the term substantial identity or substantial similarity means that two peptide sequences, when optimally aligned, such as by the programs BLAST, GAP or BESTFIT using default gap weights or by visual inspection, share sequence identity or sequence similarity. Similarly, as applied in the context of two nucleic acids, the term substantial identity or substantial similarity means that the two nucleic acid sequences, when optimally aligned, such as by the programs BLAST, GAP or BESTFIT using default gap weights (described elsewhere herein) or by visual inspection, share sequence identity or sequence similarity.

One example of an algorithm that is suitable for determining percent sequence identity or sequence similarity is the FASTA algorithm, which is described in Pearson, W. R. & Lipman, D. J., (1988) Proc. Natl. Acad. Sci. USA 85:2444. See also, W. R. Pearson, (1996) Methods Enzymology 266:227-258. Preferred parameters used in a FASTA alignment of DNA sequences to calculate percent identity or percent similarity are optimized, BL50 Matrix 15: −5, k-tuple=2; joining penalty=40, optimization=28; gap penalty −12, gap length penalty=−2; and width=16.

Another example of a useful algorithm is PILEUP. PILEUP creates a multiple sequence alignment from a group of related sequences using progressive, pairwise alignments to show relationship and percent sequence identity or percent sequence similarity. It also plots a tree or dendogram showing the clustering relationships used to create the alignment. PILEUP uses a simplification of the progressive alignment method of Feng & Doolittle, (1987) J. Mol. Evol. 35:351-360. The method used is similar to the method described by Higgins & Sharp, CABIOS 5:151-153, 1989. The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. Using PILEUP, a reference sequence is compared to other test sequences to determine the percent sequence identity (or percent sequence similarity) relationship using the following parameters: default gap weight (3.00), default gap length weight (0.10), and weighted end gaps. PILEUP can be obtained from the GCG sequence analysis software package, e.g., version 7.0 (Devereaux et al., (1984) Nuc. Acids Res. 12:387-395).

Another example of an algorithm that is suitable for multiple DNA and amino acid sequence alignments is the CLUSTALW program (Thompson, J. D. et al., (1994) Nuc. Acids Res. 22:4673-4680). CLUSTALW performs multiple pairwise comparisons between groups of sequences and assembles them into a multiple alignment based on sequence identity. Gap open and Gap extension penalties were 10 and 0.05 respectively. For amino acid alignments, the BLOSUM algorithm can be used as a protein weight matrix (Henikoff and Henikoff, (1992) Proc. Natl. Acad. Sci. USA 89:10915-10919).

"Functional" refers to a polypeptide which possesses either the native biological activity of the naturally-produced proteins of its type, or any specific desired activity, for example as judged by its ability to bind to ligand molecules or carry out an enzymatic reaction.

The disclosure describes a directed SCHEMA recombination library to generate cellobiohydrolase enzymes based on a particularly members of this enzyme family, and more particularly cellobiohydrolase I enzymes (e.g., C. thermophilum is parent "1" (SEQ ID NO:2), T. aurantiacus is parent "2" (SEQ ID NO:4), H. jecorina is parent "3" (SEQ ID NO:6), A. thermophilum is parent "4" (SEQ ID NO: 8) and T. emersonii is parent "5" (SEQ ID NO: 10)) SCHEMA is a computational based method for predicting which fragments of related proteins can be recombined without affecting the structural integrity of the protein (see, e.g., Meyer et al., (2003) Protein Sci., 12:1686-1693). This computational approached identified seven recombination points in the CBH I parental proteins, thereby allowing the formation of a library of CBH I chimera polypeptides, where each polypeptide comprises, for example, from two to eight segments. Chimeras with higher stability are identifiable by determining the additive contribution of each segment to the overall stability, either by use of linear regression of sequence-stability data, or by reliance on consensus analysis of the MSAs of folded versus unfolded proteins. SCHEMA recombination ensures that the chimeras retain biological function and exhibit high sequence diversity by conserving important functional residues while exchanging tolerant ones.

Thus, as illustrated by various embodiments herein, the disclosure provides CBH I polypeptides comprising a chimera of parental domains. In some embodiments, the polypeptide comprises a chimera having a plurality of domains from N- to C-terminus from different parental CBH II proteins: (segment 1)-(segment 2)-(segment 3)-(segment 4)-(segment 5)-(segment 6)-(segment 7)-(segment 8);

wherein segment 1 comprises amino acid residue from about 1 or from about 18 or 19 to about $x_1$ of SEQ ID NO:2 ("1"), SEQ ID NO:4 ("2"), SEQ ID NO:6 ("3"), SEQ ID NO:8 ("4"), or SEQ ID NO:10 ("5"); segment 2 comprises a sequence that is at least 50-100% identical to amino acid residue $x_1$ to about $x_2$ of SEQ ID NO:2 ("1"), SEQ ID NO:4 ("2"), SEQ ID NO:6 ("3"), SEQ ID NO:8 ("4"), or SEQ ID NO:10 ("5"); segment 3 comprises a sequence that is at least 50-100% identical to amino acid residue $x_2$ to about $x_3$ of SEQ ID NO:2 ("1"), SEQ ID NO:4 ("2"), SEQ ID NO:6 ("3"), SEQ ID NO:8 ("4"), or SEQ ID NO:10 ("5"); segment 4 comprises a sequence that is at least 50-100% identical to amino acid residue $x_3$ to about $x_4$ of SEQ ID NO:2 ("1"), SEQ ID NO:4 ("2"), SEQ ID NO:6 ("3"), SEQ ID NO:8 ("4"), or SEQ ID NO:10 ("5"); segment 5 comprises a sequence that is at least 50-100% identical to about amino acid residue $x_4$ to about $x_5$ of SEQ ID NO:2 ("1"), SEQ ID NO:4 ("2"), SEQ ID NO:6 ("3"), SEQ ID NO:8 ("4"), or SEQ ID NO:10 ("5"); segment 6 comprises a sequence that is at least 50-100% identical to amino acid residue $x_5$ to about $x_6$ of SEQ ID NO:2 ("1"), SEQ ID NO:4 ("2"), SEQ ID NO:6 ("3"), SEQ ID NO:8 ("4"), or SEQ ID NO:10 ("5"); segment 7 comprises a sequence that is at least 50-100% identical to amino acid residue $x_6$ to about $x_7$ of SEQ ID NO:2 ("1"), SEQ ID NO:4 ("2"), SEQ ID NO:6 ("3"), SEQ ID NO:8 ("4"), or SEQ ID NO:10 ("5"); and segment 8 comprises a sequence that is at least 50-100% identical to amino acid residue $x_7$ to about $x_8$ of SEQ ID NO:2 ("1"), SEQ ID NO:4 ("2"), SEQ ID NO:6 ("3"), SEQ ID NO:8 ("4"), or SEQ ID NO:10 ("5"):

wherein $x_1$ is residue 47, 48, 49, 50, 51, or 52 of SEQ ID NO:2, 4, 6, or 8, or residue 48, 49, 50, 51, 52 or 53 of SEQ ID NO:10; $x_2$ is residue 92, 93, 94 95, 96 or 97 of SEQ ID NO:2 or 10, or residue 91, 92, 93, 94, 95, or 96 of SEQ ID NO:4, 6, or 8; $x_3$ is residue 127, 128, 129, 130, 131 or 132 of SEQ ID NO:2, or residue 125, 126, 127, 128, 129 or 130 of SEQ ID NO:4 or 6, or residue 126, 127, 128, 129, 130 or 131 of SEQ ID NO:8, or residue 123, 124, 125, 126, 127 or 128 or SEQ ID NO:10; $x_4$ is residue 175, 176, 177, 178, 180 or 181 of SEQ ID NO:2, or residue 173, 174, 175, 176, 177 or 178 of SEQ ID NO:4 or SEQ ID NO:6, or residue 174, 175, 176, 177, 178 or 179 of SEQ ID NO:8, or 171, 172, 173, 174, 175, or 176 of SEQ ID NO:10; $x_5$ is 221, 222, 223, 224, 225, or 226 of SEQ ID NO:2, or residue 219, 220, 221, 222, 223 or 224 of SEQ ID NO:4 or SEQ ID NO:6, or residue 220, 221, 222, 223, 224 or 225 of SEQ ID NO:8, or 217, 218, 219, 220, 221 or 222 of SEQ ID NO:10; $x_6$ is residue 268, 269, 270, 271, 272 or 273 of SEQ ID NO:2, or residue 266, 267, 268, 269, 270 or 271 of SEQ ID NO:4 or SEQ ID NO:6, or residue 267, 268, 269, 270, 271 or 272 of SEQ ID NO:8, or 264, 265, 266, 267, 268 or 269 of SEQ ID NO:10; $x_7$ is residue 384, 385, 386, 387, 388 or 389 of SEQ ID NO:2, or residue 385, 386, 387, 388, 389 or 390 of SEQ ID NO:4, or residue 378, 379, 380, 381, 382 or 383 or SEQ ID NO:6, or residue 383, 384, 385, 386, 387 or 388 of SEQ ID NO:8 or 10; and $x_8$ is an amino acid residue corresponding to residue 454, of SEQ ID NO:2, residue 457 of SEQ ID NO:4, residue 458 of SEQ ID NO:6, residue 453 of SEQ ID NO:8, residue 455 of SEQ ID NO:10 or the C-terminus of the polypeptide having the sequence of SEQ ID NO:2, SEQ ID NO:4, SEQ ID NO:6, SEQ ID NO:8 or SEQ ID NO:10.

Using the foregoing domain references a number of chimeric structure were generated as set forth in Table 1.

TABLE 1

Total yeast-secreted MUL activity and $T_{50}$ values for disulfide-paired CBH I chimeras and underlying monomeras.

| Chimera | Total Secreted Activity (mol MUL/(L · s)) × $10^5$ | $T_{50}$ (° C.) |
| --- | --- | --- |
| 55515555 | 2.6 | 61.0 +/− 0.1 |
| 55555551 | 11.8 | 61.9 +/− 0.2 |
| 55515551 | 6.3 | 58.2 +/− 0.3 |
| 55525555 | 6.7 | 62.4 +/− 0.2 |
| 55555552 | 21.8 | 64.6 +/− 0.2 |
| 55525552 | 11.0 | 63.1 +/− 0.1 |
| 55555155 | 8.6 | 60.5 +/− 0.0 |
| 55555515 | 0.3 | NS |

TABLE 1-continued

Total yeast-secreted MUL activity and $T_{50}$ values for disulfide-paired CBH I chimeras and underlying monomeras.

| Chimera | Total Secreted Activity (mol MUL/(L · s)) × $10^5$ | $T_{50}$ (° C.) |
|---|---|---|
| 55555115 | 0.1 | NS |
| 55555255 | 14.1 | 63.2 +/− 0.5 |
| 55555525 | 1.0 | NS |
| 55555225 | 0.2 | NS |

$T_{50}$ value error bars represent extremes of 2 duplicate measurements, MUL activity values for a single measurement of a single culture, 300 μM MUL, 30-minute incubation at 45° C. NS indicates insufficient secretion for $T_{50}$ measurement.

Referring to the table above, each digit refers to a domain/segment of a chimeric CBH I polypeptide. The number denotes the parental strand of the domain/segment. For example, a chimeric CBH I polypeptide having the sequence 12111131, indicates that the polypeptide comprises a sequence from the N-terminus to the C-terminus of: amino acids from about 1 to $x_1$ of SEQ ID NO:2 ("1") linked to amino acids from about $x_1$ to $x_2$ of SEQ ID NO:4 ("2") linked to amino acids from about $x_2$ to about $x_3$ of SEQ ID NO:2 linked to amino acids from about $x_3$ to about $x_4$ of SEQ ID NO:2 linked to amino acids from about $x_4$ to about $x_5$ of SEQ ID NO:2 linked to amino acids from about $x_5$ to about $x_6$ of SEQ ID NO:2 linked to amino acids from about $x_6$ to $x_7$ of SEQ ID NO:6 ("3") linked to amino acids from about $x_7$ to $x_8$ (e.g., the C-terminus) of SEQ ID NO:2.

TABLE 2

Total yeast-secreted MUL activity (mol MUL/(L · s)) × $10^5$ and $T_{50}$ values for B7P5 chimeras and corresponding B7P*5 substituted chimeras.

| B7P5 Chimera | Total Secreted Activity | $T_{50}$ (° C.) | B7P*5 Chimera | Total Secreted Activity | $T_{50}$ (° C.) |
|---|---|---|---|---|---|
| 55153552 | 33.2 | 64.3 +/− 0.0 | 551535*52 | 42.2 | 65.7 +/− 0.2 |
| 12153252 | 6.4 | 64.7 +/− 0.2 | 121532*52 | 10.6 | 66.0 +/− 0.0 |
| 25152252 | 22.2 | 65.0 +/− 0.1 | 251522*52 | 28.7 | 66.8 +/− 0.1 |
| 12152252 | 10.2 | 65.3 +/− 0.1 | 121522*52 | 17.7 | 66.9 +/− 0.1 |
| 55152252 | 19.6 | 66.3 +/− 1.0 | 551522*52 | 34.0 | 66.9 +/− 0.1 |

$T_{50}$ value error bars represent extremes of 2 duplicate measurements, MUL activity values for a single measurement of a single culture, 300 μM MUL, 30-minute incubation at 45° C.

In some embodiments, the polypeptide has improved thermostability compared to a wild-type polypeptide of SEQ ID NO:2, 4, 6, 8 or 10. The activity of the polypeptide can be measured with any one or combination of substrates as described in the examples. As will be apparent to the skilled artisan, other compounds within the class of compounds exemplified by those discussed in the examples can be tested and used.

In some embodiments, the polypeptide can comprise various changes to the amino acid sequence with respect to a reference sequence. The changes can be a substitution, deletion, or insertion of one or more amino acids. Where the change is a substitution, the change can be a conservative or a non-conservative substitution. Accordingly a chimera may comprise a combination of conservative and non-conservative substitutions.

Thus, in some embodiments, the polypeptides can comprise a general structure from N-terminus to C-terminus: (segment 1)-(segment 2)-(segment 3)-(segment 4)-(segment 5)-(segment 6)-(segment 7)-(segment 8), wherein segment 1 comprises amino acid residue from about 1 or from about 18 or 19 to about $x_1$ of SEQ ID NO:2 ("1"), SEQ ID NO:4 ("2"), SEQ ID NO:6 ("3"), SEQ ID NO:8 ("4"), or SEQ ID NO:10 ("5") and having 1-10 conservative amino acid substitutions; segment 2 is from about amino acid residue $x_1$ to about $x_2$ of SEQ ID NO:2 ("1"), SEQ ID NO:4 ("2"), SEQ ID NO:6 ("3"), SEQ ID NO:8 ("4"), or SEQ ID NO:10 ("5") and having about 1-10 conservative amino acid substitutions; segment 3 is from about amino acid residue $x_2$ to about $x_3$ of SEQ ID NO:2 ("1"), SEQ ID NO:4 ("2"), SEQ ID NO:6 ("3"), SEQ ID NO:8 ("4"), or SEQ ID NO:10 ("5") and having about 1-10 conservative amino acid substitutions; segment 4 is from about amino acid residue $x_3$ to about $x_4$ of SEQ ID NO:2 ("1"), SEQ ID NO:4 ("2"), SEQ ID NO:6 ("3"), SEQ ID NO:8 ("4"), or SEQ ID NO:10 ("5") and having about 1-10 conservative amino acid substitutions; segment 5 is from about amino acid residue $x_4$ to about $x_5$ of SEQ ID NO:2 ("1"), SEQ ID NO:4 ("2"), SEQ ID NO:6 ("3"), SEQ ID NO:8 ("4"), or SEQ ID NO:10 ("5") and having about 1-10 conservative amino acid substitutions; segment 6 is from about amino acid residue $x_5$ to about $x_6$ of SEQ ID NO:2 ("1"), SEQ ID NO:4 ("2"), SEQ ID NO:6 ("3"), SEQ ID NO:8 ("4"), or SEQ ID NO:10 ("5") and having about 1-10 conservative amino acid substitutions; segment 7 is from about amino acid residue $x_6$ to about $x_7$ of SEQ ID NO:2 ("1"), SEQ ID NO:4 ("2"), SEQ ID NO:6 ("3"), SEQ ID NO:8 ("4"), or SEQ ID NO:10 ("5") and having about 1-10 conservative amino acid substitutions; and segment 8 is from about amino acid residue $x_7$ to about $x_8$ of SEQ ID NO:2 ("1"), SEQ ID NO:4 ("2"), SEQ ID NO:6 ("3"), SEQ ID NO:8 ("4"), or SEQ ID NO:10 ("5") and having about 1-10 conservative amino acid substitutions;

wherein $x_1$ is residue 47, 48, 49, 50, 51, or 52 of SEQ ID NO:2, 4, 6, or 8, or residue 48, 49, 50, 51, 52 or 53 of SEQ ID NO:10; $x_2$ is residue 92, 93, 94 95, 96 or 97 of SEQ ID NO:2 or 10, or residue 91, 92, 93, 94, 95, or 96 of SEQ ID NO:4, 6, or 8; $x_3$ is residue 127, 128, 129, 130, 131 or 132 of SEQ ID NO:2, or residue 125, 126, 127, 128, 129 or 130 of SEQ ID NO:4 or 6, or residue 126, 127, 128, 129, 130 or 131 of SEQ ID NO:8, or residue 123, 124, 125, 126, 127 or 128 of SEQ ID NO:10; $x_4$ is residue 175, 176, 177, 178, 180 or 181 of SEQ ID NO:2, or residue 173, 174, 175, 176, 177 or 178 of SEQ ID NO:4 or SEQ ID NO:6, or residue 174, 175, 176, 177, 178 or 179 of SEQ ID NO:8, or 171, 172, 173, 174, 175, or 176 of SEQ ID NO:10; $x_5$ is 221, 222, 223, 224, 225, or 226 of SEQ ID NO:2, or residue 219, 220, 221, 222, 223 or 224 of SEQ ID NO:4 or SEQ ID NO:6, or residue 220, 221, 222, 223, 224 or 225 of SEQ ID NO:8, or 217, 218, 219, 220, 221 or 222 of SEQ ID NO:10; $x_6$ is residue 268, 269, 270, 271, 272 or 273 of SEQ ID NO:2, or residue 266, 267, 268, 269, 270 or 271 of SEQ ID NO:4 or SEQ ID NO:6, or residue 267, 268, 269, 270, 271 or 272 of SEQ ID NO:8, or 264, 265, 266, 267, 268 or 269 of SEQ ID NO:10; $x_7$ is residue 384, 385, 386, 387, 388 or 389 of SEQ ID NO:2, or residue 385, 386, 387, 388, 389 or 390 of SEQ ID NO:4, or residue 378, 379, 380, 381, 382 or 383 or SEQ ID NO:6, or residue 383, 384, 385, 386, 387 or 388 of SEQ ID NO:8 or 10; and $x_8$ is an amino acid residue corresponding to residue 454, of SEQ ID NO:2, residue 457 of SEQ ID NO:4, residue 458 of SEQ ID NO:6, residue 453 of SEQ ID NO:8, residue 455 of SEQ ID NO:10 or the C-terminus of the polypeptide having the sequence of SEQ ID NO:2, SEQ ID NO:4, SEQ ID NO:6, SEQ ID NO:8 or SEQ ID NO:10, wherein the chimeric polypeptide has cellobiohydrolase activity and improved thermostability and/or pH stability compared to a CBH I polypeptide comprising SEQ ID NO:2, 4, 6, 8 or 10.

In some embodiments, the number of substitutions can be 2, 3, 4, 5, 6, 8, 9, or 10, or more amino acid substitutions (e.g., 10-20, 21-30, 31-40 and the like amino acid substitutions).

In some embodiments, the functional chimera polypeptides can have cellobiohydrolase activity along with increased thermostability, such as for a defined substrate discussed in the Examples, and also have a level of amino acid sequence identity to a reference cellobiohydrolase, or segments thereof. The reference enzyme or segment, can be that of a wild-type (e.g., naturally occurring) or an engineered enzyme.

In some embodiments, each segment of the chimeric polypeptide can have at least 60%, 70%, 80%, 90%, 95%, 96%, 97%, 98%, or 99% or more sequence identity as compared to the reference segment indicated for each of the (segment 1), (segment 2), (segment 3), (segment 4)-(segment 5), (segment 6), (segment 7), and (segment 8) of SEQ ID NO:2, SEQ ID NO:4, SEQ ID NO:6, SEQ ID NO:8, or SEQ ID NO:10.

In some embodiments, the polypeptide variants can have improved thermostability compared to the enzyme activity of the wild-type polypeptide of SEQ ID NO:2, 4, 6, 8 or 10.

The chimeric enzymes described herein may be prepared in various forms, such as lysates, crude extracts, or isolated preparations. The polypeptides can be dissolved in suitable solutions; formulated as powders, such as an acetone powder (with or without stabilizers); or be prepared as lyophilizates. In some embodiments, the polypeptide can be an isolated polypeptide.

In some embodiments, the polypeptides can be in the form of arrays. The enzymes may be in a soluble form, for example, as solutions in the wells of microtitre plates, or immobilized onto a substrate. The substrate can be a solid substrate or a porous substrate (e.g., membrane), which can be composed of organic polymers such as polystyrene, polyethylene, polypropylene, polyfluoroethylene, polyethyleneoxy, and polyacrylamide, as well as co-polymers and grafts thereof. A solid support can also be inorganic, such as glass, silica, controlled pore glass (CPG), reverse phase silica or metal, such as gold or platinum. The configuration of a substrate can be in the form of beads, spheres, particles, granules, a gel, a membrane or a surface. Surfaces can be planar, substantially planar, or non-planar. Solid supports can be porous or non-porous, and can have swelling or non-swelling characteristics. A solid support can be configured in the form of a well, depression, or other container, vessel, feature, or location. A plurality of supports can be configured on an array at various locations, addressable for robotic delivery of reagents, or by detection methods and/or instruments.

The disclosure also provides polynucleotides encoding the engineered CBH I polypeptides disclosed herein. The polynucleotides may be operatively linked to one or more heterologous regulatory or control sequences that control gene expression to create a recombinant polynucleotide capable of expressing the polypeptide. Expression constructs containing a heterologous polynucleotide encoding the CBH I chimera can be introduced into appropriate host cells to express the polypeptide.

Given the knowledge of specific sequences of the CBH II chimera enzymes (e.g., the segment structure of the chimeric CBH II), the polynucleotide sequences will be apparent form the amino acid sequence of the engineered CBH II chimera enzymes to one of skill in the art and with reference to the polypeptide sequences and nucleic acid sequence described herein. The knowledge of the codons corresponding to various amino acids coupled with the knowledge of the amino acid sequence of the polypeptides allows those skilled in the art to make different polynucleotides encoding the polypeptides of the disclosure. Thus, the disclosure contemplates each and every possible variation of the polynucleotides that could be made by selecting combinations based on possible codon choices, and all such variations are to be considered specifically disclosed for any of the polypeptides described herein.

In some embodiments, the polynucleotides encode the polypeptides described herein but have about 80% or more sequence identity, about 85% or more sequence identity, about 90% or more sequence identity, about 91% or more sequence identity, about 92% or more sequence identity, about 93% or more sequence identity, about 94% or more sequence identity, about 95% or more sequence identity, about 96% or more sequence identity, about 97% or more sequence identity, about 98% or more sequence identity, or about 99% or more sequence identity at the nucleotide level to a reference polynucleotide encoding the CBH I chimera polypeptides.

In some embodiments, the isolated polynucleotides encoding the polypeptides may be manipulated in a variety of ways to provide for expression of the polypeptide. Manipulation of the isolated polynucleotide prior to its insertion into a vector may be desirable or necessary depending on the expression vector. The techniques for modifying polynucleotides and nucleic acid sequences utilizing recombinant DNA methods are well known in the art. Guidance is provided in Sambrook et al., 2001, Molecular Cloning: A Laboratory Manual, 3rd Ed., Cold Spring Harbor Laboratory Press; and Current Protocols in Molecular Biology, Ausubel. F. ed., Greene Pub. Associates, 1998, updates to 2007.

In some embodiments, the polynucleotides are operatively linked to control sequences for the expression of the polynucleotides and/or polypeptides. In some embodiments, the control sequence may be an appropriate promoter sequence, which can be obtained from genes encoding extracellular or intracellular polypeptides, either homologous or heterologous to the host cell. For bacterial host cells, suitable promoters for directing transcription of the nucleic acid constructs of the present disclosure, include the promoters obtained from the E. coli lac operon, Bacillus subtilis xylA and xylB genes, Bacillus megatarium xylose utilization genes (e.g., Rygus et al., (1991) Appl. Microbiol. Biotechnol. 35:594-599; Meinhardt et al., (1989) Appl. Microbiol. Biotechnol. 30:343-350), prokaryotic beta-lactamase gene (Villa-Kamaroff et al., (1978) Proc. Natl Acad. Sci. USA 75: 3727-3731), as well as the tac promoter (DeBoer et al., (1983) Proc. Natl Acad. Sci. USA 80: 21-25). Various suitable promoters are described in "Useful proteins from recombinant bacteria" in Scientific American, 1980, 242:74-94; and in Sambrook et al., supra.

In some embodiments, the control sequence may also be a suitable transcription terminator sequence, a sequence recognized by a host cell to terminate transcription. The terminator sequence is operably linked to the 3' terminus of the nucleic acid sequence encoding the polypeptide. Any terminator which is functional in the host cell of choice may be used.

In some embodiments, the control sequence may also be a suitable leader sequence, a nontranslated region of an mRNA that is important for translation by the host cell. The leader sequence is operably linked to the 5' terminus of the nucleic acid sequence encoding the polypeptide. Any leader sequence that is functional in the host cell of choice may be used.

In some embodiments, the control sequence may also be a signal peptide coding region that codes for an amino acid sequence linked to the amino terminus of a polypeptide and directs the encoded polypeptide into the cell's secretory pathway. The 5' end of the coding sequence of the nucleic acid sequence may inherently contain a signal peptide coding region naturally linked in translation reading frame with the segment of the coding region that encodes the secreted polypeptide. For example, SEQ ID NO:2, 4, 6, 8, and 10 each have signal peptide sequences (e.g., from amino acid 1 to 17 (i.e., cleaved after amino acid 17 of SEQ ID NO:4, 6, and 8) or to amino acid 18 (i.e., cleaved after amino acid 18 of SEQ ID NO:1 and 10). A mature polypeptide of the disclosure, a mature chimera polypeptide will lack the signal peptide domain (e.g., the first 1-18 amino acids of SEQ ID NO:2, 4, 6, 8, or 10). Alternatively, the 5' end of the coding sequence may contain a signal peptide coding region that is foreign to the coding sequence. The foreign signal peptide coding region may be required where the coding sequence does not naturally contain a signal peptide coding region. Effective signal peptide coding regions for bacterial host cells can be the signal peptide coding regions obtained from the genes for *Bacillus* NCIB 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Further signal peptides are described by Simonen and Palva, (1993) Microbiol Rev 57: 109-137.

Furthermore, the C-terminal end of the chimera of the disclosure may comprise a carbohydrate binding module (CBM). The CBM may be contiguous with the C-terminal domain of a chimera or may be attached via a linker. Furthermore, the CBH may be heterologous to the final domain of the chimera of the disclosure.

The disclosure is further directed to a recombinant expression vector comprising a polynucleotide encoding an engineered CBH I chimera polypeptide, and one or more expression regulating regions such as a promoter and a terminator, a replication origin, etc., depending on the type of hosts into which they are to be introduced. In creating the expression vector, the coding sequence is located in the vector so that the coding sequence is operably linked with the appropriate control sequences for expression.

The recombinant expression vector may be any vector (e.g., a plasmid or virus), which can be conveniently subjected to recombinant DNA procedures and can bring about the expression of the polynucleotide sequence. The choice of the vector will typically depend on the compatibility of the vector with the host cell into which the vector is to be introduced. The vectors may be linear or closed circular plasmids.

The expression vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon, may be used.

In some embodiments, the expression vector of the disclosure contains one or more selectable markers, which permit easy selection of transformed cells. A selectable marker is a gene the product of which provides for biocide or viral resistance, resistance to heavy metals, prototrophy to auxotrophs, and the like. Examples of bacterial selectable markers are the dal genes from *Bacillus subtilis* or *Bacillus licheniformis*, or markers, which confer antibiotic resistance such as ampicillin, kanamycin, chloramphenicol or tetracycline resistance. Other useful markers will be apparent to the skilled artisan.

In another embodiment, the disclosure provides a host cell comprising a polynucleotide encoding a CBH I chimera polypeptide, the polynucleotide being operatively linked to one or more control sequences for expression of the polypeptide in the host cell. Host cells for use in expressing the polypeptides encoded by the expression vectors of the disclosure are well known in the art and include, but are not limited to, bacterial cells, such as *E. coli* and *Bacillus megaterium*; eukaryotic cells, such as yeast cells, CHO cells and the like, insect cells such as *Drosophila* S2 and *Spodoptera* Sf9 cells; animal cells such as CHO, COS, BHK, 293, and Bowes melanoma cells; and plant cells. Other suitable host cells will be apparent to the skilled artisan. Appropriate culture mediums and growth conditions for the above-described host cells are well known in the art.

The CBH I chimera polypeptides of the disclosure can be made by using methods described herein. Polynucleotides can be synthesized by recombinant techniques, such as that provided in Sambrook et al., 2001, Molecular Cloning: A Laboratory Manual, 3rd Ed., Cold Spring Harbor Laboratory Press; and Current Protocols in Molecular Biology, Ausubel. F. ed., Greene Pub. Associates, 1998, updates to 2007. Polynucleotides encoding the enzymes, or the primers for amplification can also be prepared by standard solid-phase methods, according to known synthetic methods, for example using phosphoramidite method described by Beaucage et al., (1981) Tet Lett 22:1859-69, or the method described by Matthes et al., (1984) EMBO J. 3:801-05, e.g., as it is typically practiced in automated synthetic methods. In addition, essentially any nucleic acid can be obtained from any of a variety of commercial sources, such as The Midland Certified Reagent Company, Midland, Tex. The Great American Gene Company, Ramona, Calif., ExpressGen Inc. Chicago, Ill. Operon Technologies Inc., Alameda, Calif., and many others.

Engineered enzymes expressed in a host cell can be recovered from the cells and or the culture medium using any one or more of the well known techniques for protein purification, including, among others, lysozyme treatment, sonication, filtration, salting-out, ultra-centrifugation, chromatography, and affinity separation (e.g., substrate bound antibodies). Suitable solutions for lysing and the high efficiency extraction of proteins from bacteria, such as *E. coli*, are commercially available under the trade name CelLytic B™ from Sigma-Aldrich of St. Louis Mo.

Chromatographic techniques for isolation of the polypeptides include, among others, reverse phase chromatography high performance liquid chromatography, ion exchange chromatography, gel electrophoresis, and affinity chromatography. Conditions for purifying a particular enzyme will depend, in part, on factors such as net charge, hydrophobicity, hydrophilicity, molecular weight, molecular shape, etc., and will be apparent to those having skill in the art.

Descriptions of SCHEMA directed recombination and synthesis of chimeric polypeptides are described in the examples herein, as well as in Otey et al., (2006), PLoS Biol. 4(5):e112; Meyer et al., (2003) Protein Sci., 12:1686-1693; U.S. patent application Ser. No. 12/024,515, filed Feb. 1, 2008; and U.S. patent application Ser. No. 12/027,885, filed Feb. 7, 2008; such references incorporated herein by reference in their entirety.

As discussed above, the polypeptide can be used in a variety of applications, such as, among others, biofuel generation, cellulose breakdown and the like.

For example, in one embodiment, a method for processing cellulose is provided. The method includes culturing a recombinant microorganism as provided herein that expresses a chimeric polypeptide of the disclosure in the presence of a suitable cellulose substrate and under conditions suitable for the catalysis by the chimeric polypeptide of the cellulose.

In yet another embodiment, a substantially purified chimeric polypeptide of the disclosure is contacted with a cellulose substrate under conditions that allow for the chimeric polypeptide to degrade the cellulose. In one embodiment, the conditions include temperatures from about 35-65° C.

As previously discussed, general texts which describe molecular biological techniques useful herein, including the use of vectors, promoters and many other relevant topics, include Berger and Kimmel, Guide to Molecular Cloning Techniques, Methods in Enzymology Volume 152, (Academic Press, Inc., San Diego, Calif.; Sambrook et al., Molecular Cloning—A Laboratory Manual, 2d ed., Vol. 1-3, Cold Spring Harbor Laboratory, Cold Spring Harbor, N.Y., 1989; and Current Protocols in Molecular Biology, F. M. Ausubel et al., eds., Current Protocols, a joint venture between Greene Publishing Associates, Inc. and John Wiley & Sons, Inc., (supplemented through 1999). Examples of protocols sufficient to direct persons of skill through in vitro amplification methods, including the polymerase chain reaction (PCR), the ligase chain reaction (LCR), Q-replicase amplification and other RNA polymerase mediated techniques (e.g., NASBA), e.g., for the production of the homologous nucleic acids of the disclosure are found in Berger, Sambrook, and Ausubel, as well as in Mullis et al. (1987) U.S. Pat. No. 4,683,202; Innis et al., eds. (1990) PCR Protocols: A Guide to Methods and Applications (Academic Press Inc. San Diego, Calif.) ("Innis"); Arnheim & Levinson (Oct. 1, 1990) C&EN 36-47; The Journal Of NIH Research (1991) 3: 81-94; Kwoh et al. (1989) Proc. Natl. Acad. Sci. USA 86: 1173; Guatelli et al. (1990) Proc. Nat'l. Acad. Sci. USA 87: 1874; Lomell et al. (1989) J. Clin. Chem 35: 1826; Landegren et al. (1988) Science 241: 1077-1080; Van Brunt (1990) Biotechnology 8: 291-294; Wu and Wallace (1989) Gene 4:560; Barringer et al. (1990) Gene 89:117; and Sooknanan and Malek (1995) Biotechnology 13: 563-564. Improved methods for cloning in vitro amplified nucleic acids are described in Wallace et al., U.S. Pat. No. 5,426,039. Improved methods for amplifying large nucleic acids by PCR are summarized in Cheng et al. (1994) Nature 369: 684-685 and the references cited therein, in which PCR amplicons of up to 40 kb are generated. One of skill will appreciate that essentially any RNA can be converted into a double stranded DNA suitable for restriction digestion, PCR expansion and sequencing using reverse transcriptase and a polymerase. See, e.g., Ausubel, Sambrook and Berger, all supra.

Appropriate culture conditions include, for example, culture medium pH, ionic strength, nutritive content, etc.; temperature; oxygen/$CO_2$/nitrogen content; humidity; and other culture conditions that permit production of the compound by the host microorganism, i.e., by the metabolic action of the microorganism. Appropriate culture conditions are well known for microorganisms that can serve as host cells.

The following examples are meant to further explain, but not limited the foregoing disclosure or the appended claims.

EXAMPLES

Parent and chimeric genes encoding CBH I enzymes were cloned into yeast expression vector YEp352/PGK91-1-αss and transformed into expression strain YDR483W. Parent CBH I genes featured native codon usage and were synthesized by DNA 2.0 (Menlo Park, Calif.). Five mL synthetic dextrose casamino acids (SDCAA) media starter cultures were grown overnight at 30° C. with shaking at 225 rpm, expanded into 40 mL of yeast peptone dextrose (YPD) medium and incubated for 48 hours. Culture supernatants were brought to 1 mM phenylmethylsulfonylfluoride (PMSF) and 0.02% $NaN_3$.

Total yeast-secreted CBH I activity toward the soluble substrate 4-methylumbelliferyl lactopyranoside (MUL) was determined by adding 125 µL of culture supernatant to 25 µL of 1.8 mM MUL (Sigma) dissolved in 750 mM sodium acetate, pH 4.8, incubating at 45° C. for 30 minutes and quenching with 150 µL 1 M $Na_2CO_3$. MUL hydrolysis rates were determined by using a microplate reader to measure sample fluorescence with excitation at 365 nm and emission at 445 nm and comparing values to a standard curve prepared with 4-methylumbelliferone (Sigma).

The $T_{50}$ value is defined as the temperature at which a 10-minute incubation in the absence of substrate causes loss of one-half of the activity, measured after reaction with MUL substrate, relative to a 100% activity reference sample that does not undergo the incubation. For $T_{50}$ assays, culture supernatants were diluted using a supernatant from a negative control YPD yeast culture not containing secreted cellulase so that approximately equivalent MUL hydrolysis rates of $1.6*10^{-5}$ mol/L/s were obtained for samples not incubated for thermal denaturation. These diluted samples were adjusted to 1 mM DTT and 125 mM sodium acetate, pH 4.8. Aliquots of 125 µL were incubated for 10 minutes in a water bath across a range of temperatures bracketing the $T_{50}$ value. Water bath temperatures were measured using two different alcohol thermometers and observed to be consistent within 0.1° C. After cooling, 25 µL of 1.8 mM MUL in 50 mM sodium acetate, pH 4.8 was added to the incubated sample and an unheated sample, and these were incubated in a 45° C. water bath for 90 minutes. MUL hydrolysis was determined as above, and the $T_{50}$ value was calculated by linear interpolation of data using Microsoft Excel. A representative $T_{50}$ data set is provided in Table 3.

TABLE 3

Representative T$_{50}$ data for parent 1 (*C. ther*) into parent 5 (*T. emer*) monomeras.

| Ten Min Inc. Temp (° C.) | P5-*T. emer* | P1-*C. ther* | 15555555 | 51555555 | 55155555 | 55515555 | 55551555 | 55555155 | 55555551 |
|---|---|---|---|---|---|---|---|---|---|
| DAY 1 DATA | | | | | | | | | |
| No Incubation | 1 | 1 | 1 | 1 | 1 | 1 | 1 | 1 | 1 |
| 60 C. | 0.83 | 0.50 | 0.88 | 0.79 | 0.97 | 0.65 | 0.82 | 0.66 | 0.74 |
| 62.5 C. | 0.60 | 0.10 | 0.76 | 0.36 | 0.78 | 0.30 | 0.38 | 0.07 | 0.38 |
| 65 C. | 0.11 | 0.01 | 0.32 | 0.04 | 0.40 | 0.04 | 0.00 | 0.00 | 0.06 |
| T50 fit value | 62.6 | 59.5 | 63.9 | 61.9 | 64.4 | 61.1 | 61.9 | 60.6 | 61.7 |
| DAY 2 DATA | | | | | | | | | |
| No Incubation | 1 | 1 | 1 | 1 | 1 | 1 | 1 | 1 | 1 |
| 60 C. | 0.86 | 0.55 | 0.95 | 0.79 | 0.97 | 0.74 | 0.84 | 0.68 | 0.76 |
| 62.5 C. | 0.64 | 0.17 | 0.76 | 0.35 | 0.90 | 0.13 | 0.45 | 0.05 | 0.47 |
| 65 C. | 0.12 | 0.02 | 0.26 | 0.07 | 0.29 | 0.00 | 0.06 | 0.00 | 0.06 |
| T50 fit value | 63.0 | 60.1 | 63.9 | 61.9 | 64.1 | 61.0 | 62.2 | 60.6 | 62.1 |

Decimal values for each temperature point represent monomera activity retained relative to no preincubation after 10 minute preincubation at given temperature. Data are given for experiments performed on two consecutive days. T$_{50}$ fit values obtained using Microsoft Excel. T$_{50}$ values for parent 1 monomeras appear in FIG. 3. T$_{50}$ value given for *T. emersonii* (parent 5) is calculated based on average of the two below replicates and six additional T$_{50}$ measurements. 55555515 monomera secretion was too low to permit T$_{50}$ measurement.

To determine total yeast-secreted CBH I activity toward solid cellulose, 500 µL of yeast culture supernatant was incubated with 500 µL of 120 mg/mL Lattice NT microcrystalline cellulose (FMC) in 50 mM sodium acetate, pH 4.8, for 1 hour at 4° C. in a thermal block with shaking at 1000 rpm. Samples were centrifuged at 3000 rcf for 3 minutes and washed with 1 mL of ice cold 50 mM sodium acetate, pH 4.8, containing 1 mg/mL BSA. Solid cellulose with bound CBH I was resuspended in 1 mL of same buffer, incubated with shaking at 37° C. for 90 minutes, and the amount of reducing sugar in the reaction supernatant was determined by Nelson-Somogyi assay.

Ni$^{2+}$ affinity-isolated CBH I sample preparation, protein concentration measurement and SDS-PAGE analyses were performed. Post-Ni$^{2+}$ isolation CBH I yield estimates range from 500 µg/L culture for the poorly-secreted *T. aurantiacus* parent CBH I to between 5 and 10 mg/L for the *T. emersonii* parent CBH I and most highly secreted CBH I chimeras. CBH I solid cellulose temperature activity profiles were obtained by assuming that all protein in the affinity-isolated CBH I samples was fully active CBH I and adding 4 µg to 270 µL of 50 mM sodium acetate, pH 4.8 containing 60 mg/mL Lattice NT cellulose. After incubation for 16 hours in a water bath at the temperature of interest, supernatant reducing sugar was determined by Nelson-Somogyi assay.

For *T. emersonii* CBH I circular dichroism and half-life t$_{1/2}$ thermostability comparison experiments, metal affinity-isolated CBH I samples were treated as 100% fully active CBH I, and enzyme, substrate and buffer conditions were used (see, e.g., Voutilainen et al., Protein Eng Des Sel. 23: 69-79, 2010). Half-life assay samples in which CBH I was supplied by addition of culture supernatants received supernatant containing MUL-hydrolyzing CBH I activity approximately equal to that added to the assays performed with affinity-isolated CBH I. CBH I deglycosylation was performed using PNGaseF (New England Biolabs) per the manufacturer's instructions with a CBH I concentration of 100 µg/mL. CBH I secretion culturing of the hyperglycosylating yeast strain was performed as above with the exception that overnight starter cultures were grown in synthetic dropout—Uracil media prior to expansion into YPD.

Parent Fungal CBH I Enzymes.

Figure 7:
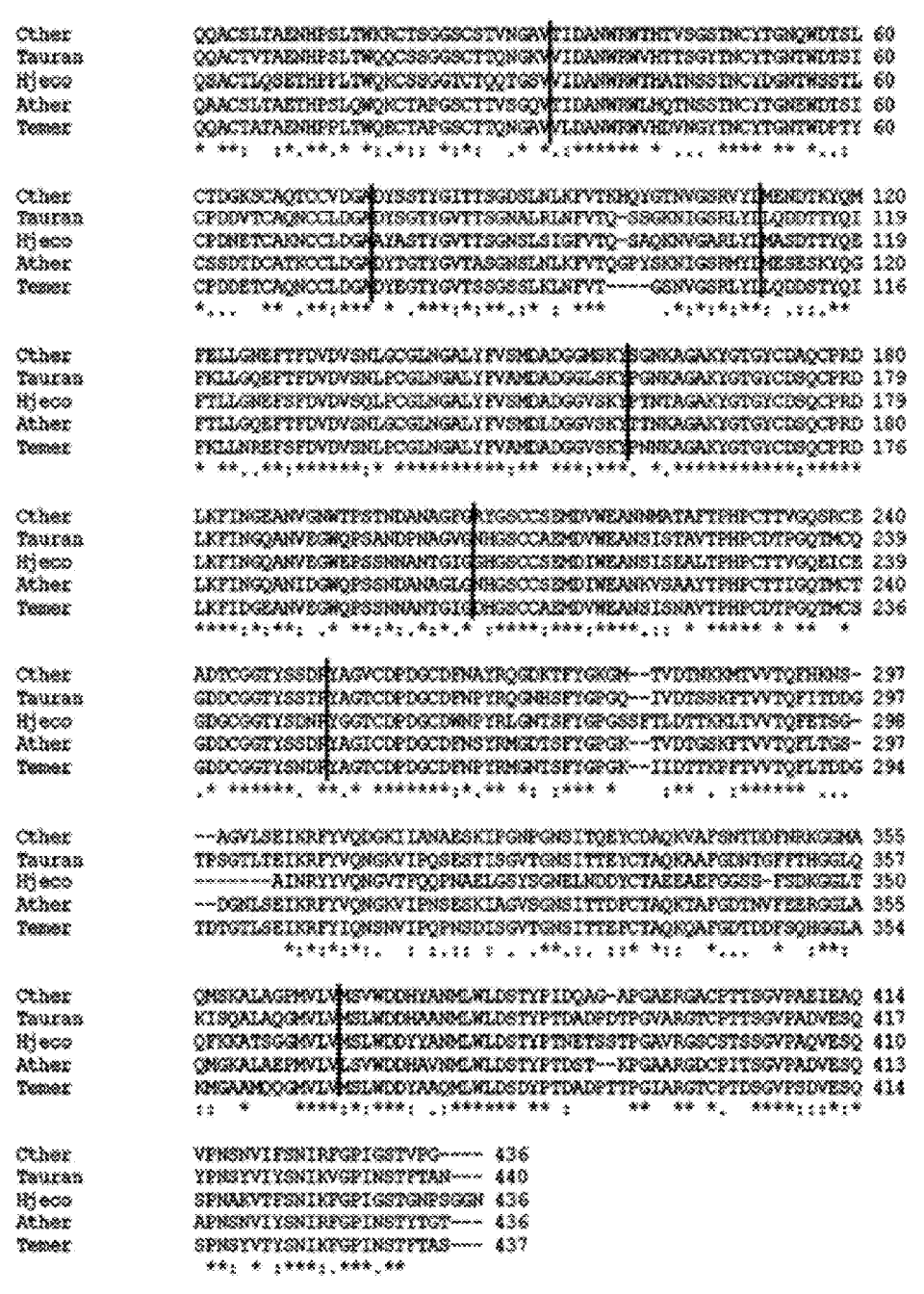

Four of the five CBH I recombination parents, from the filamentous fungi *Chaetomium thermophilum* (parent 1 (P1)), *Thermoascus aurantiacus* (P2), *Hypocrea jecorina* (P3) and *Acremonium thermophilum* (P4), were chosen on the basis of their having been overexpressed from the popular industrial cellulase secretion host *Trichoderma reesei* (teleomorph *H. jecorina*), which is important for industrial applications. The fifth CBH I (P5), from the thermophilic fungus *T. emersonii*, was included by virtue of its reported high thermostability. To eliminate the possibility of generating unpaired Cys residues upon recombination, residues G4 and A72 in the *T. emersonii* and *T. aurantiacus* CBH Is were changed to Cys (see SEQ ID NO:12 and 15), so that each parent CBH I catalytic domain contained 10 disulfide bonds. A sequence alignment of the five parent catalytic domains appears in FIG. 7, and the catalytic domain pairwise sequence identities are as follows:

Sequences (11:12) Aligned. Score: 69
Sequences (11:13) Aligned. Score: 61
Sequences (11:14) Aligned. Score: 71
Sequences (11:15) Aligned. Score: 64
Sequences (12:13) Aligned. Score: 66
Sequences (12:14) Aligned. Score: 73
Sequences (12:15) Aligned. Score: 81
Sequences (13:14) Aligned. Score: 63
Sequences (13:15) Aligned. Score: 66
Sequences (14:15) Aligned. Score: 70

The *T. emersonii* and *T. aurantiacus* CBH Is, which do not contain carbohydrate binding modules (CBM), were appended with the C-terminal linker and CBM from the *H. jecorina* CBH I, mimicking a construction previously used for heterologous expression of the *T. aurantiacus* CBH I. The *C. thermophilum*, *H. jecorina* and *A. thermophilum* parent genes featured their respective wild type linkers and CBMs. The sequences for all of the CBH I parents are provided in SEQ ID NOs: 11-15.

Figure 8:
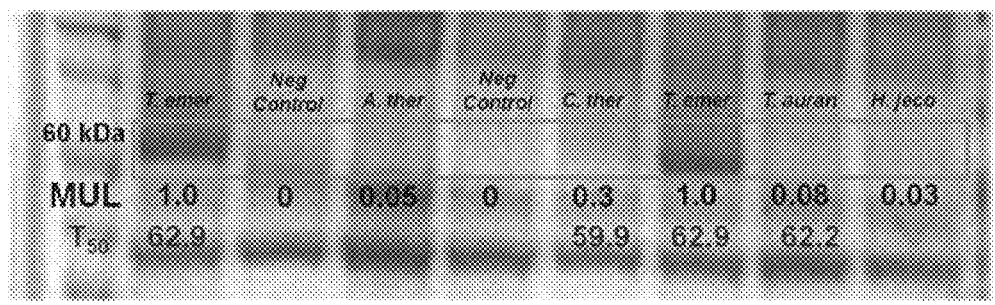
FIG. 8 shows SDS-PAGE analysis of CBH I parent YPD yeast culture secretion supernatants. Primary $T.$ $emersonii$ CBH I band appears at ~62 kDa and is encompassed by green rectangle. Increase in molecular mass relative to the amino acid molecular mass of ~53 kDa can be accounted for by an expected additional 8-10 kDa from N-linked and O-linked glycosylation. Smearing at molecular masses above ~62 kDa may be due to glycosylation heterogeneity. Blue numbers denote CBH I supernatant activity, relative to $T.$ $emersonii$ CBH I, toward MUL. Red numbers denote $T_{50}$ values for the 3 CBH I parents whose secretion is sufficient for thermostability measurement.

As shown in FIG. 8, the *T. emersonii* CBH I showed much higher expression than the other 4 parents in an SDS-PAGE gel. *T. emersonii* yeast secretion culture supernatant also contained more than three times the activity [(2.3+/−0.3)× $10^{-4}$ mol/L/s] toward the fluorescent, soluble CBH I substrate 4-methylumbelliferyl lactopyranoside (MUL) than supernatant for the second most highly expressed parent, from *C. thermophilum*. Accurate CBH I thermostability measurements, in the form of ten-minute T$_{50}$ values, required a total MUL hydrolysis rate of 1.6*$10^{-5}$ mol/L/s. Neither the *H. jecorina* (P3) nor the *A. thermophilum* (P4) parents reached this threshold. CBH Is with supernatant activity values below this level were categorized as 'not secreted'. The *T. emersonii* parent had a T$_{50}$ (62.9+/−0.3° C.)

greater than those of the *C. thermophilum* (59.9+/−0.3° C.) and *T. aurantiacus* (62.2+/−0.4° C.) parents. The relatively high stability and secretion of *T. emersonii* CBH I motivated choosing it as the background for screening sequence blocks from other enzymes.

SCHEMA Chimera Family Design.

The *T. emersonii* CBH I crystal structure (pdb 1Q9H) was used to prepare the contact map used by SCHEMA to evaluate disruption upon recombination, which is needed by RASPP for choosing the block boundaries that minimize library average disruption <E>. As crystal structures for neither a CBH I linker nor CBM are available, SCHEMA recombination was applied only to the CBH I catalytic domain. CBH I chimeras therefore contain the linker and CBM corresponding to the parent represented at block 8. An analysis of the 5-parent, 8-block family designs returned by the RASPP algorithm led us to choose the block boundaries depicted in FIG. 1. The $5^8$=390,625 chimeras in this family have <E>=20.3 and <m>=66.0, providing a desirable balance between a high number of mutations and a low number of broken contacts.

Sample Chimeras for Stability Analysis.

Fungal CBH Is are poorly secreted from the *S. cerevisiae* host. To maximize the fraction of sample set chimeras that provide useful data, a block screening strategy was implemented in which 32 blocks from 4 parents are substituted, one at a time, into the background of a CBH I that is secreted at relatively high levels (parent 5). The 32-member CBH I "monomera" sample set has <E>=5.9 and <m>=15.6. These are considerably lower than the average values of the 390,625 sequences in the family and are therefore expected to have a high likelihood of retaining fold and cellulase function.

Figure 9:
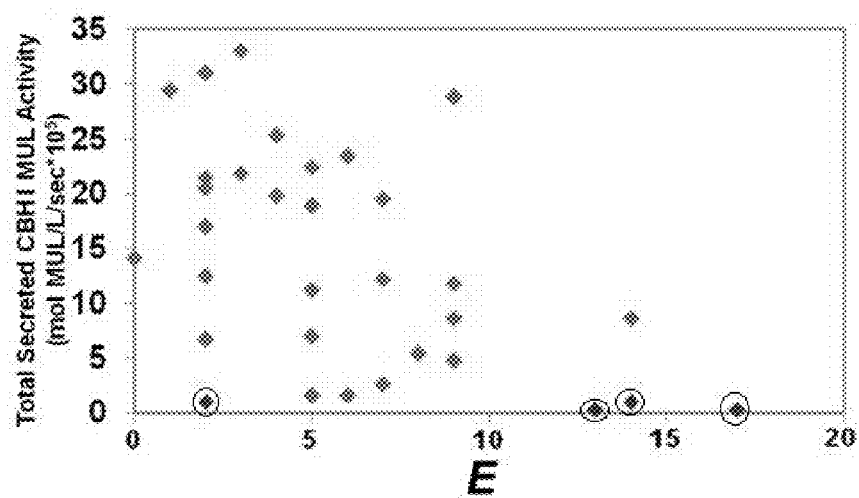
FIG. 9 shows total secreted CBH I MUL activity versus number of broken contacts (E) for CBH I monomeras. Block 7 monomera data points are circled.
Figure 10:
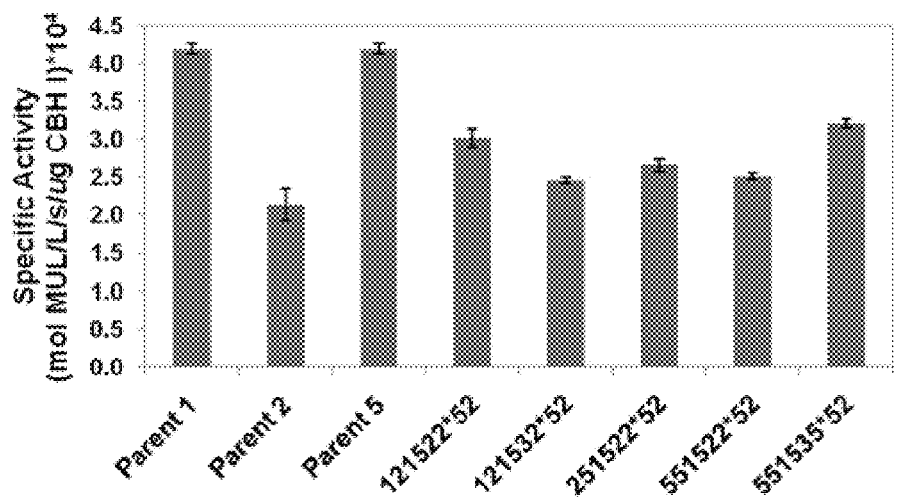
FIG. 10 shows specific activity toward MUL [(mol MUL/ (L·µg CBHI·s)×10$^4$] for Ni$^{2+}$ affinity-isolated CBH I parents and chimeras. Reaction carried out for 30 minutes in 50 mM sodium acetate with 300 µM MUL and 29.2 µg/mL affinity-isolated CBH I. *5 denotes block 7 from parent 5 with stabilizing subblock C insertion.

The 32 monomeras were prepared by total gene synthesis. As shown in FIG. 2, 28 monomeras (88%) were secreted in functional form from *S. cerevisiae*. However, none of the monomeras containing substitutions at block 7, the largest block, were secreted. Substitutions at block 4 were also highly detrimental to monomera secretion. On the other hand, several of the monomeras with substitutions at blocks 2 and 5 were more highly secreted than the *T. emersonii* background parent. Although an inverse relationship between E and secretion for CBH II chimeras was previously observed, E is not predictive of CBH I monomera secretion (FIG. 9). The CBH I supernatant activity toward MUL as a proxy for CBH I secretion is based on the observation that Ni-NTA affinity-isolated, C-terminally His$_6$-tagged CBH I parents and chimeras have similar specific activities toward MUL (FIG. 10).

FIG. 3 summarizes the block stability contributions and shows that 4 block substitutions resulted in CBH I chimeras with increased T$_{50}$ values; the stabilizing blocks B1P1, B3P1, B5P2 and B8P2 increase the T$_{50}$ by between ~0.7° C. and ~1.6° C. Although no stabilizing blocks were obtained from the two parents that were not secreted (P3, P4), these parents did provide five neutral blocks, B1P3, B2P3, B5P3, B1P4 and B2P4. Assuming that block neutrality is independent of chimera background, these blocks can be used to increase chimera sequence diversity without reducing thermostability.

Of the 10 disulfide bonds in CBH I, 5 involve Cys residues originating from different blocks. For example, Cys135 (parent 5 numbering; see SEQ ID NO:15) of block 4 forms a disulfide bond with Cys401 of block 8, and Cys253 of block 7 is paired with Cys227 of block 6 (FIG. 1). An analysis of whether the recombination of disulfide-bonded Cys pairs was responsible for the detrimental effect on secretion and/or stability that results from the block 4 and 7 substitutions was examined. This was tested by substituting the 4-8 and 6-7 block pairs from parents 1 and 2 into parent 5. Conserving the disulfides in this way, however, this resulted in expression levels that fall between those of the monomeras containing the respective single block substitutions or are not secreted at all (Table 1). T$_{50}$ values for the chimeras with substitutions at blocks 4 and 8 fall between those for the respective block 4 and block 8 monomeras. These results show that C135-C401 and C227-C253 disulfide bonds containing Cys residues in blocks taken from different parents do not reduce secretion or stability relative to these blocks coming from the same parent.

The lack of secretion for block 7-substituted monomeras prevented the assignment of stability contributions to blocks at this position. Only one monomera in which B7P5 was substituted into the other four parents was secreted, where moving block 7 into parent 2, which has the highest identity (81%) to parent 5, increased expression more than fivefold and increased the T$_{50}$ of parent 2 by 1.5° C.

Thermostable CBH I Chimera Design and Characterization.

A set of diverse, thermostable chimeras was then designed that would also be secreted at relatively high levels. To achieve high stability, all 16 members of this set include the two most stabilizing blocks, B3P1 and B8P5. Similarly, as both B5P3 and B5P5 were observed to have significant and similar stabilizing effects, all of the designed chimeras contain one of these two blocks. As blocks 4 and 7 from parents other than *T. emersonii* parent 5 were found to either eliminate or markedly reduce secretion, all 16 designed chimeras feature both B4P5 and B7P5. Finally, to obtain high sequence diversity without sacrificing thermostability and/or secretion level, we incorporated a collection of 11 blocks, B1P1, B1P2, B1P3, B1P4, B1P5, B2P2, B2P3, B2P4, B2P5, B6P2 and B6P5, that were expected to be either beneficial or neutral with respect to chimera stability and secretion level.

The chimeras are thus comprised of 17 of the 40 available CBH I blocks and contain an average of 37 mutations relative to the closest parent (of 441 total residues). They differ from each other by 21 mutations on average and give representation to all five parent CBH Is. As shown in FIG. 4, all 16 of these predicted-stable CBH I chimeras in fact have T$_{50}$ values that are significantly greater than that of the most stable CBH I parent (from *T. emersonii*). Eight of the 16 thermostable chimeras have T$_{50}$ values that are 2 or more degrees above *T. emersonii*, with the most thermostable chimera, 55152552, having a T$_{50}$ that is higher by 3.4° C. As shown in FIG. 4, all but one of the 16 stable chimeras are secreted at levels equal to or greater than that for the second most highly secreted parent, from *C. thermophilum*, and 8 chimeras were secreted at levels equal to or greater than that for the most highly secreted parent, from *T. emersonii*.

As the attempts to substitute B7P5 into the backgrounds of the 4 other parents were successful for parent 2, the parent most identical to parent 5, B7P2 was substituted for B7P5 in the background of five thermostable chimeras. As shown in Table 4, this substitution either markedly reduced or abrogated secretion in all five cases and decreased secreted chimera T$_{50}$ values by an average of 2.3+/−0.8° C.

TABLE 4

Comparison of $T_{50}$ values and total yeast secreted activity [(mol MUL/(L · s)) × $10^5$] for B7P5 and B72 CBH I chimeras.

| Chimera | 12152252 | 25152252 | 55153252 | 55552252 | 55152252 |
|---|---|---|---|---|---|
| $T_{50}$(° C.) | 65.3 +/− 0.1 | 65.0 +/− 0.1 | 64.4 +/− 0.2 | 65.6 +/− 0.7 | 66.3 +/− 1.0 |
| Secreted Activity | 10.2 | 22.2 | 20.0 | 18.5 | 19.6 |
| Chimera | 12152222 | 25152222 | 55153222 | 555522252 | 55152222 |
| $T_{50}$(° C.) | NS | 63.6 +/− 0.0 | 62.5 +/− 0.1 | 62.5 +/− 0.1 | 63.4 +/− 0.1 |
| Secreted Activity | 0.3 | 1.6 | 1.9 | 1.9 | 1.9 |

Error bars on $T_{50}$ values denote extremes of two duplicates. Total yeast secreted activity are single measurements for single cultures. NS denotes total secreted activity too low to permit $T_{50}$ measurement.

Figure 11:
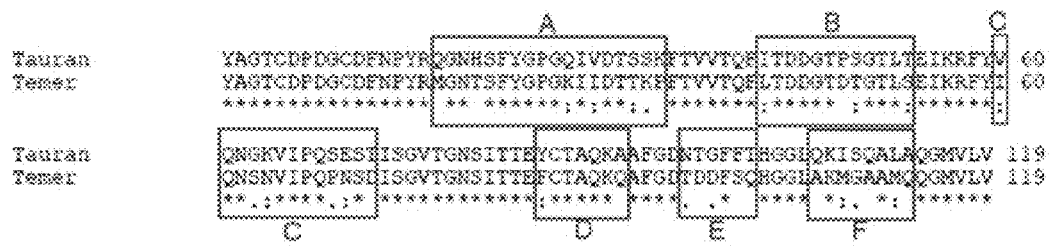
FIG. 11 shows an alignment of SEQ ID NO:4 (B7P2: $T.$ $auran$) with SEQ ID NO:10 (B7P5: $T.$ $emer$). Subblocks enclosed in boxes. Subblock C begins at position 60 and continues into second line of alignment.

Experiments were performed to determine whether smaller stretches of amino acids, or subblocks, lying within block 7 could be swapped in chimeric CBH Is and whether these blocks could make positive thermostability contributions. This mode of interchanging sequence between the two most identical sequences, parents 2 and 5, was continued. Six subblocks within B7P2 were selected and chosen on the basis of cloning convenience and a relatively equal distribution of the 32 mutations separating B7P2 and B7P5. As shown in FIG. 11, the six subblocks feature between 2 and 7 mutations. Table 5 shows that three of the six subblocks (C, D and E) either increase or do not reduce secretion when substituted into parent 5. Subblock C, which contains 6 mutations, was found to increase the $T_{50}$ of *T. emersonii* CBH I by approximately 1.0° C.

TABLE 5

$T_{50}$ values and total secreted yeast activity for subblock-substituted *T. emersonii* CBH I variants.

| Subblock Substituted | $T_{50}$ (° C.) | Secreted Activity |
|---|---|---|
| Parent 5 (*T. emersonii*) | 62.9 +/− 0.3 | 23.0 +/− 3.0 |
| A | 59.9 +/− 0.5 | 0.7 |
| B | 62.6 +/− 0.2 | 8.3 |
| C | 63.9 +/− 0.0 | 46.0 |
| D | 62.7 +/− 0.4 | 33.6 |
| E | 61.9 +/− 0.1 | 20.4 |
| F | 62.1 +/− 0.1 | 7.5 |

Error bars on $T_{50}$ values denote extremes of two duplicate measurements. Subblock total yeast secreted activity [(mol MUL/(L · s)) × $10^5$] are single measurements for single cultures. $T_{50}$ and total secreted values for *T. emersonii* and means and standard deviations for 8 and 3 respective replicates. NS denotes insufficient total activity for $T_{50}$ measurement.

As shown in Table 2, where B7P5 containing subblock C from parent 2 is denoted by "5" at the 7 position, this subblock improved the thermostability of all five chimeras into which it was substituted, with an average $T_{50}$ increase of 1.5+/−0.4° C. Furthermore, the B7P*5 chimeras are all secreted at higher levels than the corresponding B7P5 chimeras.

Cellulose Hydrolysis Using Thermostable CBH I Chimeras.

Figure 12:
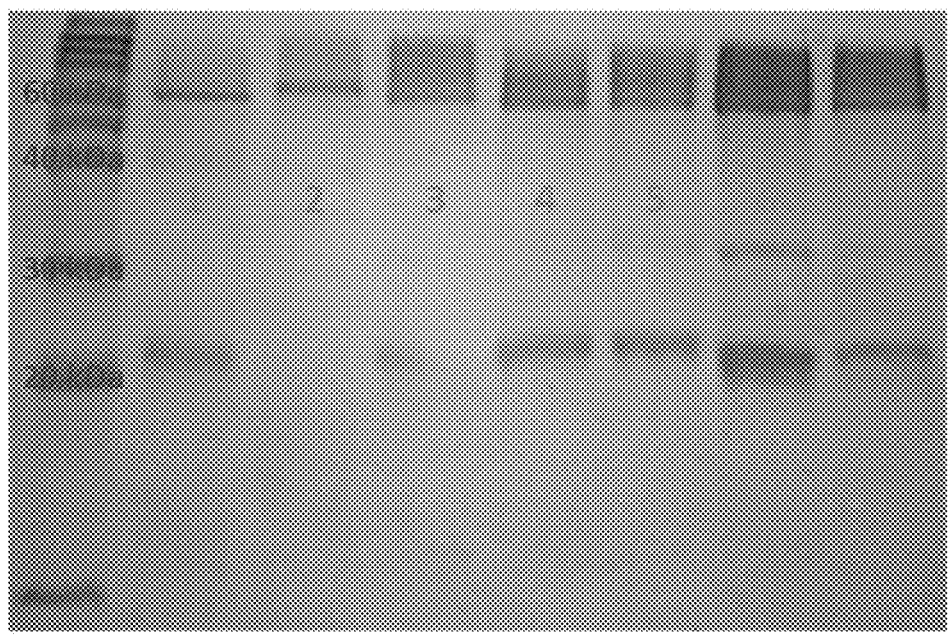
FIG. 12 shows SDS PAGE analyses of Ni$^{2+}$ affinity-isolated CBH I parent and chimera samples. All samples loaded at 1.5 µg protein per lane. Sample lanes: 1-Parent 5, 2-Parent 1, 5-121522*52 4-551535*52, 5-551522*52, 6-251522*52, 7-121522*52. Parent 2 affinity isolated sample (not included in gel) protein concentration is too low for Coomassie blue visualization. Parent 1 expected molecular weight is greater than parent 5 and chimeras due to presence of $C.$ $thermophilum$ linker and CBM rather than $T.$ $emersonii$ linker and CBM. *5 denotes block 7 from parent 5 with stabilizing subblock C insertion.
Figure 13:
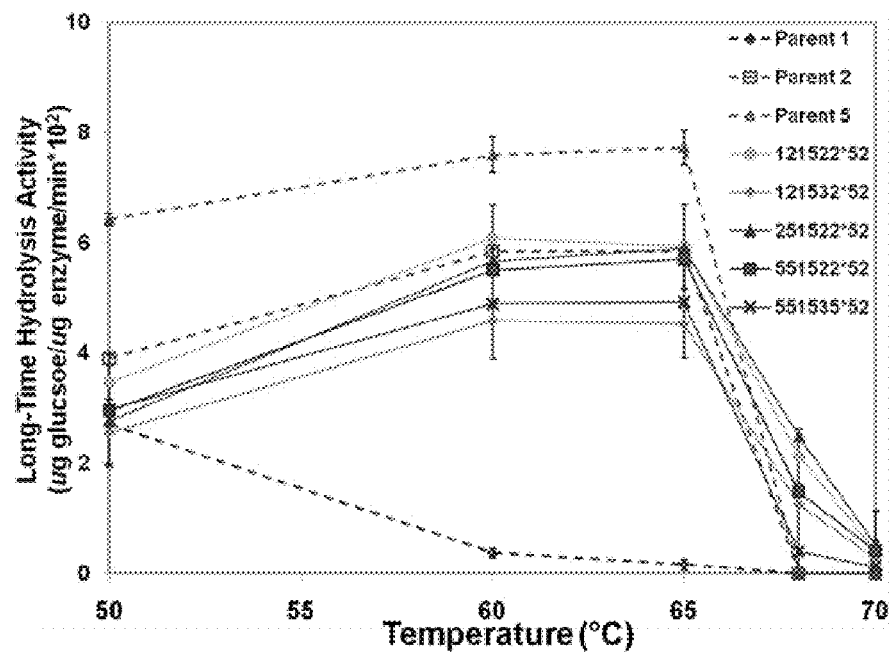
FIG. 13 shows specific activity versus temperature for affinity-isolated CBH I parents and chimeras. Reaction carried out for 16 hours in 50 mM sodium acetate with 60 mg/mL solid cellulose and 14.6 µg/mL affinity-isolated CBH I. Error bars denote standard deviations for three replicates. *5 denotes block 7 from parent 5 with stabilizing subblock C insertion.

Experiments there also performed to determine whether an increase in $T_{50}$, which is measured after thermal denaturation in the absence of substrate, corresponds to an increase in the maximum CBH I solid cellulose hydrolysis temperature. To this end yeast secretion constructs were built for the 3 secreted CBH I parents and 5 thermostable B7P*5 chimeras in which the CBH I N-terminus was appended with a $His_6$ tag to allow purification by Ni-NTA affinity chromatography from the components in the yeast culture medium. As shown in FIG. 12, although CBH I bands appear at the anticipated molecular weight of ~60 kDa in the SDS-PAGE, there are also unexpected bands at ~20 kDa. Although these samples are not sufficiently homogeneous to permit CBH I specific activity measurements, the removal of background protein and carbohydrates from the medium allows valid comparison of maximum solid cellulose hydrolysis temperatures.

Figure 5:
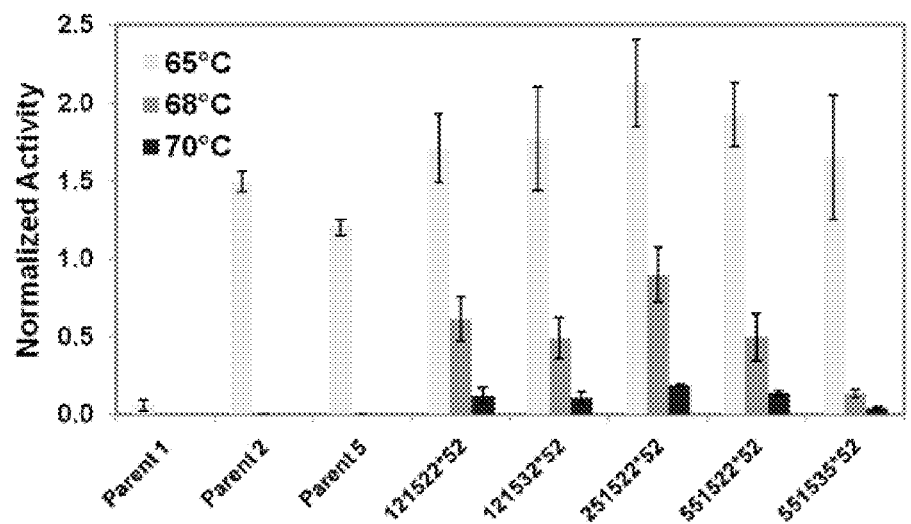
FIG. 5 shows normalized high temperature solid cellulose hydrolysis activity for affinity-isolated CBH I parents and chimeras. Values presented are activity at given temperature relative to activity at 50° C. Reactions were carried out for 16 hours in 50 mM sodium acetate, pH 4.8, with 60 mg/mL solid cellulose and 14.6 μg/mL affinity-isolated CBH I. Error bars denote standard deviations for three replicates. *5 denotes block 7 from parent 5 with stabilizing subblock C insertion.

As shown in FIG. 5, higher $T_{50}$ values are indicative of a greater ability to hydrolyze solid cellulose at elevated temperatures over a 16-hour interval. Whereas none of the parent enzymes were active at temperatures above 65° C., all five of the tested thermostable chimeras, which contain an average of 42 mutations and differ from each other by an average of 16 mutations, retained some hydrolytic activity at 70° C. The five tested thermostable chimeras all have between thirty and fifty percent lower specific activity, however, than the *T. emersonii* parent at 50° C. (assuming that all of the protein loaded into each reaction is active CBH I).

The Ni-NTA affinity-isolated CBH I samples are also useful for evaluating whether CBH I specific activities toward the soluble MUL substrate, measured at 45° C., are retained upon recombination. As shown in FIG. 10, the estimated specific activities of the five thermostable $His_6$-tagged chimeras, based on the assumption that the affinity-isolated CBH I samples are 100% pure, lie within $4 \times 10^{-5}$ mol MUL/(L s µg CBH I) of the mean value of $2.8 \times 10^{-4}$ mol MUL/(L s µg CBH I). These specific activities fall between the respective values of $(4.3+/-0.1) \times 10^{-4}$, $(2.3+/-0.2) \times 10^{-4}$, and $(4.3+/-0.1) \times 10^{-4}$ mol MUL/(L s µg CBH I) measured for parents 1, 2 and 5. Thus the thermostable chimeras have not increased in stability at the cost of their specific activities toward the soluble MUL substrate.

Figure 6:
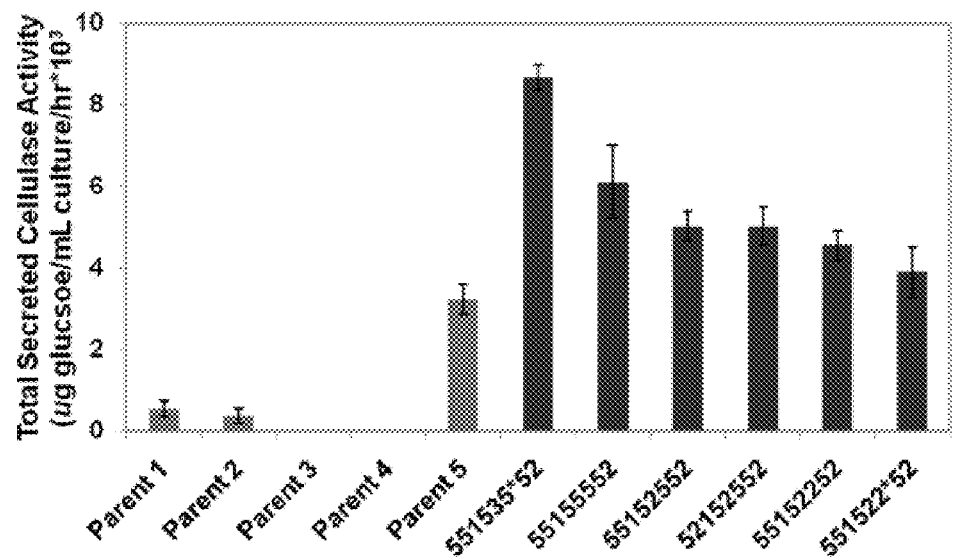
FIG. 6 shows total yeast secreted activity toward solid cellulose for CBH I parents and chimeras. Yeast culture supernatant was incubated with microcrystalline cellulose in 50 mM sodium acetate, pH 4.8, for 1 hour at 4° C. to bind CBH I. Cellulose was subsequently washed and hydrolysis allowed to proceed for 90 minutes at 37° C. Error bars represent standard deviations for three replicates. *5 denotes block 7 from parent 5 with stabilizing subblock C insertion.

The total cellulase activity secreted from yeast is relevant in consolidated bioprocess (CBP) applications, where recombinant strains of *S. cerevisiae* convert cellulosic biomass to fermentable simple sugars and ferment the simple sugars to biofuel in a single process step. The total solid cellulose hydrolysis activities were measured for the 5 CBH I parents and a set of 6 stable chimeras with total secreted activities toward the soluble MUL substrate that are equal to or greater than that of *T. emersonii* CBH I. As shown in FIG. 6, all 6 of the CBH I chimeras also exhibit more total solid cellulose hydrolysis activity than any of the parents.

While various specific embodiments have been illustrated and described, it will be appreciated that various changes can be made without departing from the spirit and scope of the invention(s).

What is claimed is:

1. An enzymatic preparation comprising at least two recombinant enzymes comprising at least 98% amino acid sequence identity to a polypeptide having the sequences selected from the group consisting of SEQ ID NO: 19, 20, 21, 22, 23, 24, 25, 26, 27, 28, 29, 30, 31, 32, 33, and 34, wherein each of the enzymes has cellobiohydrolase activity.

2. The enzymatic preparation of claim 1, wherein the enzymatic preparation comprises a polypeptide having at least 98% sequence identity to the polypeptide of SEQ ID NO: 20 and having cellobiohydrolase activity.

3. The enzymatic preparation of claim 1, wherein the enzymatic preparation comprises a polypeptide having at least 98% sequence identity to the polypeptide of SEQ ID NO: 34 and having cellobiohydrolase activity.

4. The enzymatic preparation of claim 1, wherein the enzymatic preparation comprises a polypeptide having at least 98% sequence identity to the polypeptide of SEQ ID NO: 20 and having cellobiohydrolase activity and a polypeptide having at least 98% sequence identity to the polypeptide of SEQ ID NO: 34 and having cellobiohydrolase activity.

5. The enzymatic preparation of claim 1, wherein the preparation comprises a disrupted cell or microbial preparation.

6. The enzymatic preparation of claim 1, further comprising one or more enzymes selected from the group consisting of a cellobiohydrolase II, an endoglucanase and a β-glucosidase.

7. A method of treating a biomass comprising cellulose, the method comprising contacting the biomass with the enzymatic preparation of claim 1.

8. The method of claim 7, wherein the method is carried out at about 65° C.

* * * * *

SEQUENCE LISTING

<160> NUMBER OF SEQ ID NOS: 34

<210> SEQ ID NO 1

<211> LENGTH: 1599
<212> TYPE: DNA
<213> ORGANISM: Chaetomium thermophilum
<220> FEATURE:
<221> NAME/KEY: CDS
<222> LOCATION: (1)..(1599)

<400> SEQUENCE: 1

| | | | | | | | | | | | | | | | | |
|---|---|---|---|---|---|---|---|---|---|---|---|---|---|---|---|---|
| atg | atg | tat | aag | aag | ttc | gcc | gct | ctc | gcc | gcc | ctc | gtg | gct | ggc | gcc | 48 |
| Met | Met | Tyr | Lys | Lys | Phe | Ala | Ala | Leu | Ala | Ala | Leu | Val | Ala | Gly | Ala | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| tcc | gcc | cag | cag | gct | tgc | tcc | ctc | acc | gct | gag | aac | cac | cct | agc | ctc | 96 |
| Ser | Ala | Gln | Gln | Ala | Cys | Ser | Leu | Thr | Ala | Glu | Asn | His | Pro | Ser | Leu | |
| | | | 20 | | | | | 25 | | | | | 30 | | | |

| | | | | | | | | | | | | | | | | |
|---|---|---|---|---|---|---|---|---|---|---|---|---|---|---|---|---|
| acc | tgg | aag | cgc | tgc | acc | tct | ggc | ggc | agc | tgc | tcg | acc | gtg | aac | ggc | 144 |
| Thr | Trp | Lys | Arg | Cys | Thr | Ser | Gly | Gly | Ser | Cys | Ser | Thr | Val | Asn | Gly | |
| | | 35 | | | | | 40 | | | | | 45 | | | | |

| | | | | | | | | | | | | | | | | |
|---|---|---|---|---|---|---|---|---|---|---|---|---|---|---|---|---|
| gcc | gtc | acc | atc | gat | gcc | aac | tgg | cgc | tgg | act | cac | acc | gtc | tcc | ggc | 192 |
| Ala | Val | Thr | Ile | Asp | Ala | Asn | Trp | Arg | Trp | Thr | His | Thr | Val | Ser | Gly | |
| | 50 | | | | | 55 | | | | | 60 | | | | | |

| | | | | | | | | | | | | | | | | |
|---|---|---|---|---|---|---|---|---|---|---|---|---|---|---|---|---|
| tcg | acc | aac | tgc | tac | acc | ggc | aac | cag | tgg | gat | acc | tcc | ctc | tgc | act | 240 |
| Ser | Thr | Asn | Cys | Tyr | Thr | Gly | Asn | Gln | Trp | Asp | Thr | Ser | Leu | Cys | Thr | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| gat | ggc | aag | agc | tgc | gcc | cag | acc | tgc | tgc | gtc | gat | ggc | gct | gac | tac | 288 |
| Asp | Gly | Lys | Ser | Cys | Ala | Gln | Thr | Cys | Cys | Val | Asp | Gly | Ala | Asp | Tyr | |
| | | | 85 | | | | | 90 | | | | | 95 | | | |

| | | | | | | | | | | | | | | | | |
|---|---|---|---|---|---|---|---|---|---|---|---|---|---|---|---|---|
| tct | tcg | acc | tat | ggt | atc | acc | acc | agc | ggt | gac | tcc | ctg | aac | ctc | aag | 336 |
| Ser | Ser | Thr | Tyr | Gly | Ile | Thr | Thr | Ser | Gly | Asp | Ser | Leu | Asn | Leu | Lys | |
| | | | 100 | | | | | 105 | | | | | 110 | | | |

| | | | | | | | | | | | | | | | | |
|---|---|---|---|---|---|---|---|---|---|---|---|---|---|---|---|---|
| ttc | gtc | acc | aag | cac | cag | tac | ggc | acc | aac | gtc | ggc | tcc | cgt | gtc | tat | 384 |
| Phe | Val | Thr | Lys | His | Gln | Tyr | Gly | Thr | Asn | Val | Gly | Ser | Arg | Val | Tyr | |
| | | 115 | | | | | 120 | | | | | 125 | | | | |

| | | | | | | | | | | | | | | | | |
|---|---|---|---|---|---|---|---|---|---|---|---|---|---|---|---|---|
| ctg | atg | gag | aac | gac | acc | aag | tac | cag | atg | ttc | gag | ctc | ctc | ggc | aac | 432 |
| Leu | Met | Glu | Asn | Asp | Thr | Lys | Tyr | Gln | Met | Phe | Glu | Leu | Leu | Gly | Asn | |
| | 130 | | | | | 135 | | | | | 140 | | | | | |

| | | | | | | | | | | | | | | | | |
|---|---|---|---|---|---|---|---|---|---|---|---|---|---|---|---|---|
| gag | ttc | acc | ttc | gat | gtc | gat | gtc | tcc | aac | ctg | ggc | tgc | ggt | ctc | aac | 480 |
| Glu | Phe | Thr | Phe | Asp | Val | Asp | Val | Ser | Asn | Leu | Gly | Cys | Gly | Leu | Asn | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| ggc | gcc | ctc | tac | ttc | gtt | tcc | atg | gat | gct | gat | ggt | ggc | atg | agc | aaa | 528 |
| Gly | Ala | Leu | Tyr | Phe | Val | Ser | Met | Asp | Ala | Asp | Gly | Gly | Met | Ser | Lys | |
| | | | 165 | | | | | 170 | | | | | 175 | | | |

| | | | | | | | | | | | | | | | | |
|---|---|---|---|---|---|---|---|---|---|---|---|---|---|---|---|---|
| tac | tct | ggc | aac | aag | gct | ggc | gcc | aag | tac | ggt | acc | ggc | tac | tgc | gat | 576 |
| Tyr | Ser | Gly | Asn | Lys | Ala | Gly | Ala | Lys | Tyr | Gly | Thr | Gly | Tyr | Cys | Asp | |
| | | | 180 | | | | | 185 | | | | | 190 | | | |

| | | | | | | | | | | | | | | | | |
|---|---|---|---|---|---|---|---|---|---|---|---|---|---|---|---|---|
| gct | cag | tgc | ccg | cgc | gac | ctc | aag | ttc | atc | aac | ggc | gag | gcc | aac | gtt | 624 |
| Ala | Gln | Cys | Pro | Arg | Asp | Leu | Lys | Phe | Ile | Asn | Gly | Glu | Ala | Asn | Val | |
| | | 195 | | | | | 200 | | | | | 205 | | | | |

| | | | | | | | | | | | | | | | | |
|---|---|---|---|---|---|---|---|---|---|---|---|---|---|---|---|---|
| ggg | aac | tgg | acc | ccc | tcg | acc | aac | gat | gcc | aac | gcc | ggc | ttc | ggc | cgc | 672 |
| Gly | Asn | Trp | Thr | Pro | Ser | Thr | Asn | Asp | Ala | Asn | Ala | Gly | Phe | Gly | Arg | |
| | 210 | | | | | 215 | | | | | 220 | | | | | |

| | | | | | | | | | | | | | | | | |
|---|---|---|---|---|---|---|---|---|---|---|---|---|---|---|---|---|
| tat | ggc | agc | tgc | tgc | tct | gag | atg | gat | gtc | tgg | gag | gcc | aac | aac | atg | 720 |
| Tyr | Gly | Ser | Cys | Cys | Ser | Glu | Met | Asp | Val | Trp | Glu | Ala | Asn | Asn | Met | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| gct | act | gcc | ttc | act | cct | cac | cct | tgc | acc | acc | gtt | ggc | cag | agc | cgc | 768 |
| Ala | Thr | Ala | Phe | Thr | Pro | His | Pro | Cys | Thr | Thr | Val | Gly | Gln | Ser | Arg | |
| | | | 245 | | | | | 250 | | | | | 255 | | | |

| | | | | | | | | | | | | | | | | |
|---|---|---|---|---|---|---|---|---|---|---|---|---|---|---|---|---|
| tgc | gag | gcc | gac | acc | tgc | ggt | ggc | acc | tac | agc | tct | gac | cgc | tat | gct | 816 |
| Cys | Glu | Ala | Asp | Thr | Cys | Gly | Gly | Thr | Tyr | Ser | Ser | Asp | Arg | Tyr | Ala | |
| | | | 260 | | | | | 265 | | | | | 270 | | | |

| | | | | | | | | | | | | | | | | |
|---|---|---|---|---|---|---|---|---|---|---|---|---|---|---|---|---|
| ggt | gtt | tgc | gac | cct | gat | ggc | tgc | gac | ttc | aac | gcc | tac | cgc | caa | ggc | 864 |
| Gly | Val | Cys | Asp | Pro | Asp | Gly | Cys | Asp | Phe | Asn | Ala | Tyr | Arg | Gln | Gly | |

-continued

```
                 275                 280                 285
gac aag acc ttc tac ggc aag ggc atg act gtc gac acc aac aag aag    912
Asp Lys Thr Phe Tyr Gly Lys Gly Met Thr Val Asp Thr Asn Lys Lys
    290                 295                 300 atg acc gtc gtc acc cag ttc cac aag aac tcg gct ggc gtc ctc agc    960
Met Thr Val Val Thr Gln Phe His Lys Asn Ser Ala Gly Val Leu Ser
305                 310                 315                 320 gag atc aag cgc ttc tac gtc cag gac ggc aag atc att gcc aac gct   1008
Glu Ile Lys Arg Phe Tyr Val Gln Asp Gly Lys Ile Ile Ala Asn Ala
                325                 330                 335 gag tcc aag atc ccc ggc aac ccc gga aac tcc att acc cag gag tat   1056
Glu Ser Lys Ile Pro Gly Asn Pro Gly Asn Ser Ile Thr Gln Glu Tyr
            340                 345                 350 tgc gat gcc cag aag gtc gcc ttc agt aac acc gat gac ttc aac cgc   1104
Cys Asp Ala Gln Lys Val Ala Phe Ser Asn Thr Asp Asp Phe Asn Arg
        355                 360                 365 aag ggc ggt atg gct cag atg agc aag gcc ctc gca ggc ccc atg gtc   1152
Lys Gly Gly Met Ala Gln Met Ser Lys Ala Leu Ala Gly Pro Met Val
    370                 375                 380 ctg gtc atg tcc gtc tgg gat gac cac tac gcc aac atg ctc tgg ctc   1200
Leu Val Met Ser Val Trp Asp Asp His Tyr Ala Asn Met Leu Trp Leu
385                 390                 395                 400 gac tcg acc tac ccc atc gac cag gcc ggc gcc ccc ggc gcc gag cgc   1248
Asp Ser Thr Tyr Pro Ile Asp Gln Ala Gly Ala Pro Gly Ala Glu Arg
                405                 410                 415 ggt gct tgc ccg acc acc tcc ggt gtc cct gcc gag atc gag gcc cag   1296
Gly Ala Cys Pro Thr Thr Ser Gly Val Pro Ala Glu Ile Glu Ala Gln
            420                 425                 430 gtc ccc aac agc aac gtc atc ttc tcc aac atc cgt ttc ggc ccc atc   1344
Val Pro Asn Ser Asn Val Ile Phe Ser Asn Ile Arg Phe Gly Pro Ile
        435                 440                 445 ggc tcg acc gtc cct ggc ctt gac ggc agc aac ccc ggc aac ccg acc   1392
Gly Ser Thr Val Pro Gly Leu Asp Gly Ser Asn Pro Gly Asn Pro Thr
    450                 455                 460 acc acc gtc gtt cct ccc gct tct acc tcc acc tcc cgt ccg acc agc   1440
Thr Thr Val Val Pro Pro Ala Ser Thr Ser Thr Ser Arg Pro Thr Ser
465                 470                 475                 480 agc act agc tct ccc gtt tcg acc ccg act ggc cag ccc ggc ggc tgc   1488
Ser Thr Ser Ser Pro Val Ser Thr Pro Thr Gly Gln Pro Gly Gly Cys
                485                 490                 495 acc acc cag aag tgg ggc cag tgc ggc ggt atc ggc tac acc ggc tgc   1536
Thr Thr Gln Lys Trp Gly Gln Cys Gly Gly Ile Gly Tyr Thr Gly Cys
            500                 505                 510 act aac tgc gtt gct ggc acc acc tgc act cag ctc aac ccc tgg tac   1584
Thr Asn Cys Val Ala Gly Thr Thr Cys Thr Gln Leu Asn Pro Trp Tyr
        515                 520                 525 agc cag tgc ctg taa                                               1599
Ser Gln Cys Leu
    530

<210> SEQ ID NO 2
<211> LENGTH: 532
<212> TYPE: PRT
<213> ORGANISM: Chaetomium thermophilum

<400> SEQUENCE: 2

Met Met Tyr Lys Lys Phe Ala Ala Leu Ala Ala Leu Val Ala Gly Ala
1               5                   10                  15

Ser Ala Gln Gln Ala Cys Ser Leu Thr Ala Glu Asn His Pro Ser Leu
            20                  25                  30
```

```
Thr Trp Lys Arg Cys Thr Ser Gly Gly Ser Cys Ser Thr Val Asn Gly
        35                  40                  45

Ala Val Thr Ile Asp Ala Asn Trp Arg Trp Thr His Thr Val Ser Gly
50                  55                  60

Ser Thr Asn Cys Tyr Thr Gly Asn Gln Trp Asp Thr Ser Leu Cys Thr
65                  70                  75                  80

Asp Gly Lys Ser Cys Ala Gln Thr Cys Val Asp Gly Ala Asp Tyr
                85                  90                  95

Ser Ser Thr Tyr Gly Ile Thr Thr Ser Gly Asp Ser Leu Asn Leu Lys
                100                 105                 110

Phe Val Thr Lys His Gln Tyr Gly Thr Asn Val Gly Ser Arg Val Tyr
            115                 120                 125

Leu Met Glu Asn Asp Thr Lys Tyr Gln Met Phe Glu Leu Leu Gly Asn
        130                 135                 140

Glu Phe Thr Phe Asp Val Asp Val Ser Asn Leu Gly Cys Gly Leu Asn
145                 150                 155                 160

Gly Ala Leu Tyr Phe Val Ser Met Asp Ala Asp Gly Gly Met Ser Lys
                165                 170                 175

Tyr Ser Gly Asn Lys Ala Gly Ala Lys Tyr Gly Thr Gly Tyr Cys Asp
                180                 185                 190

Ala Gln Cys Pro Arg Asp Leu Lys Phe Ile Asn Gly Glu Ala Asn Val
        195                 200                 205

Gly Asn Trp Thr Pro Ser Thr Asn Asp Ala Asn Ala Gly Phe Gly Arg
210                 215                 220

Tyr Gly Ser Cys Cys Ser Glu Met Asp Val Trp Glu Ala Asn Asn Met
225                 230                 235                 240

Ala Thr Ala Phe Thr Pro His Pro Cys Thr Thr Val Gly Gln Ser Arg
                245                 250                 255

Cys Glu Ala Asp Thr Cys Gly Gly Thr Tyr Ser Ser Asp Arg Tyr Ala
                260                 265                 270

Gly Val Cys Asp Pro Asp Gly Cys Asp Phe Asn Ala Tyr Arg Gln Gly
            275                 280                 285

Asp Lys Thr Phe Tyr Gly Lys Gly Met Thr Val Asp Thr Asn Lys Lys
        290                 295                 300

Met Thr Val Val Thr Gln Phe His Lys Asn Ser Ala Gly Val Leu Ser
305                 310                 315                 320

Glu Ile Lys Arg Phe Tyr Val Gln Asp Gly Lys Ile Ile Ala Asn Ala
            325                 330                 335

Glu Ser Lys Ile Pro Gly Asn Pro Gly Asn Ser Ile Thr Gln Glu Tyr
            340                 345                 350

Cys Asp Ala Gln Lys Val Ala Phe Ser Asn Thr Asp Asp Phe Asn Arg
        355                 360                 365

Lys Gly Gly Met Ala Gln Met Ser Lys Ala Leu Ala Gly Pro Met Val
        370                 375                 380

Leu Val Met Ser Val Trp Asp Asp His Tyr Ala Asn Met Leu Trp Leu
385                 390                 395                 400

Asp Ser Thr Tyr Pro Ile Asp Gln Ala Gly Ala Pro Gly Ala Glu Arg
                405                 410                 415

Gly Ala Cys Pro Thr Thr Ser Gly Val Pro Ala Glu Ile Glu Ala Gln
            420                 425                 430

Val Pro Asn Ser Asn Val Ile Phe Ser Asn Ile Arg Phe Gly Pro Ile
        435                 440                 445
```

```
Gly Ser Thr Val Pro Gly Leu Asp Gly Ser Asn Pro Gly Asn Pro Thr
    450                 455                 460

Thr Thr Val Val Pro Pro Ala Ser Thr Ser Thr Ser Arg Pro Thr Ser
465                 470                 475                 480

Ser Thr Ser Ser Pro Val Ser Thr Pro Thr Gly Gln Pro Gly Gly Cys
                485                 490                 495

Thr Thr Gln Lys Trp Gly Gln Cys Gly Gly Ile Gly Tyr Thr Gly Cys
            500                 505                 510

Thr Asn Cys Val Ala Gly Thr Thr Cys Thr Gln Leu Asn Pro Trp Tyr
        515                 520                 525

Ser Gln Cys Leu
    530

<210> SEQ ID NO 3
<211> LENGTH: 1374
<212> TYPE: DNA
<213> ORGANISM: Thermoascus aurantiacus
<220> FEATURE:
<221> NAME/KEY: CDS
<222> LOCATION: (1)..(1374)

<400> SEQUENCE: 3 atg tat cag cgc gct ctt ctc ttc tct ttc ttc ctc gcc gcc gcc cgc      48
Met Tyr Gln Arg Ala Leu Leu Phe Ser Phe Phe Leu Ala Ala Ala Arg
1               5                   10                  15 gcg cag cag gcc tgt acc gta acc gca gag aat cac cct tcc ctg acc      96
Ala Gln Gln Ala Cys Thr Val Thr Ala Glu Asn His Pro Ser Leu Thr
            20                  25                  30 tgg cag caa tgc tcc agc ggc ggt agt tgt acc acg cag aat gga aaa     144
Trp Gln Gln Cys Ser Ser Gly Gly Ser Cys Thr Thr Gln Asn Gly Lys
        35                  40                  45 gtc gtt atc gat gcg aac tgg cgt tgg gtc cat acc acc tct gga tac     192
Val Val Ile Asp Ala Asn Trp Arg Trp Val His Thr Thr Ser Gly Tyr
    50                  55                  60 acc aac tgc tac acg ggc aat acg tgg gac acc agt atc tgt ccc gac     240
Thr Asn Cys Tyr Thr Gly Asn Thr Trp Asp Thr Ser Ile Cys Pro Asp
65                  70                  75                  80 gac gtg acc tgc gct cag aat tgt tgc ttg gat gga gcg gat tac agt     288
Asp Val Thr Cys Ala Gln Asn Cys Cys Leu Asp Gly Ala Asp Tyr Ser
                85                  90                  95 ggc acc tat ggt gtt acg acc agt ggc aac gcc ctg aga ctg aac ttt     336
Gly Thr Tyr Gly Val Thr Thr Ser Gly Asn Ala Leu Arg Leu Asn Phe
            100                 105                 110 gtc acc caa agc tca ggg aag aac att ggc tcg cgc ctg tac ctg ctg     384
Val Thr Gln Ser Ser Gly Lys Asn Ile Gly Ser Arg Leu Tyr Leu Leu
        115                 120                 125 cag gac gac acc act tat cag atc ttc aag ctg ctg ggt cag gag ttt     432
Gln Asp Asp Thr Thr Tyr Gln Ile Phe Lys Leu Leu Gly Gln Glu Phe
    130                 135                 140 acc ttc gat gtc gac gtc tcc aat ctc cct tgc ggg ctg aac ggc gcc     480
Thr Phe Asp Val Asp Val Ser Asn Leu Pro Cys Gly Leu Asn Gly Ala
145                 150                 155                 160 ctc tac ttt gtg gcc atg gac gcc gac ggc gga ttg tcc aaa tac cct     528
Leu Tyr Phe Val Ala Met Asp Ala Asp Gly Gly Leu Ser Lys Tyr Pro
                165                 170                 175 ggc aac aag gca ggc gct aag tat ggc act ggt tac tgc gac tct cag     576
Gly Asn Lys Ala Gly Ala Lys Tyr Gly Thr Gly Tyr Cys Asp Ser Gln
            180                 185                 190 tgc cct cgg gat ctc aag ttc atc aac ggt cag gcc aat gtt gaa ggc     624
Cys Pro Arg Asp Leu Lys Phe Ile Asn Gly Gln Ala Asn Val Glu Gly
```

|  |  |  |  |  |  |  |  |  |  |  |  |  |  |  |  |
|---|---|---|---|---|---|---|---|---|---|---|---|---|---|---|---|
|  |  |  | 195 |  |  |  | 200 |  |  |  | 205 |  |  |  |  |
| tgg | cag | ccg | tct | gcc | aac | gac | cca | aat | gcc | ggc | gtt | ggt | aac | cac | ggt | 672 |
| Trp | Gln | Pro | Ser | Ala | Asn | Asp | Pro | Asn | Ala | Gly | Val | Gly | Asn | His | Gly |  |
|  | 210 |  |  |  |  | 215 |  |  |  |  | 220 |  |  |  |  |  |
| tcc | tgc | tgc | gct | gag | atg | gat | gtc | tgg | gaa | gcc | aac | agc | atc | tct | act | 720 |
| Ser | Cys | Cys | Ala | Glu | Met | Asp | Val | Trp | Glu | Ala | Asn | Ser | Ile | Ser | Thr |  |
| 225 |  |  |  |  | 230 |  |  |  |  | 235 |  |  |  |  | 240 |  |
| gcg | gtg | acg | cct | cac | cca | tgc | gac | acc | ccc | ggc | cag | acc | atg | tgc | cag | 768 |
| Ala | Val | Thr | Pro | His | Pro | Cys | Asp | Thr | Pro | Gly | Gln | Thr | Met | Cys | Gln |  |
|  |  |  |  | 245 |  |  |  |  | 250 |  |  |  |  | 255 |  |  |
| gga | gac | gac | tgt | ggt | gga | acc | tac | tcc | tcc | act | cga | tat | gct | ggt | acc | 816 |
| Gly | Asp | Asp | Cys | Gly | Gly | Thr | Tyr | Ser | Ser | Thr | Arg | Tyr | Ala | Gly | Thr |  |
|  |  | 260 |  |  |  |  | 265 |  |  |  |  | 270 |  |  |  |  |
| tgc | gac | cct | gat | ggc | tgc | gac | ttc | aat | cct | tac | cgc | cag | ggc | aac | cac | 864 |
| Cys | Asp | Pro | Asp | Gly | Cys | Asp | Phe | Asn | Pro | Tyr | Arg | Gln | Gly | Asn | His |  |
| 275 |  |  |  |  | 280 |  |  |  |  | 285 |  |  |  |  |  |  |
| tcg | ttc | tac | ggc | ccc | ggg | cag | atc | gtc | gac | acc | agc | tcc | aaa | ttc | acc | 912 |
| Ser | Phe | Tyr | Gly | Pro | Gly | Gln | Ile | Val | Asp | Thr | Ser | Ser | Lys | Phe | Thr |  |
|  | 290 |  |  |  |  | 295 |  |  |  |  | 300 |  |  |  |  |  |
| gtc | gtc | acc | cag | ttc | atc | acc | gac | gac | ggg | acc | ccc | tcc | ggc | acc | ctg | 960 |
| Val | Val | Thr | Gln | Phe | Ile | Thr | Asp | Asp | Gly | Thr | Pro | Ser | Gly | Thr | Leu |  |
| 305 |  |  |  |  | 310 |  |  |  |  | 315 |  |  |  |  | 320 |  |
| acg | gag | atc | aaa | cgc | ttc | tac | gtc | cag | aac | ggc | aag | gta | atc | ccc | cag | 1008 |
| Thr | Glu | Ile | Lys | Arg | Phe | Tyr | Val | Gln | Asn | Gly | Lys | Val | Ile | Pro | Gln |  |
|  |  |  |  | 325 |  |  |  |  | 330 |  |  |  |  | 335 |  |  |
| tcg | gag | tcg | acg | atc | agc | ggc | gtc | acc | ggc | aac | tca | atc | acc | acc | gag | 1056 |
| Ser | Glu | Ser | Thr | Ile | Ser | Gly | Val | Thr | Gly | Asn | Ser | Ile | Thr | Thr | Glu |  |
|  |  |  | 340 |  |  |  |  | 345 |  |  |  |  | 350 |  |  |  |
| tat | tgc | acg | gcc | cag | aag | gcc | gcc | ttc | ggc | gac | aac | acc | ggc | ttc | ttc | 1104 |
| Tyr | Cys | Thr | Ala | Gln | Lys | Ala | Ala | Phe | Gly | Asp | Asn | Thr | Gly | Phe | Phe |  |
|  |  | 355 |  |  |  |  | 360 |  |  |  |  | 365 |  |  |  |  |
| acg | cac | ggc | ggg | ctt | cag | aag | atc | agt | cag | gct | ctg | gct | cag | ggc | atg | 1152 |
| Thr | His | Gly | Gly | Leu | Gln | Lys | Ile | Ser | Gln | Ala | Leu | Ala | Gln | Gly | Met |  |
| 370 |  |  |  |  | 375 |  |  |  |  | 380 |  |  |  |  |  |  |
| gtc | ctc | gtc | atg | agc | ctg | tgg | gac | gat | cac | gcc | gcc | aac | atg | ctc | tgg | 1200 |
| Val | Leu | Val | Met | Ser | Leu | Trp | Asp | Asp | His | Ala | Ala | Asn | Met | Leu | Trp |  |
| 385 |  |  |  |  | 390 |  |  |  |  | 395 |  |  |  |  | 400 |  |
| ctg | gac | agc | acc | tac | ccg | act | gat | gcg | gac | ccg | gac | acc | cct | ggc | gtc | 1248 |
| Leu | Asp | Ser | Thr | Tyr | Pro | Thr | Asp | Ala | Asp | Pro | Asp | Thr | Pro | Gly | Val |  |
|  |  |  |  | 405 |  |  |  |  | 410 |  |  |  |  | 415 |  |  |
| gcg | cgc | ggt | acc | tgc | ccc | acg | acc | tcc | ggc | gtc | ccg | gcc | gac | gtt | gag | 1296 |
| Ala | Arg | Gly | Thr | Cys | Pro | Thr | Thr | Ser | Gly | Val | Pro | Ala | Asp | Val | Glu |  |
|  |  |  | 420 |  |  |  |  | 425 |  |  |  |  | 430 |  |  |  |
| tcg | cag | tac | ccc | aat | tca | tat | gtt | atc | tac | tcc | aac | atc | aag | gtc | gga | 1344 |
| Ser | Gln | Tyr | Pro | Asn | Ser | Tyr | Val | Ile | Tyr | Ser | Asn | Ile | Lys | Val | Gly |  |
|  |  | 435 |  |  |  |  | 440 |  |  |  |  | 445 |  |  |  |  |
| ccc | atc | aac | tcg | acc | ttc | acc | gcc | aac | taa |  |  |  |  |  |  | 1374 |
| Pro | Ile | Asn | Ser | Thr | Phe | Thr | Ala | Asn |  |  |  |  |  |  |  |  |
|  | 450 |  |  |  |  | 455 |  |  |  |  |  |  |  |  |  |  |

<210> SEQ ID NO 4
<211> LENGTH: 457
<212> TYPE: PRT
<213> ORGANISM: Thermoascus aurantiacus

<400> SEQUENCE: 4

Met Tyr Gln Arg Ala Leu Leu Phe Ser Phe Phe Leu Ala Ala Ala Arg
1               5                   10                  15

Ala Gln Gln Ala Cys Thr Val Thr Ala Glu Asn His Pro Ser Leu Thr
            20                  25                  30

```
Trp Gln Gln Cys Ser Ser Gly Ser Cys Thr Thr Gln Asn Gly Lys
            35                  40                  45

Val Val Ile Asp Ala Asn Trp Arg Trp Val His Thr Thr Ser Gly Tyr
 50                  55                  60

Thr Asn Cys Tyr Thr Gly Asn Thr Trp Asp Thr Ser Ile Cys Pro Asp
 65                  70                  75                  80

Asp Val Thr Cys Ala Gln Asn Cys Cys Leu Asp Gly Ala Asp Tyr Ser
                 85                  90                  95

Gly Thr Tyr Gly Val Thr Thr Ser Gly Asn Ala Leu Arg Leu Asn Phe
                100                 105                 110

Val Thr Gln Ser Ser Gly Lys Asn Ile Gly Ser Arg Leu Tyr Leu Leu
            115                 120                 125

Gln Asp Asp Thr Thr Tyr Gln Ile Phe Lys Leu Leu Gly Gln Glu Phe
            130                 135                 140

Thr Phe Asp Val Asp Val Ser Asn Leu Pro Cys Gly Leu Asn Gly Ala
145                 150                 155                 160

Leu Tyr Phe Val Ala Met Asp Ala Asp Gly Gly Leu Ser Lys Tyr Pro
                165                 170                 175

Gly Asn Lys Ala Gly Ala Lys Tyr Gly Thr Gly Tyr Cys Asp Ser Gln
            180                 185                 190

Cys Pro Arg Asp Leu Lys Phe Ile Asn Gly Gln Ala Asn Val Glu Gly
            195                 200                 205

Trp Gln Pro Ser Ala Asn Asp Pro Asn Ala Gly Val Gly Asn His Gly
            210                 215                 220

Ser Cys Cys Ala Glu Met Asp Val Trp Glu Ala Asn Ser Ile Ser Thr
225                 230                 235                 240

Ala Val Thr Pro His Pro Cys Asp Thr Pro Gly Gln Thr Met Cys Gln
                245                 250                 255

Gly Asp Asp Cys Gly Gly Thr Tyr Ser Ser Thr Arg Tyr Ala Gly Thr
            260                 265                 270

Cys Asp Pro Asp Gly Cys Asp Phe Asn Pro Tyr Arg Gln Gly Asn His
            275                 280                 285

Ser Phe Tyr Gly Pro Gly Gln Ile Val Asp Thr Ser Ser Lys Phe Thr
            290                 295                 300

Val Val Thr Gln Phe Ile Thr Asp Asp Gly Thr Pro Ser Gly Thr Leu
305                 310                 315                 320

Thr Glu Ile Lys Arg Phe Tyr Val Gln Asn Gly Lys Val Ile Pro Gln
                325                 330                 335

Ser Glu Ser Thr Ile Ser Gly Val Thr Gly Asn Ser Ile Thr Thr Glu
            340                 345                 350

Tyr Cys Thr Ala Gln Lys Ala Ala Phe Gly Asp Asn Thr Gly Phe Phe
            355                 360                 365

Thr His Gly Gly Leu Gln Lys Ile Ser Gln Ala Leu Ala Gln Gly Met
            370                 375                 380

Val Leu Val Met Ser Leu Trp Asp Asp His Ala Ala Asn Met Leu Trp
385                 390                 395                 400

Leu Asp Ser Thr Tyr Pro Thr Asp Ala Asp Pro Asp Thr Pro Gly Val
                405                 410                 415

Ala Arg Gly Thr Cys Pro Thr Thr Ser Gly Val Pro Ala Asp Val Glu
            420                 425                 430

Ser Gln Tyr Pro Asn Ser Tyr Val Ile Tyr Ser Asn Ile Lys Val Gly
            435                 440                 445
```

```
Pro Ile Asn Ser Thr Phe Thr Ala Asn
    450                 455
```

<210> SEQ ID NO 5
<211> LENGTH: 1545
<212> TYPE: DNA
<213> ORGANISM: Hypocrea jecorina
<220> FEATURE:
<221> NAME/KEY: CDS
<222> LOCATION: (1)..(1545)

<400> SEQUENCE: 5

```
atg tat cgg aag ttg gcc gtc atc tcg gcc ttc ttg gcc aca gct cgt      48
Met Tyr Arg Lys Leu Ala Val Ile Ser Ala Phe Leu Ala Thr Ala Arg
1               5                   10                  15 gct cag tcg gcc tgc act ctc caa tcg gag act cac ccg cct ctg aca      96
Ala Gln Ser Ala Cys Thr Leu Gln Ser Glu Thr His Pro Pro Leu Thr
            20                  25                  30 tgg cag aaa tgc tcg tct ggt ggc acg tgc act caa cag aca ggc tcc     144
Trp Gln Lys Cys Ser Ser Gly Gly Thr Cys Thr Gln Gln Thr Gly Ser
        35                  40                  45 gtg gtc atc gac gcc aac tgg cgc tgg act cac gct acg aac agc agc     192
Val Val Ile Asp Ala Asn Trp Arg Trp Thr His Ala Thr Asn Ser Ser
    50                  55                  60 acg aac tgc tac gat ggc aac act tgg agc tcg acc cta tgt cct gac     240
Thr Asn Cys Tyr Asp Gly Asn Thr Trp Ser Ser Thr Leu Cys Pro Asp
65                  70                  75                  80 aac gag acc tgc gcg aag aac tgc tgt ctg gac ggt gcc gcc tac gcg     288
Asn Glu Thr Cys Ala Lys Asn Cys Cys Leu Asp Gly Ala Ala Tyr Ala
                85                  90                  95 tcc acg tac gga gtt acc acg agc ggt aac agc ctc tcc att ggc ttt     336
Ser Thr Tyr Gly Val Thr Thr Ser Gly Asn Ser Leu Ser Ile Gly Phe
            100                 105                 110 gtc acc cag tct gcg cag aag aac gtt ggc gct cgc ctt tac ctt atg     384
Val Thr Gln Ser Ala Gln Lys Asn Val Gly Ala Arg Leu Tyr Leu Met
        115                 120                 125 gcg agc gac acg acc tac cag gaa ttc acc ctg ctt ggc aac gag ttc     432
Ala Ser Asp Thr Thr Tyr Gln Glu Phe Thr Leu Leu Gly Asn Glu Phe
    130                 135                 140 tct ttc gat gtt gat gtt tcg cag ctg ccg tgc ggc ttg aac gga gct     480
Ser Phe Asp Val Asp Val Ser Gln Leu Pro Cys Gly Leu Asn Gly Ala
145                 150                 155                 160 ctc tac ttc gtg tcc atg gac gcg gat ggt ggc gtg agc aag tat ccc     528
Leu Tyr Phe Val Ser Met Asp Ala Asp Gly Gly Val Ser Lys Tyr Pro
                165                 170                 175 acc aac acc gct ggc gcc aag tac ggc acg ggg tac tgt gac agc cag     576
Thr Asn Thr Ala Gly Ala Lys Tyr Gly Thr Gly Tyr Cys Asp Ser Gln
            180                 185                 190 tgt ccc cgc gat ctg aag ttc atc aat ggc cag gcc aac gtt gag ggc     624
Cys Pro Arg Asp Leu Lys Phe Ile Asn Gly Gln Ala Asn Val Glu Gly
        195                 200                 205 tgg gag ccg tca tcc aac aac gcg aac acg ggc att gga gga cac gga     672
Trp Glu Pro Ser Ser Asn Asn Ala Asn Thr Gly Ile Gly Gly His Gly
    210                 215                 220 agc tgc tgc tct gag atg gat atc tgg gag gcc aac tcc atc tcc gag     720
Ser Cys Cys Ser Glu Met Asp Ile Trp Glu Ala Asn Ser Ile Ser Glu
225                 230                 235                 240 gct ctt acc ccc cac cct tgc acg act gtc ggc cag gag atc tgc gag     768
Ala Leu Thr Pro His Pro Cys Thr Thr Val Gly Gln Glu Ile Cys Glu
                245                 250                 255 ggt gat ggg tgc ggc gga act tac tcc gat aac aga tat ggc ggc act     816
Gly Asp Gly Cys Gly Gly Thr Tyr Ser Asp Asn Arg Tyr Gly Gly Thr
```

```
              Gly Asp Gly Cys Gly Gly Thr Tyr Ser Asp Asn Arg Tyr Gly Gly Thr
                              260                 265                 270 tgc gat ccc gat ggc tgc gac tgg gac cca tac cgc ctg ggc aac acc              864
Cys Asp Pro Asp Gly Cys Asp Trp Asp Pro Tyr Arg Leu Gly Asn Thr
            275                 280                 285 agc ttc tac ggc cct ggc tca agc ttt acc ctc gat acc acc aag aaa              912
Ser Phe Tyr Gly Pro Gly Ser Ser Phe Thr Leu Asp Thr Thr Lys Lys
        290                 295                 300 ttg acc gtt gtc acc cag ttc gag acg tcg ggt gcc atc aac cga tac              960
Leu Thr Val Val Thr Gln Phe Glu Thr Ser Gly Ala Ile Asn Arg Tyr
305                 310                 315                 320 tat gtc cag aat ggc gtc act ttc cag cag ccc aac gcc gag ctt ggt             1008
Tyr Val Gln Asn Gly Val Thr Phe Gln Gln Pro Asn Ala Glu Leu Gly
                325                 330                 335 agt tac tct ggc aac ggg ctc aac gat gat tac tgc aca gct gag gag             1056
Ser Tyr Ser Gly Asn Gly Leu Asn Asp Asp Tyr Cys Thr Ala Glu Glu
            340                 345                 350 gca gaa ttc ggc gga tcc tct ttc tca gac aag ggc ggc ctg act cag             1104
Ala Glu Phe Gly Gly Ser Ser Phe Ser Asp Lys Gly Gly Leu Thr Gln
        355                 360                 365 ttc aag aag gct acc tct ggc ggc atg gtt ctg gtc atg agt ctg tgg             1152
Phe Lys Lys Ala Thr Ser Gly Gly Met Val Leu Val Met Ser Leu Trp
370                 375                 380 gat gat tac tac gcc aac atg ctg tgg ctg gac tcc acc tac ccg aca             1200
Asp Asp Tyr Tyr Ala Asn Met Leu Trp Leu Asp Ser Thr Tyr Pro Thr
385                 390                 395                 400 aac gag acc tcc tcc aca ccc ggt gcc gtg cgc gga agc tgc tcc acc             1248
Asn Glu Thr Ser Ser Thr Pro Gly Ala Val Arg Gly Ser Cys Ser Thr
                405                 410                 415 agc tcc ggt gtc cct gct cag gtc gaa tct cag tct ccc aac gcc aag             1296
Ser Ser Gly Val Pro Ala Gln Val Glu Ser Gln Ser Pro Asn Ala Lys
            420                 425                 430 gtc acc ttc tcc aac atc aag ttc gga ccc att ggc agc acc ggc gac             1344
Val Thr Phe Ser Asn Ile Lys Phe Gly Pro Ile Gly Ser Thr Gly Asp
        435                 440                 445 cct agc ggc ggc aac cct ccc ggc gga aac ccg cct ggc acc acc acc             1392
Pro Ser Gly Gly Asn Pro Pro Gly Gly Asn Pro Pro Gly Thr Thr Thr
450                 455                 460 acc cgc cgc cca gcc act acc act gga agc tct ccc gga cct acc cag             1440
Thr Arg Arg Pro Ala Thr Thr Thr Gly Ser Ser Pro Gly Pro Thr Gln
465                 470                 475                 480 tct cac tac ggc cag tgc ggc ggt att ggc tac agc ggc ccc acg gtc             1488
Ser His Tyr Gly Gln Cys Gly Gly Ile Gly Tyr Ser Gly Pro Thr Val
                485                 490                 495 tgc gcc agc ggc aca act tgc cag gtc ctg aac cct tac tac tct cag             1536
Cys Ala Ser Gly Thr Thr Cys Gln Val Leu Asn Pro Tyr Tyr Ser Gln
            500                 505                 510 tgc ctg taa                                                                 1545
Cys Leu <210> SEQ ID NO 6
<211> LENGTH: 514
<212> TYPE: PRT
<213> ORGANISM: Hypocrea jecorina

<400> SEQUENCE: 6

Met Tyr Arg Lys Leu Ala Val Ile Ser Ala Phe Leu Ala Thr Ala Arg
1               5                   10                  15

Ala Gln Ser Ala Cys Thr Leu Gln Ser Glu Thr His Pro Pro Leu Thr
            20                  25                  30
```

```
Trp Gln Lys Cys Ser Ser Gly Gly Thr Cys Thr Gln Thr Gly Ser
         35                  40                  45

Val Val Ile Asp Ala Asn Trp Arg Trp Thr His Ala Thr Asn Ser Ser
    50                  55                  60

Thr Asn Cys Tyr Asp Gly Asn Thr Trp Ser Ser Thr Leu Cys Pro Asp
65                  70                  75                  80

Asn Glu Thr Cys Ala Lys Asn Cys Cys Leu Asp Gly Ala Ala Tyr Ala
                85                  90                  95

Ser Thr Tyr Gly Val Thr Thr Ser Gly Asn Ser Leu Ser Ile Gly Phe
                100                 105                 110

Val Thr Gln Ser Ala Gln Lys Asn Val Gly Ala Arg Leu Tyr Leu Met
            115                 120                 125

Ala Ser Asp Thr Thr Tyr Gln Glu Phe Thr Leu Leu Gly Asn Glu Phe
    130                 135                 140

Ser Phe Asp Val Asp Val Ser Gln Leu Pro Cys Gly Leu Asn Gly Ala
145                 150                 155                 160

Leu Tyr Phe Val Ser Met Asp Ala Asp Gly Gly Val Ser Lys Tyr Pro
                165                 170                 175

Thr Asn Thr Ala Gly Ala Lys Tyr Gly Thr Gly Tyr Cys Asp Ser Gln
                180                 185                 190

Cys Pro Arg Asp Leu Lys Phe Ile Asn Gly Gln Ala Asn Val Glu Gly
            195                 200                 205

Trp Glu Pro Ser Ser Asn Asn Ala Asn Thr Gly Ile Gly Gly His Gly
    210                 215                 220

Ser Cys Cys Ser Glu Met Asp Ile Trp Glu Ala Asn Ser Ile Ser Glu
225                 230                 235                 240

Ala Leu Thr Pro His Pro Cys Thr Thr Val Gly Gln Glu Ile Cys Glu
                245                 250                 255

Gly Asp Gly Cys Gly Gly Thr Tyr Ser Asp Asn Arg Tyr Gly Gly Thr
                260                 265                 270

Cys Asp Pro Asp Gly Cys Asp Trp Asp Pro Tyr Arg Leu Gly Asn Thr
            275                 280                 285

Ser Phe Tyr Gly Pro Gly Ser Ser Phe Thr Leu Asp Thr Thr Lys Lys
    290                 295                 300

Leu Thr Val Val Thr Gln Phe Glu Thr Ser Gly Ala Ile Asn Arg Tyr
305                 310                 315                 320

Tyr Val Gln Asn Gly Val Thr Phe Gln Gln Pro Asn Ala Glu Leu Gly
                325                 330                 335

Ser Tyr Ser Gly Asn Gly Leu Asn Asp Asp Tyr Cys Thr Ala Glu Glu
                340                 345                 350

Ala Glu Phe Gly Gly Ser Ser Phe Ser Asp Lys Gly Gly Leu Thr Gln
            355                 360                 365

Phe Lys Lys Ala Thr Ser Gly Gly Met Val Leu Val Met Ser Leu Trp
    370                 375                 380

Asp Asp Tyr Tyr Ala Asn Met Leu Trp Leu Asp Ser Thr Tyr Pro Thr
385                 390                 395                 400

Asn Glu Thr Ser Ser Thr Pro Gly Ala Val Arg Gly Ser Cys Ser Thr
                405                 410                 415

Ser Ser Gly Val Pro Ala Gln Val Glu Ser Gln Ser Pro Asn Ala Lys
                420                 425                 430

Val Thr Phe Ser Asn Ile Lys Phe Gly Pro Ile Gly Ser Thr Gly Asp
            435                 440                 445
```

```
Pro Ser Gly Gly Asn Pro Pro Gly Gly Asn Pro Pro Gly Thr Thr Thr
    450                 455                 460

Thr Arg Arg Pro Ala Thr Thr Thr Gly Ser Ser Pro Gly Pro Thr Gln
465                 470                 475                 480

Ser His Tyr Gly Gln Cys Gly Gly Ile Gly Tyr Ser Gly Pro Thr Val
                485                 490                 495

Cys Ala Ser Gly Thr Thr Cys Gln Val Leu Asn Pro Tyr Tyr Ser Gln
                500                 505                 510

Cys Leu

<210> SEQ ID NO 7
<211> LENGTH: 1572
<212> TYPE: DNA
<213> ORGANISM: Acremonium thermophilium
<220> FEATURE:
<221> NAME/KEY: CDS
<222> LOCATION: (1)..(1572)

<400> SEQUENCE: 7
```

| | | | | | | | | | | | | | | | | |
|---|---|---|---|---|---|---|---|---|---|---|---|---|---|---|---|---|
| atg | tat | acc | aag | ttc | gcc | gcc | ctc | gcc | gcc | ctc | gtg | gcc | acc | gtc | cgc | 48 |
| Met | Tyr | Thr | Lys | Phe | Ala | Ala | Leu | Ala | Ala | Leu | Val | Ala | Thr | Val | Arg | |
| 1 | | | | 5 | | | | | 10 | | | | | 15 | | |
| ggc | cag | gcc | gcc | tgc | tcg | ctc | acc | gcc | gag | acc | cac | ccg | tcg | ctg | cag | 96 |
| Gly | Gln | Ala | Ala | Cys | Ser | Leu | Thr | Ala | Glu | Thr | His | Pro | Ser | Leu | Gln | |
| | | | 20 | | | | | 25 | | | | | 30 | | | |
| tgg | cag | aag | tgc | acc | gcg | ccc | ggc | agc | tgc | acc | acc | gtc | agc | ggc | cag | 144 |
| Trp | Gln | Lys | Cys | Thr | Ala | Pro | Gly | Ser | Cys | Thr | Thr | Val | Ser | Gly | Gln | |
| | | 35 | | | | | 40 | | | | | 45 | | | | |
| gtc | acc | atc | gac | gcc | aac | tgg | cgc | tgg | ctg | cac | cag | acc | aac | agc | agc | 192 |
| Val | Thr | Ile | Asp | Ala | Asn | Trp | Arg | Trp | Leu | His | Gln | Thr | Asn | Ser | Ser | |
| | 50 | | | | | 55 | | | | | 60 | | | | | |
| acc | aac | tgc | tac | acc | ggc | aac | gag | tgg | gac | acc | agc | atc | tgc | agc | tcc | 240 |
| Thr | Asn | Cys | Tyr | Thr | Gly | Asn | Glu | Trp | Asp | Thr | Ser | Ile | Cys | Ser | Ser | |
| 65 | | | | | 70 | | | | | 75 | | | | | 80 | |
| gac | acc | gac | tgc | gcc | acc | aag | tgc | tgc | ctc | gac | ggc | gcc | gac | tac | acc | 288 |
| Asp | Thr | Asp | Cys | Ala | Thr | Lys | Cys | Cys | Leu | Asp | Gly | Ala | Asp | Tyr | Thr | |
| | | | | 85 | | | | | 90 | | | | | 95 | | |
| ggc | acc | tac | ggc | gtc | acc | gcc | agc | ggc | aac | tcg | ctc | aac | ctc | aag | ttc | 336 |
| Gly | Thr | Tyr | Gly | Val | Thr | Ala | Ser | Gly | Asn | Ser | Leu | Asn | Leu | Lys | Phe | |
| | | | 100 | | | | | 105 | | | | | 110 | | | |
| gtc | acc | cag | ggg | ccc | tac | tcc | aag | aac | atc | ggc | tcg | cgc | atg | tac | ctc | 384 |
| Val | Thr | Gln | Gly | Pro | Tyr | Ser | Lys | Asn | Ile | Gly | Ser | Arg | Met | Tyr | Leu | |
| | | 115 | | | | | 120 | | | | | 125 | | | | |
| atg | gag | tcg | gag | tcc | aag | tac | cag | ggc | ttc | act | ctc | ctc | ggt | cag | gag | 432 |
| Met | Glu | Ser | Glu | Ser | Lys | Tyr | Gln | Gly | Phe | Thr | Leu | Leu | Gly | Gln | Glu | |
| | 130 | | | | | 135 | | | | | 140 | | | | | |
| ttt | acc | ttt | gac | gtg | gac | gtc | tcc | aac | ctc | ggc | tgc | ggt | ctg | aac | gga | 480 |
| Phe | Thr | Phe | Asp | Val | Asp | Val | Ser | Asn | Leu | Gly | Cys | Gly | Leu | Asn | Gly | |
| 145 | | | | | 150 | | | | | 155 | | | | | 160 | |
| gcg | ctc | tac | ttc | gtg | tcc | atg | gac | ctc | gac | ggc | ggc | gtg | tcc | aag | tac | 528 |
| Ala | Leu | Tyr | Phe | Val | Ser | Met | Asp | Leu | Asp | Gly | Gly | Val | Ser | Lys | Tyr | |
| | | | | 165 | | | | | 170 | | | | | 175 | | |
| acc | acc | aac | aag | gcc | ggc | gcc | aag | tac | ggc | acc | ggc | tac | tgc | gac | tcc | 576 |
| Thr | Thr | Asn | Lys | Ala | Gly | Ala | Lys | Tyr | Gly | Thr | Gly | Tyr | Cys | Asp | Ser | |
| | | | 180 | | | | | 185 | | | | | 190 | | | |
| cag | tgc | ccg | cgg | gat | ctc | aag | ttc | atc | aac | ggc | cag | gcc | aac | atc | gac | 624 |
| Gln | Cys | Pro | Arg | Asp | Leu | Lys | Phe | Ile | Asn | Gly | Gln | Ala | Asn | Ile | Asp | |
| | | 195 | | | | | 200 | | | | | 205 | | | | |
| ggc | tgg | caa | ccg | tcg | tcc | aac | gac | gcc | aac | gcc | ggc | ctc | ggg | aac | cac | 672 |
| Gly | Trp | Gln | Pro | Ser | Ser | Asn | Asp | Ala | Asn | Ala | Gly | Leu | Gly | Asn | His | |

```
                    210                 215                 220
ggc agc tgc tgc tcc gag atg gac atc tgg gag gcc aac aag gtc tcc    720
Gly Ser Cys Cys Ser Glu Met Asp Ile Trp Glu Ala Asn Lys Val Ser
225                 230                 235                 240 gcc gcc tac acg ccg cac ccc tgc acc acc atc ggc cag acc atg tgc    768
Ala Ala Tyr Thr Pro His Pro Cys Thr Thr Ile Gly Gln Thr Met Cys
                245                 250                 255 acc ggc gac gac tgc ggc ggc acc tat tcg tcg gac cgc tat gcc ggc    816
Thr Gly Asp Asp Cys Gly Gly Thr Tyr Ser Ser Asp Arg Tyr Ala Gly
            260                 265                 270 atc tgc gac ccc gac ggt tgc gat ttt aac tcg tac cgc atg ggc gac    864
Ile Cys Asp Pro Asp Gly Cys Asp Phe Asn Ser Tyr Arg Met Gly Asp
        275                 280                 285 acc agc ttc tac ggc ccc ggc aag acg gtc gac acc ggc tcc aag ttc    912
Thr Ser Phe Tyr Gly Pro Gly Lys Thr Val Asp Thr Gly Ser Lys Phe
    290                 295                 300 acc gtc gtg acc cag ttc ctc acg ggc tcc gac ggc aac ctc agc gag    960
Thr Val Val Thr Gln Phe Leu Thr Gly Ser Asp Gly Asn Leu Ser Glu
305                 310                 315                 320 atc aag cgc ttc tac gtg cag aac ggc aag gtc atc ccc aac tcc gag    1008
Ile Lys Arg Phe Tyr Val Gln Asn Gly Lys Val Ile Pro Asn Ser Glu
                325                 330                 335 tcc aag atc gcc ggc gtc tcc ggc aac tcc atc acc acc gac ttc tgc    1056
Ser Lys Ile Ala Gly Val Ser Gly Asn Ser Ile Thr Thr Asp Phe Cys
                340                 345                 350 acc gcc cag aag acc gcc ttc ggc gac acc aac gtc ttc gag gag cgc    1104
Thr Ala Gln Lys Thr Ala Phe Gly Asp Thr Asn Val Phe Glu Glu Arg
            355                 360                 365 ggc ggc ctc gcc cag atg ggc aag gcc ctg gcc gag ccc atg gtc ctg    1152
Gly Gly Leu Ala Gln Met Gly Lys Ala Leu Ala Glu Pro Met Val Leu
370                 375                 380 gtc ctg tcc gtc tgg gac gac cac gcc gtc aac atg ctc tgg ctc gac    1200
Val Leu Ser Val Trp Asp Asp His Ala Val Asn Met Leu Trp Leu Asp
385                 390                 395                 400 tcc acc tac ccc acc gac agc acc aag ccc ggc gcc gcc cgc ggc gac    1248
Ser Thr Tyr Pro Thr Asp Ser Thr Lys Pro Gly Ala Ala Arg Gly Asp
                405                 410                 415 tgc ccc atc acc tcc ggc gtg ccc gcc gac gtc gag tcc cag gcg ccc    1296
Cys Pro Ile Thr Ser Gly Val Pro Ala Asp Val Glu Ser Gln Ala Pro
                420                 425                 430 aac tcc aac gtc atc tac tcc aac atc cgc ttc ggc ccc atc aac tcc    1344
Asn Ser Asn Val Ile Tyr Ser Asn Ile Arg Phe Gly Pro Ile Asn Ser
            435                 440                 445 acc tac acc ggc acc ccc agc ggc ggc aac ccc ccc ggc ggc ggg acc    1392
Thr Tyr Thr Gly Thr Pro Ser Gly Gly Asn Pro Pro Gly Gly Gly Thr
    450                 455                 460 acc acc acc acc acc acc acc tcc aag ccc tcc ggc ccc acc acc        1440
Thr Thr Thr Thr Thr Thr Thr Ser Lys Pro Ser Gly Pro Thr Thr
465                 470                 475                 480 acc acc aac ccc tcg ggt ccg cag cag acg cac tgg ggt cag tgc ggc    1488
Thr Thr Asn Pro Ser Gly Pro Gln Gln Thr His Trp Gly Gln Cys Gly
                485                 490                 495 ggc cag gga tgg acc ggc ccc acg gtc tgc cag agc ccc tac acc tgc    1536
Gly Gln Gly Trp Thr Gly Pro Thr Val Cys Gln Ser Pro Tyr Thr Cys
            500                 505                 510 aag tac tcc aac gac tgg tac tcg cag tgc ctg taa                    1572
Lys Tyr Ser Asn Asp Trp Tyr Ser Gln Cys Leu
        515                 520
```

<210> SEQ ID NO 8
<211> LENGTH: 523
<212> TYPE: PRT
<213> ORGANISM: Acremonium thermophilium

<400> SEQUENCE: 8

Met Tyr Thr Lys Phe Ala Ala Leu Ala Ala Leu Val Ala Thr Val Arg
1               5                   10                  15

Gly Gln Ala Ala Cys Ser Leu Thr Ala Glu Thr His Pro Ser Leu Gln
            20                  25                  30

Trp Gln Lys Cys Thr Ala Pro Gly Ser Cys Thr Thr Val Ser Gly Gln
        35                  40                  45

Val Thr Ile Asp Ala Asn Trp Arg Trp Leu His Gln Thr Asn Ser Ser
    50                  55                  60

Thr Asn Cys Tyr Thr Gly Asn Glu Trp Asp Thr Ser Ile Cys Ser Ser
65                  70                  75                  80

Asp Thr Asp Cys Ala Thr Lys Cys Cys Leu Asp Gly Ala Asp Tyr Thr
                85                  90                  95

Gly Thr Tyr Gly Val Thr Ala Ser Gly Asn Ser Leu Asn Leu Lys Phe
            100                 105                 110

Val Thr Gln Gly Pro Tyr Ser Lys Asn Ile Gly Ser Arg Met Tyr Leu
        115                 120                 125

Met Glu Ser Glu Ser Lys Tyr Gln Gly Phe Thr Leu Leu Gly Gln Glu
130                 135                 140

Phe Thr Phe Asp Val Asp Val Ser Asn Leu Gly Cys Gly Leu Asn Gly
145                 150                 155                 160

Ala Leu Tyr Phe Val Ser Met Asp Leu Asp Gly Val Ser Lys Tyr
                165                 170                 175

Thr Thr Asn Lys Ala Gly Ala Lys Tyr Gly Thr Gly Tyr Cys Asp Ser
            180                 185                 190

Gln Cys Pro Arg Asp Leu Lys Phe Ile Asn Gly Gln Ala Asn Ile Asp
        195                 200                 205

Gly Trp Gln Pro Ser Ser Asn Asp Ala Asn Ala Gly Leu Gly Asn His
    210                 215                 220

Gly Ser Cys Cys Ser Glu Met Asp Ile Trp Glu Ala Asn Lys Val Ser
225                 230                 235                 240

Ala Ala Tyr Thr Pro His Pro Cys Thr Thr Ile Gly Gln Thr Met Cys
                245                 250                 255

Thr Gly Asp Asp Cys Gly Gly Thr Tyr Ser Ser Asp Arg Tyr Ala Gly
            260                 265                 270

Ile Cys Asp Pro Asp Gly Cys Asp Phe Asn Ser Tyr Arg Met Gly Asp
        275                 280                 285

Thr Ser Phe Tyr Gly Pro Gly Lys Thr Val Asp Thr Gly Ser Lys Phe
    290                 295                 300

Thr Val Val Thr Gln Phe Leu Thr Gly Ser Asp Gly Asn Leu Ser Glu
305                 310                 315                 320

Ile Lys Arg Phe Tyr Val Gln Asn Gly Lys Val Ile Pro Asn Ser Glu
                325                 330                 335

Ser Lys Ile Ala Gly Val Ser Gly Asn Ser Ile Thr Thr Asp Phe Cys
            340                 345                 350

Thr Ala Gln Lys Thr Ala Phe Gly Asp Thr Asn Val Phe Glu Glu Arg
        355                 360                 365

Gly Gly Leu Ala Gln Met Gly Lys Ala Leu Ala Glu Pro Met Val Leu
    370                 375                 380

```
Val Leu Ser Val Trp Asp Asp His Ala Val Asn Met Leu Trp Leu Asp
385                 390                 395                 400

Ser Thr Tyr Pro Thr Asp Ser Thr Lys Pro Gly Ala Ala Arg Gly Asp
            405                 410                 415

Cys Pro Ile Thr Ser Gly Val Pro Ala Asp Val Glu Ser Gln Ala Pro
            420                 425                 430

Asn Ser Asn Val Ile Tyr Ser Asn Ile Arg Phe Gly Pro Ile Asn Ser
            435                 440                 445

Thr Tyr Thr Gly Thr Pro Ser Gly Gly Asn Pro Pro Gly Gly Gly Thr
            450                 455                 460

Thr Thr Thr Thr Thr Thr Thr Ser Lys Pro Ser Gly Pro Thr Thr
465                 470                 475                 480

Thr Thr Asn Pro Ser Gly Pro Gln Gln Thr His Trp Gly Gln Cys Gly
            485                 490                 495

Gly Gln Gly Trp Thr Gly Pro Thr Val Cys Gln Ser Pro Tyr Thr Cys
            500                 505                 510

Lys Tyr Ser Asn Asp Trp Tyr Ser Gln Cys Leu
            515                 520

<210> SEQ ID NO 9
<211> LENGTH: 1368
<212> TYPE: DNA
<213> ORGANISM: Talaromyces emersonii
<220> FEATURE:
<221> NAME/KEY: CDS
<222> LOCATION: (1)..(1368)

<400> SEQUENCE: 9 atg ctt cga cgg gct ctt ctt cta tcc tct tcc gcc atc ctt gct gtc        48
Met Leu Arg Arg Ala Leu Leu Leu Ser Ser Ser Ala Ile Leu Ala Val
1               5                   10                  15 aag gca cag cag gcc tgc acg gcg acg gca gag aac cac ccg ccc ctg        96
Lys Ala Gln Gln Ala Cys Thr Ala Thr Ala Glu Asn His Pro Pro Leu
                20                  25                  30 aca tgg cag gaa tgc acc gcc cct ggg agc tgc acc acc cag aac ggg       144
Thr Trp Gln Glu Cys Thr Ala Pro Gly Ser Cys Thr Thr Gln Asn Gly
            35                  40                  45 gcg gtc gtt ctt gat gcg aac tgg cgt tgg gtg cac gat gtg aac gga       192
Ala Val Val Leu Asp Ala Asn Trp Arg Trp Val His Asp Val Asn Gly
        50                  55                  60 tac acc aac tgc tac acg ggc aat acc tgg gac ccc acg tac tgc cct       240
Tyr Thr Asn Cys Tyr Thr Gly Asn Thr Trp Asp Pro Thr Tyr Cys Pro
65                  70                  75                  80 gac gac gaa acc tgc gcc cag aac tgt tgc ctg gac ggc gcg gat tac       288
Asp Asp Glu Thr Cys Ala Gln Asn Cys Cys Leu Asp Gly Ala Asp Tyr
                85                  90                  95 gag ggc acc tac ggc gtg act tcg tcg ggc agc tcc ttg aaa ctc aat       336
Glu Gly Thr Tyr Gly Val Thr Ser Ser Gly Ser Ser Leu Lys Leu Asn
            100                 105                 110 ttc gtc acc ggg tcg aac gtc gga tcc cgt ctc tac ctg ctg cag gac       384
Phe Val Thr Gly Ser Asn Val Gly Ser Arg Leu Tyr Leu Leu Gln Asp
        115                 120                 125 gac tcg acc tat cag atc ttc aag ctt ctg aac cgc gag ttc agc ttt       432
Asp Ser Thr Tyr Gln Ile Phe Lys Leu Leu Asn Arg Glu Phe Ser Phe
130                 135                 140 gac gtc gat gtc tcc aat ctt ccg tgc gga ttg aac ggc gct ctg tac       480
Asp Val Asp Val Ser Asn Leu Pro Cys Gly Leu Asn Gly Ala Leu Tyr
145                 150                 155                 160 ttt gtc gcc atg gac gcc gac ggc ggc gtg tcc aag tac ccg aac aac       528
Phe Val Ala Met Asp Ala Asp Gly Gly Val Ser Lys Tyr Pro Asn Asn
```

```
                Phe Val Ala Met Asp Ala Asp Gly Gly Val Ser Lys Tyr Pro Asn Asn
                                165                 170                 175 aag gct ggt gcc aag tac gga acc ggg tat tgc gac tcc caa tgc cca              576
Lys Ala Gly Ala Lys Tyr Gly Thr Gly Tyr Cys Asp Ser Gln Cys Pro
            180                 185                 190 cgg gac ctc aag ttc atc gac ggc gag gcc aac gtc gag ggc tgg cag              624
Arg Asp Leu Lys Phe Ile Asp Gly Glu Ala Asn Val Glu Gly Trp Gln
        195                 200                 205 ccg tct tcg aac aac gcc aac acc gga att ggc gac cac ggc tcc tgc              672
Pro Ser Ser Asn Asn Ala Asn Thr Gly Ile Gly Asp His Gly Ser Cys
    210                 215                 220 tgt gcg gag atg gat gtc tgg gaa gca aac agc atc tcc aat gcg gtc              720
Cys Ala Glu Met Asp Val Trp Glu Ala Asn Ser Ile Ser Asn Ala Val
225                 230                 235                 240 act ccg cac ccg tgc gac acg cca ggc cag acg atg tgc tct gga gat              768
Thr Pro His Pro Cys Asp Thr Pro Gly Gln Thr Met Cys Ser Gly Asp
                245                 250                 255 gac tgc ggt ggc aca tac tct aac gat cgc tac gcg gga acc tgc gat              816
Asp Cys Gly Gly Thr Tyr Ser Asn Asp Arg Tyr Ala Gly Thr Cys Asp
            260                 265                 270 cct gac ggc tgt gac ttc aac cct tac cgc atg ggc aac act tct ttc              864
Pro Asp Gly Cys Asp Phe Asn Pro Tyr Arg Met Gly Asn Thr Ser Phe
        275                 280                 285 tac ggg cct ggc aag atc atc gat acc acc aag ccc ttc act gtc gtg              912
Tyr Gly Pro Gly Lys Ile Ile Asp Thr Thr Lys Pro Phe Thr Val Val
    290                 295                 300 acg cag ttc ctc act gat gat ggt acg gat act gga act ctc agc gag              960
Thr Gln Phe Leu Thr Asp Asp Gly Thr Asp Thr Gly Thr Leu Ser Glu
305                 310                 315                 320 atc aag cgc ttc tac atc cag aac agc aac gtc att ccg cag ccc aac             1008
Ile Lys Arg Phe Tyr Ile Gln Asn Ser Asn Val Ile Pro Gln Pro Asn
                325                 330                 335 tcg gac atc agt ggc gtg acc ggc aac tcg atc acg acg gag ttc tgc             1056
Ser Asp Ile Ser Gly Val Thr Gly Asn Ser Ile Thr Thr Glu Phe Cys
            340                 345                 350 act gct cag aag cag gcc ttt ggc gac acg gac gac ttc tct cag cac             1104
Thr Ala Gln Lys Gln Ala Phe Gly Asp Thr Asp Asp Phe Ser Gln His
        355                 360                 365 ggt ggc ctg gcc aag atg gga gcg gcc atg cag cag ggt atg gtc ctg             1152
Gly Gly Leu Ala Lys Met Gly Ala Ala Met Gln Gln Gly Met Val Leu
    370                 375                 380 gtg atg agt ttg tgg gac gac tac gcc gcg cag atg ctg tgg ttg gat             1200
Val Met Ser Leu Trp Asp Asp Tyr Ala Ala Gln Met Leu Trp Leu Asp
385                 390                 395                 400 tcc gac tac ccg acg gat gcg gac ccc acg acc cct ggt att gcc cgt             1248
Ser Asp Tyr Pro Thr Asp Ala Asp Pro Thr Thr Pro Gly Ile Ala Arg
                405                 410                 415 gga acg tgt ccg acg gac tcg ggc gtc cca tcg gat gtc gag tcg cag             1296
Gly Thr Cys Pro Thr Asp Ser Gly Val Pro Ser Asp Val Glu Ser Gln
            420                 425                 430 agc ccc aac tcc tac gtg acc tac tcg aac att aag ttt ggt ccg atc             1344
Ser Pro Asn Ser Tyr Val Thr Tyr Ser Asn Ile Lys Phe Gly Pro Ile
        435                 440                 445 aac tcg acc ttc acc gct tcg tga                                              1368
Asn Ser Thr Phe Thr Ala Ser
    450                 455

<210> SEQ ID NO 10
<211> LENGTH: 455
<212> TYPE: PRT
```

<213> ORGANISM: Talaromyces emersonii

<400> SEQUENCE: 10

```
Met Leu Arg Arg Ala Leu Leu Leu Ser Ser Ser Ala Ile Leu Ala Val
 1               5                  10                  15

Lys Ala Gln Gln Ala Cys Thr Ala Thr Ala Glu Asn His Pro Pro Leu
            20                  25                  30

Thr Trp Gln Glu Cys Thr Ala Pro Gly Ser Cys Thr Thr Gln Asn Gly
        35                  40                  45

Ala Val Val Leu Asp Ala Asn Trp Arg Trp Val His Asp Val Asn Gly
    50                  55                  60

Tyr Thr Asn Cys Tyr Thr Gly Asn Thr Trp Asp Pro Thr Tyr Cys Pro
 65                  70                  75                  80

Asp Asp Glu Thr Cys Ala Gln Asn Cys Cys Leu Asp Gly Ala Asp Tyr
                85                  90                  95

Glu Gly Thr Tyr Gly Val Thr Ser Ser Gly Ser Ser Leu Lys Leu Asn
            100                 105                 110

Phe Val Thr Gly Ser Asn Val Gly Ser Arg Leu Tyr Leu Leu Gln Asp
        115                 120                 125

Asp Ser Thr Tyr Gln Ile Phe Lys Leu Leu Asn Arg Glu Phe Ser Phe
    130                 135                 140

Asp Val Asp Val Ser Asn Leu Pro Cys Gly Leu Asn Gly Ala Leu Tyr
145                 150                 155                 160

Phe Val Ala Met Asp Ala Asp Gly Gly Val Ser Lys Tyr Pro Asn Asn
                165                 170                 175

Lys Ala Gly Ala Lys Tyr Gly Thr Gly Tyr Cys Asp Ser Gln Cys Pro
            180                 185                 190

Arg Asp Leu Lys Phe Ile Asp Gly Glu Ala Asn Val Glu Gly Trp Gln
        195                 200                 205

Pro Ser Ser Asn Asn Ala Asn Thr Gly Ile Gly Asp His Gly Ser Cys
    210                 215                 220

Cys Ala Glu Met Asp Val Trp Glu Ala Asn Ser Ile Ser Asn Ala Val
225                 230                 235                 240

Thr Pro His Pro Cys Asp Thr Pro Gly Gln Thr Met Cys Ser Gly Asp
                245                 250                 255

Asp Cys Gly Gly Thr Tyr Ser Asn Asp Arg Tyr Ala Gly Thr Cys Asp
            260                 265                 270

Pro Asp Gly Cys Asp Phe Asn Pro Tyr Arg Met Gly Asn Thr Ser Phe
        275                 280                 285

Tyr Gly Pro Gly Lys Ile Ile Asp Thr Thr Lys Pro Phe Thr Val Val
    290                 295                 300

Thr Gln Phe Leu Thr Asp Asp Gly Thr Asp Thr Gly Thr Leu Ser Glu
305                 310                 315                 320

Ile Lys Arg Phe Tyr Ile Gln Asn Ser Asn Val Ile Pro Gln Pro Asn
                325                 330                 335

Ser Asp Ile Ser Gly Val Thr Gly Asn Ser Ile Thr Thr Glu Phe Cys
            340                 345                 350

Thr Ala Gln Lys Gln Ala Phe Gly Asp Thr Asp Phe Ser Gln His
        355                 360                 365

Gly Gly Leu Ala Lys Met Gly Ala Ala Met Gln Gln Gly Met Val Leu
    370                 375                 380

Val Met Ser Leu Trp Asp Asp Tyr Ala Ala Gln Met Leu Trp Leu Asp
385                 390                 395                 400
```

Ser Asp Tyr Pro Thr Asp Ala Asp Pro Thr Thr Pro Gly Ile Ala Arg
            405                 410                 415

Gly Thr Cys Pro Thr Asp Ser Gly Val Pro Ser Asp Val Glu Ser Gln
            420                 425                 430

Ser Pro Asn Ser Tyr Val Thr Tyr Ser Asn Ile Lys Phe Gly Pro Ile
            435                 440                 445

Asn Ser Thr Phe Thr Ala Ser
            450                 455

<210> SEQ ID NO 11
<211> LENGTH: 514
<212> TYPE: PRT
<213> ORGANISM: Chaetomium elatum

<400> SEQUENCE: 11

Gln Gln Ala Cys Ser Leu Thr Ala Glu Asn His Pro Ser Leu Thr Trp
1               5                   10                  15

Lys Arg Cys Thr Ser Gly Gly Ser Cys Ser Thr Val Asn Gly Ala Val
            20                  25                  30

Thr Ile Asp Ala Asn Trp Arg Trp Thr His Thr Val Ser Gly Ser Thr
        35                  40                  45

Asn Cys Tyr Thr Gly Asn Gln Trp Asp Thr Ser Leu Cys Thr Asp Gly
    50                  55                  60

Lys Ser Cys Ala Gln Thr Cys Cys Val Asp Gly Ala Asp Tyr Ser Ser
65                  70                  75                  80

Thr Tyr Gly Ile Thr Thr Ser Gly Asp Ser Leu Asn Leu Lys Phe Val
                85                  90                  95

Thr Lys His Gln Tyr Gly Thr Asn Val Gly Ser Arg Val Tyr Leu Met
            100                 105                 110

Glu Asn Asp Thr Lys Tyr Gln Met Phe Glu Leu Leu Gly Asn Glu Phe
        115                 120                 125

Thr Phe Asp Val Asp Val Ser Asn Leu Gly Cys Gly Leu Asn Gly Ala
    130                 135                 140

Leu Tyr Phe Val Ser Met Asp Ala Asp Gly Gly Met Ser Lys Tyr Ser
145                 150                 155                 160

Gly Asn Lys Ala Gly Ala Lys Tyr Gly Thr Gly Tyr Cys Asp Ala Gln
                165                 170                 175

Cys Pro Arg Asp Leu Lys Phe Ile Asn Gly Glu Ala Asn Val Gly Asn
            180                 185                 190

Trp Thr Pro Ser Thr Asn Asp Ala Asn Ala Gly Phe Gly Arg Tyr Gly
        195                 200                 205

Ser Cys Cys Ser Glu Met Asp Val Trp Glu Ala Asn Asn Met Ala Thr
    210                 215                 220

Ala Phe Thr Pro His Pro Cys Thr Thr Val Gly Gln Ser Arg Cys Glu
225                 230                 235                 240

Ala Asp Thr Cys Gly Gly Thr Tyr Ser Ser Asp Arg Tyr Ala Gly Val
                245                 250                 255

Cys Asp Pro Asp Gly Cys Asp Phe Asn Ala Tyr Arg Gln Gly Asp Lys
            260                 265                 270

Thr Phe Tyr Gly Lys Gly Met Thr Val Asp Thr Asn Lys Lys Met Thr
        275                 280                 285

Val Val Thr Gln Phe His Lys Asn Ser Ala Gly Val Leu Ser Glu Ile
    290                 295                 300

Lys Arg Phe Tyr Val Gln Asp Gly Lys Ile Ile Ala Asn Ala Glu Ser
305                 310                 315                 320

Lys Ile Pro Gly Asn Pro Gly Asn Ser Ile Thr Gln Glu Tyr Cys Asp
                325                 330                 335

Ala Gln Lys Val Ala Phe Ser Asn Thr Asp Asp Phe Asn Arg Lys Gly
            340                 345                 350

Gly Met Ala Gln Met Ser Lys Ala Leu Ala Gly Pro Met Val Leu Val
        355                 360                 365

Met Ser Val Trp Asp Asp His Tyr Ala Asn Met Leu Trp Leu Asp Ser
    370                 375                 380

Thr Tyr Pro Ile Asp Gln Ala Gly Ala Pro Gly Ala Glu Arg Gly Ala
385                 390                 395                 400

Cys Pro Thr Thr Ser Gly Val Pro Ala Glu Ile Glu Ala Gln Val Pro
                405                 410                 415

Asn Ser Asn Val Ile Phe Ser Asn Ile Arg Phe Gly Pro Ile Gly Ser
            420                 425                 430

Thr Val Pro Gly Leu Asp Gly Ser Asn Pro Gly Asn Pro Thr Thr Thr
        435                 440                 445

Val Val Pro Pro Ala Ser Thr Ser Thr Ser Arg Pro Thr Ser Ser Thr
    450                 455                 460

Ser Ser Pro Val Ser Thr Pro Thr Gly Gln Pro Gly Gly Cys Thr Thr
465                 470                 475                 480

Gln Lys Trp Gly Gln Cys Gly Gly Ile Gly Tyr Thr Gly Cys Thr Asn
                485                 490                 495

Cys Val Ala Gly Thr Thr Cys Thr Gln Leu Asn Pro Trp Tyr Ser Gln
            500                 505                 510

Cys Leu

<210> SEQ ID NO 12
<211> LENGTH: 501
<212> TYPE: PRT
<213> ORGANISM: Thermoascus aurantiacus

<400> SEQUENCE: 12

Gln Gln Ala Cys Thr Val Thr Ala Glu Asn His Pro Ser Leu Thr Trp
1               5                   10                  15

Gln Gln Cys Ser Ser Gly Gly Ser Cys Thr Thr Gln Asn Gly Lys Val
            20                  25                  30

Val Ile Asp Ala Asn Trp Arg Trp Val His Thr Thr Ser Gly Tyr Thr
        35                  40                  45

Asn Cys Tyr Thr Gly Asn Thr Trp Asp Thr Ser Ile Cys Pro Asp Asp
    50                  55                  60

Val Thr Cys Ala Gln Asn Cys Cys Leu Asp Gly Ala Asp Tyr Ser Gly
65                  70                  75                  80

Thr Tyr Gly Val Thr Thr Ser Gly Asn Ala Leu Arg Leu Asn Phe Val
                85                  90                  95

Thr Gln Ser Ser Gly Lys Asn Ile Gly Ser Arg Leu Tyr Leu Leu Gln
            100                 105                 110

Asp Asp Thr Thr Tyr Gln Ile Phe Lys Leu Leu Gly Gln Glu Phe Thr
        115                 120                 125

Phe Asp Val Asp Val Ser Asn Leu Pro Cys Gly Leu Asn Gly Ala Leu
    130                 135                 140

Tyr Phe Val Ala Met Asp Ala Asp Gly Gly Leu Ser Lys Tyr Pro Gly
145                 150                 155                 160

Asn Lys Ala Gly Ala Lys Tyr Gly Thr Gly Tyr Cys Asp Ser Gln Cys
                165                 170                 175

```
Pro Arg Asp Leu Lys Phe Ile Asn Gly Gln Ala Asn Val Glu Gly Trp
        180                 185                 190

Gln Pro Ser Ala Asn Asp Pro Asn Ala Gly Val Gly Asn His Gly Ser
            195                 200                 205

Cys Cys Ala Glu Met Asp Val Trp Glu Ala Asn Ser Ile Ser Thr Ala
210                 215                 220

Val Thr Pro His Pro Cys Asp Thr Pro Gly Gln Thr Met Cys Gln Gly
225                 230                 235                 240

Asp Asp Cys Gly Gly Thr Tyr Ser Ser Thr Arg Tyr Ala Gly Thr Cys
                245                 250                 255

Asp Pro Asp Gly Cys Asp Phe Asn Pro Tyr Arg Gln Gly Asn His Ser
            260                 265                 270

Phe Tyr Gly Pro Gly Gln Ile Val Asp Thr Ser Ser Lys Phe Thr Val
        275                 280                 285

Val Thr Gln Phe Ile Thr Asp Asp Gly Thr Pro Ser Gly Thr Leu Thr
    290                 295                 300

Glu Ile Lys Arg Phe Tyr Val Gln Asn Gly Lys Val Ile Pro Gln Ser
305                 310                 315                 320

Glu Ser Thr Ile Ser Gly Val Thr Gly Asn Ser Ile Thr Thr Glu Tyr
                325                 330                 335

Cys Thr Ala Gln Lys Ala Ala Phe Gly Asp Asn Thr Gly Phe Phe Thr
            340                 345                 350

His Gly Gly Leu Gln Lys Ile Ser Gln Ala Leu Ala Gln Gly Met Val
        355                 360                 365

Leu Val Met Ser Leu Trp Asp Asp His Ala Ala Asn Met Leu Trp Leu
    370                 375                 380

Asp Ser Thr Tyr Pro Thr Asp Ala Asp Pro Asp Thr Pro Gly Val Ala
385                 390                 395                 400

Arg Gly Thr Cys Pro Thr Thr Ser Gly Val Pro Ala Asp Val Glu Ser
                405                 410                 415

Gln Tyr Pro Asn Ser Tyr Val Ile Tyr Ser Asn Ile Lys Val Gly Pro
            420                 425                 430

Ile Asn Ser Thr Phe Thr Ala Asn Pro Pro Gly Gly Asn Pro Pro Gly
        435                 440                 445

Thr Thr Thr Thr Arg Arg Pro Ala Thr Thr Gly Ser Ser Pro Gly
    450                 455                 460

Pro Thr Gln Ser His Tyr Gly Gln Cys Gly Gly Ile Gly Tyr Ser Gly
465                 470                 475                 480

Pro Thr Val Cys Ala Ser Gly Thr Thr Cys Gln Val Leu Asn Pro Tyr
                485                 490                 495

Tyr Ser Gln Cys Leu
            500

<210> SEQ ID NO 13
<211> LENGTH: 497
<212> TYPE: PRT
<213> ORGANISM: Hypocrea jecorina

<400> SEQUENCE: 13

Gln Ser Ala Cys Thr Leu Gln Ser Glu Thr His Pro Pro Leu Thr Trp
1               5                   10                  15

Gln Lys Cys Ser Ser Gly Gly Thr Cys Thr Gln Gln Thr Gly Ser Val
            20                  25                  30

Val Ile Asp Ala Asn Trp Arg Trp Thr His Ala Thr Asn Ser Ser Thr
```

```
                35                  40                  45
Asn Cys Tyr Asp Gly Asn Thr Trp Ser Ser Thr Leu Cys Pro Asp Asn
                50                  55                  60
Glu Thr Cys Ala Lys Asn Cys Cys Leu Asp Gly Ala Ala Tyr Ala Ser
 65                 70                  75                  80
Thr Tyr Gly Val Thr Thr Ser Gly Asn Ser Leu Ser Ile Gly Phe Val
                    85                  90                  95
Thr Gln Ser Ala Gln Lys Asn Val Gly Ala Arg Leu Tyr Leu Met Ala
                100                 105                 110
Ser Asp Thr Thr Tyr Gln Glu Phe Thr Leu Leu Gly Asn Glu Phe Ser
                115                 120                 125
Phe Asp Val Asp Val Ser Gln Leu Pro Cys Gly Leu Asn Gly Ala Leu
                130                 135                 140
Tyr Phe Val Ser Met Asp Ala Asp Gly Gly Val Ser Lys Tyr Pro Thr
145                 150                 155                 160
Asn Thr Ala Gly Ala Lys Tyr Gly Thr Gly Tyr Cys Asp Ser Gln Cys
                165                 170                 175
Pro Arg Asp Leu Lys Phe Ile Asn Gly Gln Ala Asn Val Glu Gly Trp
                180                 185                 190
Glu Pro Ser Ser Asn Asn Ala Asn Thr Gly Ile Gly His Gly Ser
                195                 200                 205
Cys Cys Ser Glu Met Asp Ile Trp Glu Ala Asn Ser Ile Ser Glu Ala
210                 215                 220
Leu Thr Pro His Pro Cys Thr Thr Val Gly Gln Glu Ile Cys Glu Gly
225                 230                 235                 240
Asp Gly Cys Gly Gly Thr Tyr Ser Asp Asn Arg Tyr Gly Gly Thr Cys
                245                 250                 255
Asp Pro Asp Gly Cys Asp Trp Asn Pro Tyr Arg Leu Gly Asn Thr Ser
                260                 265                 270
Phe Tyr Gly Pro Gly Ser Ser Phe Thr Leu Asp Thr Thr Lys Lys Leu
                275                 280                 285
Thr Val Val Thr Gln Phe Glu Thr Ser Gly Ala Ile Asn Arg Tyr Tyr
                290                 295                 300
Val Gln Asn Gly Val Thr Phe Gln Gln Pro Asn Ala Glu Leu Gly Ser
305                 310                 315                 320
Tyr Ser Gly Asn Glu Leu Asn Asp Asp Tyr Cys Thr Ala Glu Glu Ala
                325                 330                 335
Glu Phe Gly Gly Ser Ser Phe Ser Asp Lys Gly Gly Leu Thr Gln Phe
                340                 345                 350
Lys Lys Ala Thr Ser Gly Gly Met Val Leu Val Met Ser Leu Trp Asp
                355                 360                 365
Asp Tyr Tyr Ala Asn Met Leu Trp Leu Asp Ser Thr Tyr Pro Thr Asn
                370                 375                 380
Glu Thr Ser Ser Thr Pro Gly Ala Val Arg Gly Ser Cys Ser Thr Ser
385                 390                 395                 400
Ser Gly Val Pro Ala Gln Val Glu Ser Gln Ser Pro Asn Ala Lys Val
                405                 410                 415
Thr Phe Ser Asn Ile Lys Phe Gly Pro Ile Gly Ser Thr Gly Asn Pro
                420                 425                 430
Ser Gly Gly Asn Pro Pro Gly Gly Asn Pro Pro Gly Thr Thr Thr Thr
                435                 440                 445
Arg Arg Pro Ala Thr Thr Thr Gly Ser Ser Pro Gly Pro Thr Gln Ser
450                 455                 460
```

```
His Tyr Gly Gln Cys Gly Ile Gly Tyr Ser Gly Pro Thr Val Cys
465                 470                 475                 480

Ala Ser Gly Thr Thr Cys Gln Val Leu Asn Pro Tyr Tyr Ser Gln Cys
            485                 490                 495

Leu

<210> SEQ ID NO 14
<211> LENGTH: 506
<212> TYPE: PRT
<213> ORGANISM: Acremonium. thermophilum

<400> SEQUENCE: 14

Gln Ala Ala Cys Ser Leu Thr Ala Glu Thr His Pro Ser Leu Gln Trp
1               5                   10                  15

Gln Lys Cys Thr Ala Pro Gly Ser Cys Thr Thr Val Ser Gly Gln Val
            20                  25                  30

Thr Ile Asp Ala Asn Trp Arg Trp Leu His Gln Thr Asn Ser Ser Thr
        35                  40                  45

Asn Cys Tyr Thr Gly Asn Glu Trp Asp Thr Ser Ile Cys Ser Ser Asp
50                  55                  60

Thr Asp Cys Ala Thr Lys Cys Cys Leu Asp Gly Ala Asp Tyr Thr Gly
65                  70                  75                  80

Thr Tyr Gly Val Thr Ala Ser Gly Asn Ser Leu Asn Leu Lys Phe Val
                85                  90                  95

Thr Gln Gly Pro Tyr Ser Lys Asn Ile Gly Ser Arg Met Tyr Leu Met
            100                 105                 110

Glu Ser Glu Ser Lys Tyr Gln Gly Phe Thr Leu Leu Gly Gln Glu Phe
        115                 120                 125

Thr Phe Asp Val Asp Val Ser Asn Leu Gly Cys Gly Leu Asn Gly Ala
130                 135                 140

Leu Tyr Phe Val Ser Met Asp Leu Asp Gly Gly Val Ser Lys Tyr Thr
145                 150                 155                 160

Thr Asn Lys Ala Gly Ala Lys Tyr Gly Thr Gly Tyr Cys Asp Ser Gln
                165                 170                 175

Cys Pro Arg Asp Leu Lys Phe Ile Asn Gly Gln Ala Asn Ile Asp Gly
            180                 185                 190

Trp Gln Pro Ser Ser Asn Asp Ala Asn Ala Gly Leu Gly Asn His Gly
        195                 200                 205

Ser Cys Cys Ser Glu Met Asp Ile Trp Glu Ala Asn Lys Val Ser Ala
210                 215                 220

Ala Tyr Thr Pro His Pro Cys Thr Thr Ile Gly Gln Thr Met Cys Thr
225                 230                 235                 240

Gly Asp Asp Cys Gly Gly Thr Tyr Ser Ser Asp Arg Tyr Ala Gly Ile
                245                 250                 255

Cys Asp Pro Asp Gly Cys Asp Phe Asn Ser Tyr Arg Met Gly Asp Thr
            260                 265                 270

Ser Phe Tyr Gly Pro Gly Lys Thr Val Asp Thr Gly Ser Lys Phe Thr
        275                 280                 285

Val Val Thr Gln Phe Leu Thr Gly Ser Asp Gly Asn Leu Ser Glu Ile
290                 295                 300

Lys Arg Phe Tyr Val Gln Asn Gly Lys Val Ile Pro Asn Ser Glu Ser
305                 310                 315                 320

Lys Ile Ala Gly Val Ser Gly Asn Ser Ile Thr Thr Asp Phe Cys Thr
                325                 330                 335
```

-continued

```
Ala Gln Lys Thr Ala Phe Gly Asp Thr Asn Val Phe Glu Glu Arg Gly
            340                 345                 350

Gly Leu Ala Gln Met Gly Lys Ala Leu Ala Glu Pro Met Val Leu Val
            355                 360                 365

Leu Ser Val Trp Asp Asp His Ala Val Asn Met Leu Trp Leu Asp Ser
    370                 375                 380

Thr Tyr Pro Thr Asp Ser Thr Lys Pro Gly Ala Ala Arg Gly Asp Cys
385                 390                 395                 400

Pro Ile Thr Ser Gly Val Pro Ala Asp Val Glu Ser Gln Ala Pro Asn
                405                 410                 415

Ser Asn Val Ile Tyr Ser Asn Ile Arg Phe Gly Pro Ile Asn Ser Thr
                420                 425                 430

Tyr Thr Gly Thr Pro Ser Gly Gly Asn Pro Pro Gly Gly Thr Thr
                435                 440                 445

Thr Thr Thr Thr Thr Thr Ser Lys Pro Ser Gly Pro Thr Thr Thr
    450                 455                 460

Thr Asn Pro Ser Gly Pro Gln Gln Thr His Trp Gly Gln Cys Gly Gly
465                 470                 475                 480

Gln Gly Trp Thr Gly Pro Thr Val Cys Gln Ser Pro Tyr Thr Cys Lys
                485                 490                 495

Tyr Ser Asn Asp Trp Tyr Ser Gln Cys Leu
                500                 505

<210> SEQ ID NO 15
<211> LENGTH: 498
<212> TYPE: PRT
<213> ORGANISM: Talaromyces emersonii

<400> SEQUENCE: 15

Gln Gln Ala Cys Thr Ala Thr Ala Glu Asn His Pro Pro Leu Thr Trp
1               5                   10                  15

Gln Glu Cys Thr Ala Pro Gly Ser Cys Thr Thr Gln Asn Gly Ala Val
                20                  25                  30

Val Leu Asp Ala Asn Trp Arg Trp Val His Asp Val Asn Gly Tyr Thr
            35                  40                  45

Asn Cys Tyr Thr Gly Asn Thr Trp Asp Pro Thr Tyr Cys Pro Asp Asp
    50                  55                  60

Glu Thr Cys Ala Gln Asn Cys Cys Leu Asp Gly Ala Asp Tyr Glu Gly
65                  70                  75                  80

Thr Tyr Gly Val Thr Ser Ser Gly Ser Ser Leu Lys Leu Asn Phe Val
                85                  90                  95

Thr Gly Ser Asn Val Gly Ser Arg Leu Tyr Leu Leu Gln Asp Asp Ser
                100                 105                 110

Thr Tyr Gln Ile Phe Lys Leu Leu Asn Arg Glu Phe Ser Phe Asp Val
            115                 120                 125

Asp Val Ser Asn Leu Pro Cys Gly Leu Asn Gly Ala Leu Tyr Phe Val
    130                 135                 140

Ala Met Asp Ala Asp Gly Gly Val Ser Lys Tyr Pro Asn Asn Lys Ala
145                 150                 155                 160

Gly Ala Lys Tyr Gly Thr Gly Tyr Cys Asp Ser Gln Cys Pro Arg Asp
                165                 170                 175

Leu Lys Phe Ile Asp Gly Glu Ala Asn Val Glu Gly Trp Gln Pro Ser
            180                 185                 190

Ser Asn Asn Ala Asn Thr Gly Ile Gly Asp His Gly Ser Cys Cys Ala
```

```
                195                 200                 205
Glu Met Asp Val Trp Glu Ala Asn Ser Ile Ser Asn Ala Val Thr Pro
210                 215                 220

His Pro Cys Asp Thr Pro Gly Gln Thr Met Cys Ser Gly Asp Cys
225                 230                 235                 240

Gly Gly Thr Tyr Ser Asn Asp Arg Tyr Ala Gly Thr Cys Asp Pro Asp
                245                 250                 255

Gly Cys Asp Phe Asn Pro Tyr Arg Met Gly Asn Thr Ser Phe Tyr Gly
            260                 265                 270

Pro Gly Lys Ile Ile Asp Thr Thr Lys Pro Phe Thr Val Val Thr Gln
        275                 280                 285

Phe Leu Thr Asp Asp Gly Thr Asp Thr Gly Thr Leu Ser Glu Ile Lys
290                 295                 300

Arg Phe Tyr Ile Gln Asn Ser Asn Val Ile Pro Gln Pro Asn Ser Asp
305                 310                 315                 320

Ile Ser Gly Val Thr Gly Asn Ser Ile Thr Thr Glu Phe Cys Thr Ala
                325                 330                 335

Gln Lys Gln Ala Phe Gly Asp Thr Asp Asp Phe Ser Gln His Gly Gly
            340                 345                 350

Leu Ala Lys Met Gly Ala Ala Met Gln Gln Gly Met Val Leu Val Met
        355                 360                 365

Ser Leu Trp Asp Asp Tyr Ala Ala Gln Met Leu Trp Leu Asp Ser Asp
370                 375                 380

Tyr Pro Thr Asp Ala Asp Pro Thr Thr Pro Gly Ile Ala Arg Gly Thr
385                 390                 395                 400

Cys Pro Thr Asp Ser Gly Val Pro Ser Asp Val Glu Ser Gln Ser Pro
                405                 410                 415

Asn Ser Tyr Val Thr Tyr Ser Asn Ile Lys Phe Gly Pro Ile Asn Ser
            420                 425                 430

Thr Phe Thr Ala Ser Pro Pro Gly Gly Asn Pro Pro Gly Thr Thr Thr
        435                 440                 445

Thr Arg Arg Pro Ala Thr Thr Thr Gly Ser Ser Pro Gly Pro Thr Gln
450                 455                 460

Ser His Tyr Gly Gln Cys Gly Gly Ile Gly Tyr Ser Gly Pro Thr Val
465                 470                 475                 480

Cys Ala Ser Gly Thr Thr Cys Gln Val Leu Asn Pro Tyr Tyr Ser Gln
                485                 490                 495

Cys Leu

<210> SEQ ID NO 16
<211> LENGTH: 78
<212> TYPE: PRT
<213> ORGANISM: Artificial Sequence
<220> FEATURE:
<223> OTHER INFORMATION: Linker and Cellulose Binding Moiety from C.
      thermophilum

<400> SEQUENCE: 16

Leu Asp Gly Ser Asn Pro Gly Asn Pro Thr Thr Thr Val Pro Pro
1               5                   10                  15

Ala Ser Thr Ser Thr Ser Arg Pro Thr Ser Ser Thr Ser Ser Pro Val
                20                  25                  30

Ser Thr Pro Thr Gly Gln Pro Gly Gly Cys Thr Thr Gln Lys Trp Gly
            35                  40                  45

Gln Cys Gly Gly Ile Gly Tyr Thr Gly Cys Thr Asn Cys Val Ala Gly
```

```
                    50                  55                  60
Thr Thr Cys Thr Gln Leu Asn Pro Trp Tyr Ser Gln Cys Leu
 65                  70                  75

<210> SEQ ID NO 17
<211> LENGTH: 61
<212> TYPE: PRT
<213> ORGANISM: Artificial Sequence
<220> FEATURE:
<223> OTHER INFORMATION: Linker and Cellulose Binding Moiety from H.
      jecorina

<400> SEQUENCE: 17

Pro Pro Gly Gly Asn Pro Pro Gly Thr Thr Thr Arg Arg Pro Ala
 1               5                  10                  15

Thr Thr Thr Gly Ser Ser Pro Gly Pro Thr Gln Ser His Tyr Gly Gln
                20                  25                  30

Cys Gly Gly Ile Gly Tyr Ser Gly Pro Thr Val Cys Ala Ser Gly Thr
            35                  40                  45

Thr Cys Gln Val Leu Asn Pro Tyr Tyr Ser Gln Cys Leu
        50                  55                  60

<210> SEQ ID NO 18
<211> LENGTH: 70
<212> TYPE: PRT
<213> ORGANISM: Artificial Sequence
<220> FEATURE:
<223> OTHER INFORMATION: Linker and Cellulose Binding Moiety from
      Acremonium thermophilum

<400> SEQUENCE: 18

Pro Ser Gly Gly Asn Pro Pro Gly Gly Gly Thr Thr Thr Thr Thr
 1               5                  10                  15

Thr Thr Thr Ser Lys Pro Ser Gly Pro Thr Thr Thr Thr Asn Pro Ser
                20                  25                  30

Gly Pro Gln Gln Thr His Trp Gly Gln Cys Gly Gly Gln Gly Trp Thr
            35                  40                  45

Gly Pro Thr Val Cys Gln Ser Pro Tyr Thr Cys Lys Tyr Ser Asn Asp
        50                  55                  60

Trp Tyr Ser Gln Cys Leu
 65                  70

<210> SEQ ID NO 19
<211> LENGTH: 441
<212> TYPE: PRT
<213> ORGANISM: Artificial Sequence
<220> FEATURE:
<223> OTHER INFORMATION: Chimeric polypeptide 34152252

<400> SEQUENCE: 19

Gln Ser Ala Cys Thr Leu Gln Ser Glu Thr His Pro Pro Leu Thr Trp
 1               5                  10                  15

Gln Lys Cys Ser Ser Gly Gly Thr Cys Thr Gln Gln Thr Gly Ser Val
                20                  25                  30

Thr Ile Asp Ala Asn Trp Arg Trp Leu His Gln Thr Asn Ser Ser Thr
            35                  40                  45

Asn Cys Tyr Thr Gly Asn Glu Trp Asp Thr Ser Ile Cys Ser Ser Asp
        50                  55                  60

Thr Asp Cys Ala Thr Lys Cys Cys Leu Asp Gly Ala Asp Tyr Ser Ser
 65                  70                  75                  80
```

```
Thr Tyr Gly Ile Thr Thr Ser Gly Asp Ser Leu Asn Leu Lys Phe Val
            85                  90                  95

Thr Lys His Gln Tyr Gly Thr Asn Val Gly Ser Arg Val Tyr Leu Leu
        100                 105                 110

Gln Asp Asp Ser Thr Tyr Gln Ile Phe Lys Leu Leu Asn Arg Glu Phe
        115                 120                 125

Ser Phe Asp Val Asp Val Ser Asn Leu Pro Cys Gly Leu Asn Gly Ala
130                 135                 140

Leu Tyr Phe Val Ala Met Asp Ala Asp Gly Val Ser Lys Tyr Pro
145                 150                 155                 160

Gly Asn Lys Ala Gly Ala Lys Tyr Gly Thr Gly Tyr Cys Asp Ser Gln
                165                 170                 175

Cys Pro Arg Asp Leu Lys Phe Ile Asn Gly Gln Ala Asn Val Glu Gly
        180                 185                 190

Trp Gln Pro Ser Ala Asn Asp Pro Asn Ala Gly Val Gly Asn His Gly
        195                 200                 205

Ser Cys Cys Ala Glu Met Asp Val Trp Glu Ala Asn Ser Ile Ser Thr
210                 215                 220

Ala Val Thr Pro His Pro Cys Asp Thr Pro Gly Gln Thr Met Cys Gln
225                 230                 235                 240

Gly Asp Asp Cys Gly Gly Thr Tyr Ser Ser Thr Arg Tyr Ala Gly Thr
                245                 250                 255

Cys Asp Pro Asp Gly Cys Asp Phe Asn Pro Tyr Arg Met Gly Asn Thr
        260                 265                 270

Ser Phe Tyr Gly Pro Gly Lys Ile Ile Asp Thr Thr Lys Pro Phe Thr
        275                 280                 285

Val Val Thr Gln Phe Leu Thr Asp Asp Gly Thr Asp Thr Gly Thr Leu
290                 295                 300

Ser Glu Ile Lys Arg Phe Tyr Ile Gln Asn Ser Asn Val Ile Pro Gln
305                 310                 315                 320

Pro Asn Ser Asp Ile Ser Gly Val Thr Gly Asn Ser Ile Thr Thr Glu
                325                 330                 335

Phe Cys Thr Ala Gln Lys Gln Ala Phe Gly Asp Thr Asp Asp Phe Ser
        340                 345                 350

Gln His Gly Gly Leu Ala Lys Met Gly Ala Ala Met Gln Gln Gly Met
        355                 360                 365

Val Leu Val Met Ser Leu Trp Asp Asp His Ala Ala Asn Met Leu Trp
370                 375                 380

Leu Asp Ser Thr Tyr Pro Thr Asp Ala Asp Pro Asp Thr Pro Gly Val
385                 390                 395                 400

Ala Arg Gly Thr Cys Pro Thr Thr Ser Gly Val Pro Ala Asp Val Glu
                405                 410                 415

Ser Gln Tyr Pro Asn Ser Tyr Val Ile Tyr Ser Asn Ile Lys Val Gly
        420                 425                 430

Pro Ile Asn Ser Thr Phe Thr Ala Asn
        435                 440
```

<210> SEQ ID NO 20
<211> LENGTH: 441
<212> TYPE: PRT
<213> ORGANISM: Artificial Sequence
<220> FEATURE:
<223> OTHER INFORMATION: Chimeric polypeptide 55153552

<400> SEQUENCE: 20

-continued

```
Gln Gln Ala Cys Thr Ala Thr Ala Glu Asn His Pro Pro Leu Thr Trp
  1               5                  10                 15
Gln Glu Cys Thr Ala Pro Gly Ser Cys Thr Thr Gln Asn Gly Ala Val
             20                  25                  30
Val Leu Asp Ala Asn Trp Arg Trp Val His Asp Val Asn Gly Tyr Thr
         35                  40                  45
Asn Cys Tyr Thr Gly Asn Thr Trp Asp Pro Thr Tyr Cys Pro Asp Asp
     50                  55                  60
Glu Thr Cys Ala Gln Asn Cys Cys Leu Asp Gly Ala Asp Tyr Ser Ser
 65                  70                  75                  80
Thr Tyr Gly Ile Thr Thr Ser Gly Asp Ser Leu Asn Leu Lys Phe Val
                 85                  90                  95
Thr Lys His Gln Tyr Gly Thr Asn Val Gly Ser Arg Val Tyr Leu Leu
             100                 105                 110
Gln Asp Asp Ser Thr Tyr Gln Ile Phe Lys Leu Leu Asn Arg Glu Phe
         115                 120                 125
Ser Phe Asp Val Asp Val Ser Asn Leu Pro Cys Gly Leu Asn Gly Ala
     130                 135                 140
Leu Tyr Phe Val Ala Met Asp Ala Asp Gly Gly Val Ser Lys Tyr Pro
145                 150                 155                 160
Thr Asn Thr Ala Gly Ala Lys Tyr Gly Thr Gly Tyr Cys Asp Ser Gln
                 165                 170                 175
Cys Pro Arg Asp Leu Lys Phe Ile Asn Gly Gln Ala Asn Val Glu Gly
             180                 185                 190
Trp Glu Pro Ser Ser Asn Asn Ala Asn Thr Gly Ile Gly Asp His Gly
         195                 200                 205
Ser Cys Cys Ala Glu Met Asp Val Trp Glu Ala Asn Ser Ile Ser Asn
     210                 215                 220
Ala Val Thr Pro His Pro Cys Asp Thr Pro Gly Gln Thr Met Cys Ser
225                 230                 235                 240
Gly Asp Asp Cys Gly Gly Thr Tyr Ser Asn Asp Arg Tyr Ala Gly Thr
                 245                 250                 255
Cys Asp Pro Asp Gly Cys Asp Phe Asn Pro Tyr Arg Met Gly Asn Thr
             260                 265                 270
Ser Phe Tyr Gly Pro Gly Lys Ile Ile Asp Thr Thr Lys Pro Phe Thr
         275                 280                 285
Val Val Thr Gln Phe Leu Thr Asp Asp Gly Thr Asp Thr Gly Thr Leu
     290                 295                 300
Ser Glu Ile Lys Arg Phe Tyr Ile Gln Asn Ser Asn Val Ile Pro Gln
305                 310                 315                 320
Pro Asn Ser Asp Ile Ser Gly Val Thr Gly Asn Ser Ile Thr Thr Glu
                 325                 330                 335
Phe Cys Thr Ala Gln Lys Gln Ala Phe Gly Asp Thr Asp Asp Phe Ser
             340                 345                 350
Gln His Gly Gly Leu Ala Lys Met Gly Ala Ala Met Gln Gln Gly Met
         355                 360                 365
Val Leu Val Met Ser Leu Trp Asp Asp His Ala Ala Asn Met Leu Trp
     370                 375                 380
Leu Asp Ser Thr Tyr Pro Thr Asp Ala Asp Pro Asp Thr Pro Gly Val
385                 390                 395                 400
Ala Arg Gly Thr Cys Pro Thr Thr Ser Gly Val Pro Ala Asp Val Glu
                 405                 410                 415
Ser Gln Tyr Pro Asn Ser Tyr Val Ile Tyr Ser Asn Ile Lys Val Gly
```

420                 425                 430
Pro Ile Asn Ser Thr Phe Thr Ala Asn
            435                 440

<210> SEQ ID NO 21
<211> LENGTH: 441
<212> TYPE: PRT
<213> ORGANISM: Artificial Sequence
<220> FEATURE:
<223> OTHER INFORMATION: Chimeric polypeptide 32153252

<400> SEQUENCE: 21

Gln Ser Ala Cys Thr Leu Gln Ser Glu Thr His Pro Pro Leu Thr Trp
1               5                   10                  15

Gln Lys Cys Ser Ser Gly Gly Thr Cys Thr Gln Gln Thr Gly Ser Val
            20                  25                  30

Val Ile Asp Ala Asn Trp Arg Trp Val His Thr Thr Ser Gly Tyr Thr
        35                  40                  45

Asn Cys Tyr Thr Gly Asn Thr Trp Asp Thr Ser Ile Cys Pro Asp Asp
    50                  55                  60

Val Thr Cys Ala Gln Asn Cys Cys Leu Asp Gly Ala Asp Tyr Ser Ser
65                  70                  75                  80

Thr Tyr Gly Ile Thr Thr Ser Gly Asp Ser Leu Asn Leu Lys Phe Val
                85                  90                  95

Thr Lys His Gln Tyr Gly Thr Asn Val Gly Ser Arg Val Tyr Leu Leu
            100                 105                 110

Gln Asp Asp Ser Thr Tyr Gln Ile Phe Lys Leu Leu Asn Arg Glu Phe
        115                 120                 125

Ser Phe Asp Val Asp Val Ser Asn Leu Pro Cys Gly Leu Asn Gly Ala
    130                 135                 140

Leu Tyr Phe Val Ala Met Asp Ala Asp Gly Gly Val Ser Lys Tyr Pro
145                 150                 155                 160

Thr Asn Thr Ala Gly Ala Lys Tyr Gly Thr Gly Tyr Cys Asp Ser Gln
                165                 170                 175

Cys Pro Arg Asp Leu Lys Phe Ile Asn Gly Gln Ala Asn Val Glu Gly
            180                 185                 190

Trp Glu Pro Ser Ser Asn Asn Ala Asn Thr Gly Ile Gly Asn His Gly
        195                 200                 205

Ser Cys Cys Ala Glu Met Asp Val Trp Glu Ala Asn Ser Ile Ser Thr
    210                 215                 220

Ala Val Thr Pro His Pro Cys Asp Thr Pro Gly Gln Thr Met Cys Gln
225                 230                 235                 240

Gly Asp Asp Cys Gly Gly Thr Tyr Ser Ser Thr Arg Tyr Ala Gly Thr
                245                 250                 255

Cys Asp Pro Asp Gly Cys Asp Phe Asn Pro Tyr Arg Met Gly Asn Thr
            260                 265                 270

Ser Phe Tyr Gly Pro Gly Lys Ile Ile Asp Thr Thr Lys Pro Phe Thr
        275                 280                 285

Val Val Thr Gln Phe Leu Thr Asp Asp Gly Thr Asp Thr Gly Thr Leu
    290                 295                 300

Ser Glu Ile Lys Arg Phe Tyr Ile Gln Asn Ser Asn Val Ile Pro Gln
305                 310                 315                 320

Pro Asn Ser Asp Ile Ser Gly Val Thr Gly Asn Ser Ile Thr Thr Glu
                325                 330                 335

Phe Cys Thr Ala Gln Lys Gln Ala Phe Gly Asp Thr Asp Asp Phe Ser

```
                340             345             350
Gln His Gly Gly Leu Ala Lys Met Gly Ala Ala Met Gln Gln Gly Met
            355             360             365

Val Leu Val Met Ser Leu Trp Asp Asp His Ala Ala Asn Met Leu Trp
        370             375             380

Leu Asp Ser Thr Tyr Pro Thr Asp Ala Asp Pro Asp Thr Pro Gly Val
385             390             395             400

Ala Arg Gly Thr Cys Pro Thr Thr Ser Gly Val Pro Ala Asp Val Glu
            405             410             415

Ser Gln Tyr Pro Asn Ser Tyr Val Ile Tyr Ser Asn Ile Lys Val Gly
        420             425             430

Pro Ile Asn Ser Thr Phe Thr Ala Asn
        435             440

<210> SEQ ID NO 22
<211> LENGTH: 441
<212> TYPE: PRT
<213> ORGANISM: Artificial Sequence
<220> FEATURE:
<223> OTHER INFORMATION: Chimeric polypeptide 55155552

<400> SEQUENCE: 22

Gln Gln Ala Cys Thr Ala Thr Ala Glu Asn His Pro Pro Leu Thr Trp
1               5                   10                  15

Gln Glu Cys Thr Ala Pro Gly Ser Cys Thr Thr Gln Asn Gly Ala Val
            20                  25                  30

Val Leu Asp Ala Asn Trp Arg Trp Val His Asp Val Asn Gly Tyr Thr
        35                  40                  45

Asn Cys Tyr Thr Gly Asn Thr Trp Asp Pro Thr Tyr Cys Pro Asp Asp
    50                  55                  60

Glu Thr Cys Ala Gln Asn Cys Cys Leu Asp Gly Ala Asp Tyr Ser Ser
65                  70                  75                  80

Thr Tyr Gly Ile Thr Thr Ser Gly Asp Ser Leu Asn Leu Lys Phe Val
                85                  90                  95

Thr Lys His Gln Tyr Gly Thr Asn Val Gly Ser Arg Val Tyr Leu Leu
            100                 105                 110

Gln Asp Asp Ser Thr Tyr Gln Ile Phe Lys Leu Leu Asn Arg Glu Phe
        115                 120                 125

Ser Phe Asp Val Asp Val Ser Asn Leu Pro Cys Gly Leu Asn Gly Ala
    130                 135                 140

Leu Tyr Phe Val Ala Met Asp Ala Asp Gly Gly Val Ser Lys Tyr Pro
145                 150                 155                 160

Asn Asn Lys Ala Gly Ala Lys Tyr Gly Thr Gly Tyr Cys Asp Ser Gln
                165                 170                 175

Cys Pro Arg Asp Leu Lys Phe Ile Asp Gly Glu Ala Asn Val Glu Gly
            180                 185                 190

Trp Gln Pro Ser Ser Asn Asn Ala Asn Thr Gly Ile Gly Asp His Gly
        195                 200                 205

Ser Cys Cys Ala Glu Met Asp Val Trp Glu Ala Asn Ser Ile Ser Asn
    210                 215                 220

Ala Val Thr Pro His Pro Cys Asp Thr Pro Gly Gln Thr Met Cys Ser
225                 230                 235                 240

Gly Asp Asp Cys Gly Gly Thr Tyr Ser Asn Asp Arg Tyr Ala Gly Thr
                245                 250                 255

Cys Asp Pro Asp Gly Cys Asp Phe Asn Pro Tyr Arg Met Gly Asn Thr
```

```
                   260                 265                 270
Ser Phe Tyr Gly Pro Gly Lys Ile Ile Asp Thr Thr Lys Pro Phe Thr
               275                 280                 285

Val Val Thr Gln Phe Leu Thr Asp Asp Gly Thr Asp Thr Gly Thr Leu
           290                 295                 300

Ser Glu Ile Lys Arg Phe Tyr Ile Gln Asn Ser Asn Val Ile Pro Gln
305                 310                 315                 320

Pro Asn Ser Asp Ile Ser Gly Val Thr Gly Asn Ser Ile Thr Thr Glu
                325                 330                 335

Phe Cys Thr Ala Gln Lys Gln Ala Phe Gly Asp Thr Asp Asp Phe Ser
            340                 345                 350

Gln His Gly Gly Leu Ala Lys Met Gly Ala Ala Met Gln Gln Gly Met
            355                 360                 365

Val Leu Val Met Ser Leu Trp Asp Asp His Ala Ala Asn Met Leu Trp
        370                 375                 380

Leu Asp Ser Thr Tyr Pro Thr Asp Ala Asp Pro Asp Thr Pro Gly Val
385                 390                 395                 400

Ala Arg Gly Thr Cys Pro Thr Thr Ser Gly Val Pro Ala Asp Val Glu
                405                 410                 415

Ser Gln Tyr Pro Asn Ser Tyr Val Ile Tyr Ser Asn Ile Lys Val Gly
            420                 425                 430

Pro Ile Asn Ser Thr Phe Thr Ala Asn
            435                 440

<210> SEQ ID NO 23
<211> LENGTH: 441
<212> TYPE: PRT
<213> ORGANISM: Artificial Sequence
<220> FEATURE:
<223> OTHER INFORMATION: Chimeric polypeptide 22153252

<400> SEQUENCE: 23

Gln Gln Ala Cys Thr Val Thr Ala Glu Asn His Pro Ser Leu Thr Trp
1               5                   10                  15

Gln Gln Cys Ser Ser Gly Gly Ser Cys Thr Thr Gln Asn Gly Lys Val
                20                  25                  30

Val Ile Asp Ala Asn Trp Arg Trp Val His Thr Thr Ser Gly Tyr Thr
            35                  40                  45

Asn Cys Tyr Thr Gly Asn Thr Trp Asp Thr Ser Ile Cys Pro Asp Asp
        50                  55                  60

Val Thr Cys Ala Gln Asn Cys Cys Leu Asp Gly Ala Asp Tyr Ser Ser
65                  70                  75                  80

Thr Tyr Gly Ile Thr Thr Ser Gly Asp Ser Leu Asn Leu Lys Phe Val
                85                  90                  95

Thr Lys His Gln Tyr Gly Thr Asn Val Gly Ser Arg Val Tyr Leu Leu
            100                 105                 110

Gln Asp Asp Ser Thr Tyr Gln Ile Phe Lys Leu Leu Asn Arg Glu Phe
        115                 120                 125

Ser Phe Asp Val Asp Val Ser Asn Leu Pro Cys Gly Leu Asn Gly Ala
    130                 135                 140

Leu Tyr Phe Val Ala Met Asp Ala Asp Gly Gly Val Ser Lys Tyr Pro
145                 150                 155                 160

Thr Asn Thr Ala Gly Ala Lys Tyr Gly Thr Gly Tyr Cys Asp Ser Gln
                165                 170                 175

Cys Pro Arg Asp Leu Lys Phe Ile Asn Gly Gln Ala Asn Val Glu Gly
```

```
                180              185              190
Trp Glu Pro Ser Ser Asn Asn Ala Asn Thr Gly Ile Gly Asn His Gly
        195                 200                 205

Ser Cys Cys Ala Glu Met Asp Val Trp Glu Ala Asn Ser Ile Ser Thr
    210                 215                 220

Ala Val Thr Pro His Pro Cys Asp Thr Pro Gly Gln Thr Met Cys Gln
225                 230                 235                 240

Gly Asp Asp Cys Gly Gly Thr Tyr Ser Ser Thr Arg Tyr Ala Gly Thr
                245                 250                 255

Cys Asp Pro Asp Gly Cys Asp Phe Asn Pro Tyr Arg Met Gly Asn Thr
            260                 265                 270

Ser Phe Tyr Gly Pro Gly Lys Ile Ile Asp Thr Thr Lys Pro Phe Thr
        275                 280                 285

Val Val Thr Gln Phe Leu Thr Asp Asp Gly Thr Asp Gly Thr Leu
    290                 295                 300

Ser Glu Ile Lys Arg Phe Tyr Ile Gln Asn Ser Asn Val Ile Pro Gln
305                 310                 315                 320

Pro Asn Ser Asp Ile Ser Gly Val Thr Gly Asn Ser Ile Thr Thr Glu
                325                 330                 335

Phe Cys Thr Ala Gln Lys Gln Ala Phe Gly Asp Thr Asp Asp Phe Ser
            340                 345                 350

Gln His Gly Gly Leu Ala Lys Met Gly Ala Ala Met Gln Gln Gly Met
        355                 360                 365

Val Leu Val Met Ser Leu Trp Asp Asp His Ala Ala Asn Met Leu Trp
    370                 375                 380

Leu Asp Ser Thr Tyr Pro Thr Asp Ala Asp Pro Asp Thr Pro Gly Val
385                 390                 395                 400

Ala Arg Gly Thr Cys Pro Thr Thr Ser Gly Val Pro Ala Asp Val Glu
                405                 410                 415

Ser Gln Tyr Pro Asn Ser Tyr Val Ile Tyr Ser Asn Ile Lys Val Gly
            420                 425                 430

Pro Ile Asn Ser Thr Phe Thr Ala Asn
        435                 440

<210> SEQ ID NO 24
<211> LENGTH: 441
<212> TYPE: PRT
<213> ORGANISM: Artificial Sequence
<220> FEATURE:
<223> OTHER INFORMATION: Chimeric polypeptide 52152552

<400> SEQUENCE: 24

Gln Gln Ala Cys Thr Ala Thr Ala Glu Asn His Pro Pro Leu Thr Trp
1               5                   10                  15

Gln Glu Cys Thr Ala Pro Gly Ser Cys Thr Thr Gln Asn Gly Ala Val
            20                  25                  30

Val Ile Asp Ala Asn Trp Arg Trp Val His Thr Thr Ser Gly Tyr Thr
        35                  40                  45

Asn Cys Tyr Thr Gly Asn Thr Trp Asp Thr Ser Ile Cys Pro Asp Asp
    50                  55                  60

Val Thr Cys Ala Gln Asn Cys Cys Leu Asp Gly Ala Asp Tyr Ser Ser
65                  70                  75                  80

Thr Tyr Gly Ile Thr Thr Ser Gly Asp Ser Leu Asn Leu Lys Phe Val
                85                  90                  95

Thr Lys His Gln Tyr Gly Thr Asn Val Gly Ser Arg Val Tyr Leu Leu
```

```
                100                 105                 110
Gln Asp Asp Ser Thr Tyr Gln Ile Phe Lys Leu Leu Asn Arg Glu Phe
            115                 120                 125

Ser Phe Asp Val Asp Val Ser Asn Leu Pro Cys Gly Leu Asn Gly Ala
        130                 135                 140

Leu Tyr Phe Val Ala Met Ala Asp Gly Gly Val Ser Lys Tyr Pro
145                 150                 155                 160

Gly Asn Lys Ala Gly Ala Lys Tyr Gly Thr Gly Tyr Cys Asp Ser Gln
            165                 170                 175

Cys Pro Arg Asp Leu Lys Phe Ile Asn Gly Gln Ala Asn Val Glu Gly
        180                 185                 190

Trp Gln Pro Ser Ala Asn Asp Pro Asn Ala Gly Val Gly Asp His Gly
    195                 200                 205

Ser Cys Cys Ala Glu Met Asp Val Trp Glu Ala Asn Ser Ile Ser Asn
210                 215                 220

Ala Val Thr Pro His Pro Cys Asp Thr Pro Gly Gln Thr Met Cys Ser
225                 230                 235                 240

Gly Asp Asp Cys Gly Gly Thr Tyr Ser Asn Asp Arg Tyr Ala Gly Thr
                245                 250                 255

Cys Asp Pro Asp Gly Cys Asp Phe Asn Pro Tyr Arg Met Gly Asn Thr
            260                 265                 270

Ser Phe Tyr Gly Pro Gly Lys Ile Ile Asp Thr Thr Lys Pro Phe Thr
        275                 280                 285

Val Val Thr Gln Phe Leu Thr Asp Asp Gly Thr Asp Thr Gly Thr Leu
    290                 295                 300

Ser Glu Ile Lys Arg Phe Tyr Ile Gln Asn Ser Asn Val Ile Pro Gln
305                 310                 315                 320

Pro Asn Ser Asp Ile Ser Gly Val Thr Gly Asn Ser Ile Thr Thr Glu
                325                 330                 335

Phe Cys Thr Ala Gln Lys Gln Ala Phe Gly Asp Thr Asp Asp Phe Ser
            340                 345                 350

Gln His Gly Gly Leu Ala Lys Met Gly Ala Ala Met Gln Gln Gly Met
        355                 360                 365

Val Leu Val Met Ser Leu Trp Asp Asp His Ala Ala Asn Met Leu Trp
    370                 375                 380

Leu Asp Ser Thr Tyr Pro Thr Asp Ala Asp Pro Asp Thr Pro Gly Val
385                 390                 395                 400

Ala Arg Gly Thr Cys Pro Thr Thr Ser Gly Val Pro Ala Asp Val Glu
                405                 410                 415

Ser Gln Tyr Pro Asn Ser Tyr Val Ile Tyr Ser Asn Ile Lys Val Gly
            420                 425                 430

Pro Ile Asn Ser Thr Phe Thr Ala Asn
        435                 440

<210> SEQ ID NO 25
<211> LENGTH: 441
<212> TYPE: PRT
<213> ORGANISM: Artificial Sequence
<220> FEATURE:
<223> OTHER INFORMATION: Chimeric polypeptide 12153252

<400> SEQUENCE: 25

Gln Gln Ala Cys Ser Leu Thr Ala Glu Asn His Pro Ser Leu Thr Trp
1               5                   10                  15

Lys Arg Cys Thr Ser Gly Gly Ser Cys Ser Thr Val Asn Gly Ala Val
```

```
                20                  25                  30
Val Ile Asp Ala Asn Trp Arg Trp Val His Thr Thr Ser Gly Tyr Thr
                35                  40                  45
Asn Cys Tyr Thr Gly Asn Thr Trp Asp Thr Ser Ile Cys Pro Asp Asp
                50                  55                  60
Val Thr Cys Ala Gln Asn Cys Cys Leu Asp Gly Ala Asp Tyr Ser Ser
 65                  70                  75                  80
Thr Tyr Gly Ile Thr Thr Ser Gly Asp Ser Leu Asn Leu Lys Phe Val
                    85                  90                  95
Thr Lys His Gln Tyr Gly Thr Asn Val Gly Ser Arg Val Tyr Leu Leu
                100                 105                 110
Gln Asp Asp Ser Thr Tyr Gln Ile Phe Lys Leu Leu Asn Arg Glu Phe
                115                 120                 125
Ser Phe Asp Val Asp Val Ser Asn Leu Pro Cys Gly Leu Asn Gly Ala
                130                 135                 140
Leu Tyr Phe Val Ala Met Asp Ala Asp Gly Gly Val Ser Lys Tyr Pro
145                 150                 155                 160
Thr Asn Thr Ala Gly Ala Lys Tyr Gly Thr Gly Tyr Cys Asp Ser Gln
                165                 170                 175
Cys Pro Arg Asp Leu Lys Phe Ile Asn Gly Gln Ala Asn Val Glu Gly
                180                 185                 190
Trp Glu Pro Ser Ser Asn Asn Ala Asn Thr Gly Ile Gly Asn His Gly
                195                 200                 205
Ser Cys Cys Ala Glu Met Asp Val Trp Glu Ala Asn Ser Ile Ser Thr
                210                 215                 220
Ala Val Thr Pro His Pro Cys Asp Thr Pro Gly Gln Thr Met Cys Gln
225                 230                 235                 240
Gly Asp Asp Cys Gly Gly Thr Tyr Ser Ser Thr Arg Tyr Ala Gly Thr
                245                 250                 255
Cys Asp Pro Asp Gly Cys Asp Phe Asn Pro Tyr Arg Met Gly Asn Thr
                260                 265                 270
Ser Phe Tyr Gly Pro Gly Lys Ile Ile Asp Thr Thr Lys Pro Phe Thr
                275                 280                 285
Val Val Thr Gln Phe Leu Thr Asp Asp Gly Thr Asp Thr Gly Thr Leu
                290                 295                 300
Ser Glu Ile Lys Arg Phe Tyr Ile Gln Asn Ser Asn Val Ile Pro Gln
305                 310                 315                 320
Pro Asn Ser Asp Ile Ser Gly Val Thr Gly Asn Ser Ile Thr Thr Glu
                325                 330                 335
Phe Cys Thr Ala Gln Lys Gln Ala Phe Gly Asp Thr Asp Asp Phe Ser
                340                 345                 350
Gln His Gly Gly Leu Ala Lys Met Gly Ala Ala Met Gln Gln Gly Met
                355                 360                 365
Val Leu Val Met Ser Leu Trp Asp Asp His Ala Ala Asn Met Leu Trp
                370                 375                 380
Leu Asp Ser Thr Tyr Pro Thr Asp Ala Asp Pro Asp Thr Pro Gly Val
385                 390                 395                 400
Ala Arg Gly Thr Cys Pro Thr Thr Ser Gly Val Pro Ala Asp Val Glu
                405                 410                 415
Ser Gln Tyr Pro Asn Ser Tyr Val Ile Tyr Ser Asn Ile Lys Val Gly
                420                 425                 430
Pro Ile Asn Ser Thr Phe Thr Ala Asn
                435                 440
```

```
<210> SEQ ID NO 26
<211> LENGTH: 441
<212> TYPE: PRT
<213> ORGANISM: Artificial Sequence
<220> FEATURE:
<223> OTHER INFORMATION: Chimeric polypeptide 45153252

<400> SEQUENCE: 26

Gln Ala Ala Cys Ser Leu Thr Ala Glu Thr His Pro Ser Leu Gln Trp
  1               5                  10                  15

Gln Lys Cys Thr Ala Pro Gly Ser Cys Thr Thr Val Ser Gly Gln Val
                 20                  25                  30

Val Leu Asp Ala Asn Trp Arg Trp Val His Asp Val Asn Gly Tyr Thr
             35                  40                  45

Asn Cys Tyr Thr Gly Asn Thr Trp Asp Pro Thr Tyr Cys Pro Asp Asp
         50                  55                  60

Glu Thr Cys Ala Gln Asn Cys Cys Leu Asp Gly Ala Asp Tyr Ser Ser
 65                  70                  75                  80

Thr Tyr Gly Ile Thr Thr Ser Gly Asp Ser Leu Asn Leu Lys Phe Val
                 85                  90                  95

Thr Lys His Gln Tyr Gly Thr Asn Val Gly Ser Arg Val Tyr Leu Leu
            100                 105                 110

Gln Asp Asp Ser Thr Tyr Gln Ile Phe Lys Leu Leu Asn Arg Glu Phe
        115                 120                 125

Ser Phe Asp Val Asp Val Ser Asn Leu Pro Cys Gly Leu Asn Gly Ala
    130                 135                 140

Leu Tyr Phe Val Ala Met Asp Ala Asp Gly Gly Val Ser Lys Tyr Pro
145                 150                 155                 160

Thr Asn Thr Ala Gly Ala Lys Tyr Gly Thr Gly Tyr Cys Asp Ser Gln
                165                 170                 175

Cys Pro Arg Asp Leu Lys Phe Ile Asn Gly Gln Ala Asn Val Glu Gly
            180                 185                 190

Trp Glu Pro Ser Ser Asn Asn Ala Asn Thr Gly Ile Gly Asn His Gly
        195                 200                 205

Ser Cys Cys Ala Glu Met Asp Val Trp Glu Ala Asn Ser Ile Ser Thr
    210                 215                 220

Ala Val Thr Pro His Pro Cys Asp Thr Pro Gly Gln Thr Met Cys Gln
225                 230                 235                 240

Gly Asp Asp Cys Gly Gly Thr Tyr Ser Ser Thr Arg Tyr Ala Gly Thr
                245                 250                 255

Cys Asp Pro Asp Gly Cys Asp Phe Asn Pro Tyr Arg Met Gly Asn Thr
            260                 265                 270

Ser Phe Tyr Gly Pro Gly Lys Ile Ile Asp Thr Thr Lys Pro Phe Thr
        275                 280                 285

Val Val Thr Gln Phe Leu Thr Asp Asp Gly Thr Asp Thr Gly Thr Leu
    290                 295                 300

Ser Glu Ile Lys Arg Phe Tyr Ile Gln Asn Ser Asn Val Ile Pro Gln
305                 310                 315                 320

Pro Asn Ser Asp Ile Ser Gly Val Thr Gly Asn Ser Ile Thr Thr Glu
                325                 330                 335

Phe Cys Thr Ala Gln Lys Gln Ala Phe Gly Thr Asp Asp Phe Ser
            340                 345                 350

Gln His Gly Gly Leu Ala Lys Met Gly Ala Ala Met Gln Gln Gly Met
        355                 360                 365
```

```
Val Leu Val Met Ser Leu Trp Asp Asp His Ala Ala Asn Met Leu Trp
            370                 375                 380

Leu Asp Ser Thr Tyr Pro Thr Asp Ala Asp Pro Asp Thr Pro Gly Val
385                 390                 395                 400

Ala Arg Gly Thr Cys Pro Thr Thr Ser Gly Val Pro Ala Asp Val Glu
                405                 410                 415

Ser Gln Tyr Pro Asn Ser Tyr Val Ile Tyr Ser Asn Ile Lys Val Gly
                420                 425                 430

Pro Ile Asn Ser Thr Phe Thr Ala Asn
            435                 440

<210> SEQ ID NO 27
<211> LENGTH: 441
<212> TYPE: PRT
<213> ORGANISM: Artificial Sequence
<220> FEATURE:
<223> OTHER INFORMATION: Chimeric polypeptide 12153552

<400> SEQUENCE: 27

Gln Gln Ala Cys Ser Leu Thr Ala Glu Asn His Pro Ser Leu Thr Trp
1               5                   10                  15

Lys Arg Cys Thr Ser Gly Gly Ser Cys Ser Thr Val Asn Gly Ala Val
                20                  25                  30

Val Ile Asp Ala Asn Trp Arg Trp Val His Thr Thr Ser Gly Tyr Thr
            35                  40                  45

Asn Cys Tyr Thr Gly Asn Thr Trp Asp Thr Ser Ile Cys Pro Asp Asp
        50                  55                  60

Val Thr Cys Ala Gln Asn Cys Cys Leu Asp Gly Ala Asp Tyr Ser Ser
65                  70                  75                  80

Thr Tyr Gly Ile Thr Thr Ser Gly Asp Ser Leu Asn Leu Lys Phe Val
                85                  90                  95

Thr Lys His Gln Tyr Gly Thr Asn Val Gly Ser Arg Val Tyr Leu Leu
                100                 105                 110

Gln Asp Asp Ser Thr Tyr Gln Ile Phe Lys Leu Leu Asn Arg Glu Phe
            115                 120                 125

Ser Phe Asp Val Asp Val Ser Asn Leu Pro Cys Gly Leu Asn Gly Ala
        130                 135                 140

Leu Tyr Phe Val Ala Met Asp Ala Asp Gly Gly Val Ser Lys Tyr Pro
145                 150                 155                 160

Thr Asn Thr Ala Gly Ala Lys Tyr Gly Thr Gly Tyr Cys Asp Ser Gln
                165                 170                 175

Cys Pro Arg Asp Leu Lys Phe Ile Asn Gly Gln Ala Asn Val Glu Gly
            180                 185                 190

Trp Glu Pro Ser Ser Asn Asn Ala Asn Thr Gly Ile Gly Asp His Gly
        195                 200                 205

Ser Cys Cys Ala Glu Met Asp Val Trp Glu Ala Asn Ser Ile Ser Asn
    210                 215                 220

Ala Val Thr Pro His Pro Cys Asp Thr Pro Gly Gln Thr Met Cys Ser
225                 230                 235                 240

Gly Asp Asp Cys Gly Gly Thr Tyr Ser Asn Asp Arg Tyr Ala Gly Thr
                245                 250                 255

Cys Asp Pro Asp Gly Cys Asp Phe Asn Pro Tyr Arg Met Gly Asn Thr
            260                 265                 270

Ser Phe Tyr Gly Pro Gly Lys Ile Ile Asp Thr Thr Lys Pro Phe Thr
        275                 280                 285
```

```
Val Val Thr Gln Phe Leu Thr Asp Asp Gly Thr Asp Thr Gly Thr Leu
    290                 295                 300

Ser Glu Ile Lys Arg Phe Tyr Ile Gln Asn Ser Asn Val Ile Pro Gln
305                 310                 315                 320

Pro Asn Ser Asp Ile Ser Gly Val Thr Gly Asn Ser Ile Thr Thr Glu
                325                 330                 335

Phe Cys Thr Ala Gln Lys Gln Ala Phe Gly Asp Thr Asp Asp Phe Ser
                340                 345                 350

Gln His Gly Gly Leu Ala Lys Met Gly Ala Ala Met Gln Gln Gly Met
                355                 360                 365

Val Leu Val Met Ser Leu Trp Asp Asp His Ala Ala Asn Met Leu Trp
    370                 375                 380

Leu Asp Ser Thr Tyr Pro Thr Asp Ala Asp Pro Asp Thr Pro Gly Val
385                 390                 395                 400

Ala Arg Gly Thr Cys Pro Thr Thr Ser Gly Val Pro Ala Asp Val Glu
                405                 410                 415

Ser Gln Tyr Pro Asn Ser Tyr Val Ile Tyr Ser Asn Ile Lys Val Gly
                420                 425                 430

Pro Ile Asn Ser Thr Phe Thr Ala Asn
                435                 440

<210> SEQ ID NO 28
<211> LENGTH: 441
<212> TYPE: PRT
<213> ORGANISM: Artificial Sequence
<220> FEATURE:
<223> OTHER INFORMATION: Chimeric polypeptide 25152252

<400> SEQUENCE: 28

Gln Gln Ala Cys Thr Val Thr Ala Glu Asn His Pro Ser Leu Thr Trp
1               5                   10                  15

Gln Gln Cys Ser Ser Gly Gly Ser Cys Thr Thr Gln Asn Gly Lys Val
                20                  25                  30

Val Leu Asp Ala Asn Trp Arg Trp Val His Asp Val Asn Gly Tyr Thr
            35                  40                  45

Asn Cys Tyr Thr Gly Asn Thr Trp Asp Pro Thr Tyr Cys Pro Asp Asp
    50                  55                  60

Glu Thr Cys Ala Gln Asn Cys Cys Leu Asp Gly Ala Asp Tyr Ser Ser
65                  70                  75                  80

Thr Tyr Gly Ile Thr Thr Ser Gly Asp Ser Leu Asn Leu Lys Phe Val
                85                  90                  95

Thr Lys His Gln Tyr Gly Thr Asn Val Gly Ser Arg Val Tyr Leu Leu
                100                 105                 110

Gln Asp Asp Ser Thr Tyr Gln Ile Phe Lys Leu Leu Asn Arg Glu Phe
            115                 120                 125

Ser Phe Asp Val Asp Val Ser Asn Leu Pro Cys Gly Leu Asn Gly Ala
    130                 135                 140

Leu Tyr Phe Val Ala Met Asp Ala Asp Gly Gly Val Ser Lys Tyr Pro
145                 150                 155                 160

Gly Asn Lys Ala Gly Ala Lys Tyr Gly Thr Gly Tyr Cys Asp Ser Gln
                165                 170                 175

Cys Pro Arg Asp Leu Lys Phe Ile Asn Gly Gln Ala Asn Val Glu Gly
                180                 185                 190

Trp Gln Pro Ser Ala Asn Asp Pro Asn Ala Gly Val Gly Asn His Gly
            195                 200                 205
```

```
Ser Cys Cys Ala Glu Met Asp Val Trp Glu Ala Asn Ser Ile Ser Thr
        210                 215                 220

Ala Val Thr Pro His Pro Cys Asp Thr Pro Gly Gln Thr Met Cys Gln
225                 230                 235                 240

Gly Asp Asp Cys Gly Gly Thr Tyr Ser Ser Thr Arg Tyr Ala Gly Thr
                245                 250                 255

Cys Asp Pro Asp Gly Cys Asp Phe Asn Pro Tyr Arg Met Gly Asn Thr
                260                 265                 270

Ser Phe Tyr Gly Pro Gly Lys Ile Ile Asp Thr Thr Lys Pro Phe Thr
                275                 280                 285

Val Val Thr Gln Phe Leu Thr Asp Asp Gly Thr Asp Thr Gly Thr Leu
290                 295                 300

Ser Glu Ile Lys Arg Phe Tyr Ile Gln Asn Ser Asn Val Ile Pro Gln
305                 310                 315                 320

Pro Asn Ser Asp Ile Ser Gly Val Thr Gly Asn Ser Ile Thr Thr Glu
                325                 330                 335

Phe Cys Thr Ala Gln Lys Gln Ala Phe Gly Asp Thr Asp Asp Phe Ser
                340                 345                 350

Gln His Gly Gly Leu Ala Lys Met Gly Ala Ala Met Gln Gln Gly Met
                355                 360                 365

Val Leu Val Met Ser Leu Trp Asp Asp His Ala Ala Asn Met Leu Trp
370                 375                 380

Leu Asp Ser Thr Tyr Pro Thr Asp Ala Asp Pro Asp Thr Pro Gly Val
385                 390                 395                 400

Ala Arg Gly Thr Cys Pro Thr Thr Ser Gly Val Pro Ala Asp Val Glu
                405                 410                 415

Ser Gln Tyr Pro Asn Ser Tyr Val Ile Tyr Ser Asn Ile Lys Val Gly
                420                 425                 430

Pro Ile Asn Ser Thr Phe Thr Ala Asn
                435                 440

<210> SEQ ID NO 29
<211> LENGTH: 441
<212> TYPE: PRT
<213> ORGANISM: Artificial Sequence
<220> FEATURE:
<223> OTHER INFORMATION: Chimeric polypeptide 13152552

<400> SEQUENCE: 29

Gln Gln Ala Cys Ser Leu Thr Ala Glu Asn His Pro Ser Leu Thr Trp
1               5                   10                  15

Lys Arg Cys Thr Ser Gly Gly Ser Cys Ser Thr Val Asn Gly Ala Val
                20                  25                  30

Val Ile Asp Ala Asn Trp Arg Trp Thr His Ala Thr Asn Ser Ser Thr
            35                  40                  45

Asn Cys Tyr Asp Gly Asn Thr Trp Ser Ser Thr Leu Cys Pro Asp Asn
        50                  55                  60

Glu Thr Cys Ala Lys Asn Cys Cys Leu Asp Gly Ala Asp Tyr Ser Ser
65                  70                  75                  80

Thr Tyr Gly Ile Thr Thr Ser Gly Asp Ser Leu Asn Leu Lys Phe Val
                85                  90                  95

Thr Lys His Gln Tyr Gly Thr Asn Val Gly Ser Arg Val Tyr Leu Leu
                100                 105                 110

Gln Asp Asp Ser Thr Tyr Gln Ile Phe Lys Leu Leu Asn Arg Glu Phe
            115                 120                 125
```

```
Ser Phe Asp Val Asp Val Ser Asn Leu Pro Cys Gly Leu Asn Gly Ala
            130                 135                 140

Leu Tyr Phe Val Ala Met Asp Ala Asp Gly Gly Val Ser Lys Tyr Pro
145                 150                 155                 160

Gly Asn Lys Ala Gly Ala Lys Tyr Gly Thr Gly Tyr Cys Asp Ser Gln
                165                 170                 175

Cys Pro Arg Asp Leu Lys Phe Ile Asn Gly Gln Ala Asn Val Glu Gly
            180                 185                 190

Trp Gln Pro Ser Ala Asn Asp Pro Asn Ala Gly Val Gly Asp His Gly
            195                 200                 205

Ser Cys Cys Ala Glu Met Asp Val Trp Glu Ala Asn Ser Ile Ser Asn
210                 215                 220

Ala Val Thr Pro His Pro Cys Asp Thr Pro Gly Gln Thr Met Cys Ser
225                 230                 235                 240

Gly Asp Asp Cys Gly Gly Thr Tyr Ser Asn Asp Arg Tyr Ala Gly Thr
                245                 250                 255

Cys Asp Pro Asp Gly Cys Asp Phe Asn Pro Tyr Arg Met Gly Asn Thr
            260                 265                 270

Ser Phe Tyr Gly Pro Gly Lys Ile Ile Asp Thr Thr Lys Pro Phe Thr
            275                 280                 285

Val Val Thr Gln Phe Leu Thr Asp Asp Gly Thr Asp Thr Gly Thr Leu
290                 295                 300

Ser Glu Ile Lys Arg Phe Tyr Ile Gln Asn Ser Asn Val Ile Pro Gln
305                 310                 315                 320

Pro Asn Ser Asp Ile Ser Gly Val Thr Gly Asn Ser Ile Thr Thr Glu
                325                 330                 335

Phe Cys Thr Ala Gln Lys Gln Ala Phe Gly Asp Thr Asp Asp Phe Ser
            340                 345                 350

Gln His Gly Gly Leu Ala Lys Met Gly Ala Ala Met Gln Gln Gly Met
            355                 360                 365

Val Leu Val Met Ser Leu Trp Asp Asp His Ala Ala Asn Met Leu Trp
370                 375                 380

Leu Asp Ser Thr Tyr Pro Thr Asp Ala Asp Pro Asp Thr Pro Gly Val
385                 390                 395                 400

Ala Arg Gly Thr Cys Pro Thr Thr Ser Gly Val Pro Ala Asp Val Glu
                405                 410                 415

Ser Gln Tyr Pro Asn Ser Tyr Val Ile Tyr Ser Asn Ile Lys Val Gly
            420                 425                 430

Pro Ile Asn Ser Thr Phe Thr Ala Asn
            435                 440

<210> SEQ ID NO 30
<211> LENGTH: 441
<212> TYPE: PRT
<213> ORGANISM: Artificial Sequence
<220> FEATURE:
<223> OTHER INFORMATION: Chimeric polypeptide 12152252

<400> SEQUENCE: 30

Gln Gln Ala Cys Ser Leu Thr Ala Glu Asn His Pro Ser Leu Thr Trp
1               5                   10                  15

Lys Arg Cys Thr Ser Gly Gly Ser Cys Ser Thr Val Asn Gly Ala Val
            20                  25                  30

Val Ile Asp Ala Asn Trp Arg Trp Val His Thr Thr Ser Gly Tyr Thr
        35                  40                  45
```

```
Asn Cys Tyr Thr Gly Asn Thr Trp Asp Thr Ser Ile Cys Pro Asp Asp
 50                  55                  60

Val Thr Cys Ala Gln Asn Cys Cys Leu Asp Gly Ala Asp Tyr Ser Ser
 65                  70                  75                  80

Thr Tyr Gly Ile Thr Thr Ser Gly Asp Ser Leu Asn Leu Lys Phe Val
                 85                  90                  95

Thr Lys His Gln Tyr Gly Thr Asn Val Gly Ser Arg Val Tyr Leu Leu
            100                 105                 110

Gln Asp Asp Ser Thr Tyr Gln Ile Phe Lys Leu Leu Asn Arg Glu Phe
        115                 120                 125

Ser Phe Asp Val Asp Val Ser Asn Leu Pro Cys Gly Leu Asn Gly Ala
130                 135                 140

Leu Tyr Phe Val Ala Met Asp Ala Asp Gly Gly Val Ser Lys Tyr Pro
145                 150                 155                 160

Gly Asn Lys Ala Gly Ala Lys Tyr Gly Thr Gly Tyr Cys Asp Ser Gln
                165                 170                 175

Cys Pro Arg Asp Leu Lys Phe Ile Asn Gly Gln Ala Asn Val Glu Gly
            180                 185                 190

Trp Gln Pro Ser Ala Asn Asp Pro Asn Ala Gly Val Gly Asn His Gly
        195                 200                 205

Ser Cys Cys Ala Glu Met Asp Val Trp Glu Ala Asn Ser Ile Ser Thr
210                 215                 220

Ala Val Thr Pro His Pro Cys Asp Thr Pro Gly Gln Thr Met Cys Gln
225                 230                 235                 240

Gly Asp Asp Cys Gly Gly Thr Tyr Ser Ser Thr Arg Tyr Ala Gly Thr
                245                 250                 255

Cys Asp Pro Asp Gly Cys Asp Phe Asn Pro Tyr Arg Met Gly Asn Thr
            260                 265                 270

Ser Phe Tyr Gly Pro Gly Lys Ile Ile Asp Thr Thr Lys Pro Phe Thr
        275                 280                 285

Val Val Thr Gln Phe Leu Thr Asp Asp Gly Thr Asp Thr Gly Thr Leu
290                 295                 300

Ser Glu Ile Lys Arg Phe Tyr Ile Gln Asn Ser Asn Val Ile Pro Gln
305                 310                 315                 320

Pro Asn Ser Asp Ile Ser Gly Val Thr Gly Asn Ser Ile Thr Thr Glu
                325                 330                 335

Phe Cys Thr Ala Gln Lys Gln Ala Phe Gly Asp Thr Asp Asp Phe Ser
            340                 345                 350

Gln His Gly Gly Leu Ala Lys Met Gly Ala Ala Met Gln Gln Gly Met
        355                 360                 365

Val Leu Val Met Ser Leu Trp Asp Asp His Ala Ala Asn Met Leu Trp
370                 375                 380

Leu Asp Ser Thr Tyr Pro Thr Asp Ala Asp Pro Asp Thr Pro Gly Val
385                 390                 395                 400

Ala Arg Gly Thr Cys Pro Thr Thr Ser Gly Val Pro Ala Asp Val Glu
                405                 410                 415

Ser Gln Tyr Pro Asn Ser Tyr Val Ile Tyr Ser Asn Ile Lys Val Gly
            420                 425                 430

Pro Ile Asn Ser Thr Phe Thr Ala Asn
        435                 440

<210> SEQ ID NO 31
<211> LENGTH: 441
```

```
<212> TYPE: PRT
<213> ORGANISM: Artificial Sequence
<220> FEATURE:
<223> OTHER INFORMATION: Chimeric polypeptide 55153252

<400> SEQUENCE: 31
```

| | | | | | | | | | | | | | | |
|---|---|---|---|---|---|---|---|---|---|---|---|---|---|---|
| Gln | Gln | Ala | Cys | Thr | Ala | Thr | Ala | Glu | Asn | His | Pro | Pro | Leu | Thr | Trp |
| 1 | | | | 5 | | | | | 10 | | | | | 15 | |

Gln Glu Cys Thr Ala Pro Gly Ser Cys Thr Thr Gln Asn Gly Ala Val
              20                  25                  30

Val Leu Asp Ala Asn Trp Arg Trp Val His Asp Val Asn Gly Tyr Thr
          35                  40                  45

Asn Cys Tyr Thr Gly Asn Thr Trp Asp Pro Thr Tyr Cys Pro Asp Asp
    50                  55                  60

Glu Thr Cys Ala Gln Asn Cys Cys Leu Asp Gly Ala Asp Tyr Ser Ser
65                  70                  75                  80

Thr Tyr Gly Ile Thr Thr Ser Gly Asp Ser Leu Asn Leu Lys Phe Val
            85                  90                  95

Thr Lys His Gln Tyr Gly Thr Asn Val Gly Ser Arg Val Tyr Leu Leu
            100                 105                 110

Gln Asp Asp Ser Thr Tyr Gln Ile Phe Lys Leu Leu Asn Arg Glu Phe
            115                 120                 125

Ser Phe Asp Val Asp Val Ser Asn Leu Pro Cys Gly Leu Asn Gly Ala
    130                 135                 140

Leu Tyr Phe Val Ala Met Asp Ala Asp Gly Gly Val Ser Lys Tyr Pro
145                 150                 155                 160

Thr Asn Thr Ala Gly Ala Lys Tyr Gly Thr Gly Tyr Cys Asp Ser Gln
                165                 170                 175

Cys Pro Arg Asp Leu Lys Phe Ile Asn Gly Gln Ala Asn Val Glu Gly
            180                 185                 190

Trp Glu Pro Ser Ser Asn Asn Ala Asn Thr Gly Ile Gly Asn His Gly
            195                 200                 205

Ser Cys Cys Ala Glu Met Asp Val Trp Glu Ala Asn Ser Ile Ser Thr
    210                 215                 220

Ala Val Thr Pro His Pro Cys Asp Thr Pro Gly Gln Thr Met Cys Gln
225                 230                 235                 240

Gly Asp Asp Cys Gly Gly Thr Tyr Ser Ser Thr Arg Tyr Ala Gly Thr
                245                 250                 255

Cys Asp Pro Asp Gly Cys Asp Phe Asn Pro Tyr Arg Met Gly Asn Thr
            260                 265                 270

Ser Phe Tyr Gly Pro Gly Lys Ile Ile Asp Thr Thr Lys Pro Phe Thr
    275                 280                 285

Val Val Thr Gln Phe Leu Thr Asp Asp Gly Thr Asp Thr Gly Thr Leu
    290                 295                 300

Ser Glu Ile Lys Arg Phe Tyr Ile Gln Asn Ser Asn Val Ile Pro Gln
305                 310                 315                 320

Pro Asn Ser Asp Ile Ser Gly Val Thr Gly Asn Ser Ile Thr Thr Glu
            325                 330                 335

Phe Cys Thr Ala Gln Lys Gln Ala Phe Gly Asp Thr Asp Asp Phe Ser
            340                 345                 350

Gln His Gly Gly Leu Ala Lys Met Gly Ala Ala Met Gln Gln Gly Met
            355                 360                 365

Val Leu Val Met Ser Leu Trp Asp Asp His Ala Ala Asn Met Leu Trp
    370                 375                 380

```
Leu Asp Ser Thr Tyr Pro Thr Asp Ala Asp Pro Asp Thr Pro Gly Val
385                 390                 395                 400

Ala Arg Gly Thr Cys Pro Thr Thr Ser Gly Val Pro Ala Asp Val Glu
            405                 410                 415

Ser Gln Tyr Pro Asn Ser Tyr Val Ile Tyr Ser Asn Ile Lys Val Gly
            420                 425                 430

Pro Ile Asn Ser Thr Phe Thr Ala Asn
        435                 440

<210> SEQ ID NO 32
<211> LENGTH: 437
<212> TYPE: PRT
<213> ORGANISM: Artificial Sequence
<220> FEATURE:
<223> OTHER INFORMATION: Chimeric polypeptide 55552252

<400> SEQUENCE: 32

Gln Gln Ala Cys Thr Ala Thr Ala Glu Asn His Pro Pro Leu Thr Trp
1               5                   10                  15

Gln Glu Cys Thr Ala Pro Gly Ser Cys Thr Thr Gln Asn Gly Ala Val
                20                  25                  30

Val Leu Asp Ala Asn Trp Arg Trp Val His Asp Val Asn Gly Tyr Thr
            35                  40                  45

Asn Cys Tyr Thr Gly Asn Thr Trp Asp Pro Thr Tyr Cys Pro Asp Asp
    50                  55                  60

Glu Thr Cys Ala Gln Asn Cys Cys Leu Asp Gly Ala Asp Tyr Glu Gly
65                  70                  75                  80

Thr Tyr Gly Val Thr Ser Ser Gly Ser Ser Leu Lys Leu Asn Phe Val
                85                  90                  95

Thr Gly Ser Asn Val Gly Ser Arg Leu Tyr Leu Leu Gln Asp Asp Ser
            100                 105                 110

Thr Tyr Gln Ile Phe Lys Leu Leu Asn Arg Glu Phe Ser Phe Asp Val
        115                 120                 125

Asp Val Ser Asn Leu Pro Cys Gly Leu Asn Gly Ala Leu Tyr Phe Val
    130                 135                 140

Ala Met Asp Ala Asp Gly Gly Val Ser Lys Tyr Pro Gly Asn Lys Ala
145                 150                 155                 160

Gly Ala Lys Tyr Gly Thr Gly Tyr Cys Asp Ser Gln Cys Pro Arg Asp
                165                 170                 175

Leu Lys Phe Ile Asn Gly Gln Ala Asn Val Glu Gly Trp Gln Pro Ser
            180                 185                 190

Ala Asn Asp Pro Asn Ala Gly Val Gly Asn His Gly Ser Cys Cys Ala
        195                 200                 205

Glu Met Asp Val Trp Glu Ala Asn Ser Ile Ser Thr Ala Val Thr Pro
    210                 215                 220

His Pro Cys Asp Thr Pro Gly Gln Thr Met Cys Gln Gly Asp Asp Cys
225                 230                 235                 240

Gly Gly Thr Tyr Ser Ser Thr Arg Tyr Ala Gly Thr Cys Asp Pro Asp
                245                 250                 255

Gly Cys Asp Phe Asn Pro Tyr Arg Met Gly Asn Thr Ser Phe Tyr Gly
            260                 265                 270

Pro Gly Lys Ile Ile Asp Thr Lys Pro Phe Thr Val Val Thr Gln
        275                 280                 285

Phe Leu Thr Asp Asp Gly Thr Asp Thr Gly Thr Leu Ser Glu Ile Lys
    290                 295                 300
```

```
Arg Phe Tyr Ile Gln Asn Ser Asn Val Ile Pro Gln Pro Asn Ser Asp
305                 310                 315                 320

Ile Ser Gly Val Thr Gly Asn Ser Ile Thr Thr Glu Phe Cys Thr Ala
                325                 330                 335

Gln Lys Gln Ala Phe Gly Asp Thr Asp Asp Phe Ser Gln His Gly Gly
            340                 345                 350

Leu Ala Lys Met Gly Ala Ala Met Gln Gln Gly Met Val Leu Val Met
        355                 360                 365

Ser Leu Trp Asp Asp His Ala Ala Asn Met Leu Trp Leu Asp Ser Thr
    370                 375                 380

Tyr Pro Thr Asp Ala Asp Pro Asp Thr Pro Gly Val Ala Arg Gly Thr
385                 390                 395                 400

Cys Pro Thr Thr Ser Gly Val Pro Ala Asp Val Glu Ser Gln Tyr Pro
                405                 410                 415

Asn Ser Tyr Val Ile Tyr Ser Asn Ile Lys Val Gly Pro Ile Asn Ser
                420                 425                 430

Thr Phe Thr Ala Asn
            435

<210> SEQ ID NO 33
<211> LENGTH: 441
<212> TYPE: PRT
<213> ORGANISM: Artificial Sequence
<220> FEATURE:
<223> OTHER INFORMATION: Chimeric polypeptide 55152552

<400> SEQUENCE: 33

Gln Gln Ala Cys Thr Ala Thr Ala Glu Asn His Pro Pro Leu Thr Trp
1               5                   10                  15

Gln Glu Cys Thr Ala Pro Gly Ser Cys Thr Thr Gln Asn Gly Ala Val
            20                  25                  30

Val Leu Asp Ala Asn Trp Arg Trp Val His Asp Val Asn Gly Tyr Thr
        35                  40                  45

Asn Cys Tyr Thr Gly Asn Thr Trp Asp Pro Thr Tyr Cys Pro Asp Asp
    50                  55                  60

Glu Thr Cys Ala Gln Asn Cys Cys Leu Asp Gly Ala Asp Tyr Ser Ser
65                  70                  75                  80

Thr Tyr Gly Ile Thr Thr Ser Gly Asp Ser Leu Asn Leu Lys Phe Val
                85                  90                  95

Thr Lys His Gln Tyr Gly Thr Asn Val Gly Ser Arg Val Tyr Leu Leu
            100                 105                 110

Gln Asp Asp Ser Thr Tyr Gln Ile Phe Lys Leu Leu Asn Arg Glu Phe
        115                 120                 125

Ser Phe Asp Val Asp Val Ser Asn Leu Pro Cys Gly Leu Asn Gly Ala
    130                 135                 140

Leu Tyr Phe Val Ala Met Asp Ala Asp Gly Gly Val Ser Lys Tyr Pro
145                 150                 155                 160

Gly Asn Lys Ala Gly Ala Lys Tyr Gly Thr Gly Tyr Cys Asp Ser Gln
                165                 170                 175

Cys Pro Arg Asp Leu Lys Phe Ile Asn Gly Gln Ala Asn Val Glu Gly
            180                 185                 190

Trp Gln Pro Ser Ala Asn Asp Pro Asn Ala Gly Val Gly Asp His Gly
        195                 200                 205

Ser Cys Cys Ala Glu Met Asp Val Trp Glu Ala Asn Ser Ile Ser Asn
    210                 215                 220
```

```
Ala Val Thr Pro His Pro Cys Asp Thr Pro Gly Gln Thr Met Cys Ser
225                 230                 235                 240

Gly Asp Asp Cys Gly Gly Thr Tyr Ser Asn Asp Arg Tyr Ala Gly Thr
            245                 250                 255

Cys Asp Pro Asp Gly Cys Asp Phe Asn Pro Tyr Arg Met Gly Asn Thr
        260                 265                 270

Ser Phe Tyr Gly Pro Gly Lys Ile Ile Asp Thr Thr Lys Pro Phe Thr
    275                 280                 285

Val Val Thr Gln Phe Leu Thr Asp Asp Gly Thr Asp Thr Gly Thr Leu
    290                 295                 300

Ser Glu Ile Lys Arg Phe Tyr Ile Gln Asn Ser Asn Val Ile Pro Gln
305                 310                 315                 320

Pro Asn Ser Asp Ile Ser Gly Val Thr Gly Asn Ser Ile Thr Thr Glu
            325                 330                 335

Phe Cys Thr Ala Gln Lys Gln Ala Phe Gly Asp Thr Asp Asp Phe Ser
        340                 345                 350

Gln His Gly Gly Leu Ala Lys Met Gly Ala Ala Met Gln Gln Gly Met
    355                 360                 365

Val Leu Val Met Ser Leu Trp Asp Asp His Ala Ala Asn Met Leu Trp
    370                 375                 380

Leu Asp Ser Thr Tyr Pro Thr Asp Ala Asp Pro Asp Thr Pro Gly Val
385                 390                 395                 400

Ala Arg Gly Thr Cys Pro Thr Thr Ser Gly Val Pro Ala Asp Val Glu
            405                 410                 415

Ser Gln Tyr Pro Asn Ser Tyr Val Ile Tyr Ser Asn Ile Lys Val Gly
            420                 425                 430

Pro Ile Asn Ser Thr Phe Thr Ala Asn
            435                 440

<210> SEQ ID NO 34
<211> LENGTH: 441
<212> TYPE: PRT
<213> ORGANISM: Artificial Sequence
<220> FEATURE:
<223> OTHER INFORMATION: Chimeric polypeptide 55152252

<400> SEQUENCE: 34

Gln Gln Ala Cys Thr Ala Thr Ala Glu Asn His Pro Pro Leu Thr Trp
1               5                   10                  15

Gln Glu Cys Thr Ala Pro Gly Ser Cys Thr Thr Gln Asn Gly Ala Val
            20                  25                  30

Val Leu Asp Ala Asn Trp Arg Trp Val His Asp Val Asn Gly Tyr Thr
        35                  40                  45

Asn Cys Tyr Thr Gly Asn Thr Trp Asp Pro Thr Tyr Cys Pro Asp Asp
    50                  55                  60

Glu Thr Cys Ala Gln Asn Cys Cys Leu Asp Gly Ala Asp Tyr Ser Ser
65                  70                  75                  80

Thr Tyr Gly Ile Thr Thr Ser Gly Asp Ser Leu Asn Leu Lys Phe Val
                85                  90                  95

Thr Lys His Gln Tyr Gly Thr Asn Val Gly Ser Arg Val Tyr Leu Leu
            100                 105                 110

Gln Asp Asp Ser Thr Tyr Gln Ile Phe Lys Leu Leu Asn Arg Glu Phe
        115                 120                 125

Ser Phe Asp Val Asp Val Ser Asn Leu Pro Cys Gly Leu Asn Gly Ala
    130                 135                 140
```

```
Leu Tyr Phe Val Ala Met Asp Ala Asp Gly Val Ser Lys Tyr Pro
145                 150                 155                 160

Gly Asn Lys Ala Gly Ala Lys Tyr Gly Thr Gly Tyr Cys Asp Ser Gln
                165                 170                 175

Cys Pro Arg Asp Leu Lys Phe Ile Asn Gly Gln Ala Asn Val Glu Gly
            180                 185                 190

Trp Gln Pro Ser Ala Asn Asp Pro Asn Ala Gly Val Gly Asn His Gly
        195                 200                 205

Ser Cys Cys Ala Glu Met Asp Val Trp Glu Ala Asn Ser Ile Ser Thr
    210                 215                 220

Ala Val Thr Pro His Pro Cys Asp Thr Pro Gly Gln Thr Met Cys Gln
225                 230                 235                 240

Gly Asp Asp Cys Gly Gly Thr Tyr Ser Ser Thr Arg Tyr Ala Gly Thr
                245                 250                 255

Cys Asp Pro Asp Gly Cys Asp Phe Asn Pro Tyr Arg Met Gly Asn Thr
            260                 265                 270

Ser Phe Tyr Gly Pro Gly Lys Ile Ile Asp Thr Thr Lys Pro Phe Thr
        275                 280                 285

Val Val Thr Gln Phe Leu Thr Asp Asp Gly Thr Asp Thr Gly Thr Leu
    290                 295                 300

Ser Glu Ile Lys Arg Phe Tyr Ile Gln Asn Ser Asn Val Ile Pro Gln
305                 310                 315                 320

Pro Asn Ser Asp Ile Ser Gly Val Thr Gly Asn Ser Ile Thr Thr Glu
                325                 330                 335

Phe Cys Thr Ala Gln Lys Gln Ala Phe Gly Asp Thr Asp Asp Phe Ser
            340                 345                 350

Gln His Gly Gly Leu Ala Lys Met Gly Ala Ala Met Gln Gln Gly Met
        355                 360                 365

Val Leu Val Met Ser Leu Trp Asp Asp His Ala Ala Asn Met Leu Trp
    370                 375                 380

Leu Asp Ser Thr Tyr Pro Thr Asp Ala Asp Pro Asp Thr Pro Gly Val
385                 390                 395                 400

Ala Arg Gly Thr Cys Pro Thr Thr Ser Gly Val Pro Ala Asp Val Glu
                405                 410                 415

Ser Gln Tyr Pro Asn Ser Tyr Val Ile Tyr Ser Asn Ile Lys Val Gly
            420                 425                 430

Pro Ile Asn Ser Thr Phe Thr Ala Asn
            435                 440
```